US008809017B2

(12) United States Patent
Yang et al.

(10) Patent No.: US 8,809,017 B2
(45) Date of Patent: Aug. 19, 2014

(54) IRES MEDIATED MULTICISTRONIC VECTORS

(75) Inventors: Yuansheng Yang, Centros (SG); Steven Ho, Centros (SG); Jia Juan Lee, Centros (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/479,756

(22) Filed: May 24, 2012

(65) Prior Publication Data

US 2012/0301919 A1    Nov. 29, 2012

Related U.S. Application Data

(60) Provisional application No. 61/489,277, filed on May 24, 2011.

(51) Int. Cl.

| | | |
|---|---|---|
| C12P 21/06 | (2006.01) | |
| C12P 1/00 | (2006.01) | |
| C12P 21/04 | (2006.01) | |
| C12N 5/02 | (2006.01) | |
| C12N 5/07 | (2010.01) | |
| C12N 15/00 | (2006.01) | |
| C07H 21/04 | (2006.01) | |

(52) U.S. Cl.
USPC ........ 435/69.1; 435/41; 435/70.1; 435/70.21; 435/71.1; 435/320.1; 435/325; 435/326; 435/440; 435/455; 536/23.1; 536/23.53; 536/24.1

(58) Field of Classification Search
None
See application file for complete search history.

(56) References Cited

U.S. PATENT DOCUMENTS 6,878,531 B1 * 4/2005 Seyfang ...................... 435/91.2
2004/0234974 A1 * 11/2004 Yamamoto et al. ............... 435/6

OTHER PUBLICATIONS

Mielke et al. "Stabilized, long-term expression of heterodimeric proteins from tricistronic mRNA" 254 Gene 1-8 (2000).*
Zimmermann et al., "The Complete Nucleotide Sequence and Construction of an Infectious cDNA Clone of a Highly Virulent Encephalomyocarditis Virus" 203 Virology 366-372 (1994).*
Witherell et al., "Encephalomyocarditis Virus Internal Ribosomal Entry Site RNA-Protein Interactions" 68(5) Journal of Virology 3183-3192 (1994).*
Aggarwal, What's fueling the biotech engine—2009-2010. 2010. Nature Biotechnology 28(11):1165-1171.
Antoniou M, Harland L, Mustoe T, Williams S, Holdstock J, Yague E, Mulcahy T, Griffiths M, Edwards S, Ioannou PA and others. 2003. Transgenes encompassing dual-promoter CpG islands from the human TBP and HNRPA2B1 loci are resistant to heterochromatin-mediated silencing. Genomics 82(3):269-279.
Barnes LM, Bentley CM, Dickson AJ. 2003. Stability of protein production from recombinant mammalian cells. Biotechnol Bioeng 81(6):631-9.
Barnes LM, Bentley CM, Moy N, Dickson AJ. 2007. Molecular analysis of successful cell line selection in transfected GS-NS0 myeloma cells. Biotechnol Bioeng 96(2):337-48.
Barnett, RS et al., Chapter 3: Antibody production in chinese hamster ovary cells using an impaired selectable marker. 1995. Antibody Expression and Engineering. 604: 27-40.
Birch JR, Racher AJ. 2006. Antibody production. Adv Drug Deliv Rev 58(5-6):671-685.
Bittker, J. A. et al., Nucleic acid evolution and minimization by nonhomologous random recombination. (2002) Nat. Biotechnol. 20, 1024-1029.
Bochkov YA, Palmenberg AC. 2006. Translational efficiency of EMCV IRES in bicistronic vectors is dependent upon IRES sequence and gene location. Biotechniques 41(3):283-284, 286, 288 passim.
Borman AM, Bailly JL, Girard M, Kean KM. 1995. Picornavirus internal ribosome entry segments: Comparison of translation efficiency and the requirements for optimal internal initiation of translation in vitro. Nucleic Acids Research 23(18):3656-3663.
Borman AM, LeMercier P, Girard M, Kean KM. 1997. Comparison of picornaviral IRES-driven internal initiation of translation in cultured cells of different origins. Nucleic Acids Research 25(5):925-932.
Chen L, Xie Z, Teng Y, Wang M, Shi M, Qian L, Hu M, Feng J, Yang X, Shen B and others. 2004. Highly efficient selection of the stable clones expressing antibody-IL-2 fusion protein by a dicistronic expression vector containing a mutant neo gene. J Immunol Methods 295(1-2):49-56.
Chusainow J, Yang YS, Yeo JH, Toh PC, Asvadi P, Wong NS, Yap MG. 2009. A study of monoclonal antibody-producing CHO cell lines: what makes a stable high producer? Biotechnol Bioeng 102(4):1182-96.
Ciucanu I and Kerek F, A simple and rapid method for the permethylation of carbohydrates. Carbohydrate Research, 131(2):209-217,1984.
Dang Q, Auten J, Plavec I. 2000. Human beta interferon scaffold attachment region inhibits de novo methylation and confers long-term, copy number-dependent expression to a retroviral vector. Journal of Virology 74(6):2671-2678.
Davies MV, Kaufman RJ. 1992. The Sequence Context of the Initiation Codon in the Encephalomyocarditis Virus Leader Modulates Efficiency of Internal Translation Initiation. Journal of Virology 66(4):1924-1932.
Dell A et al., Mass spectrometry of carbohydrate-containing bipolymers. Methods in Enzymology, 230:108-132, 1994.
Eszterhas SK, Bouhassira EE, Martin DI, Fiering S. 2002. Transcriptional interference by independently regulated genes occurs in any relative arrangement of the genes and is influenced by chromosomal integration position. Mol Cell Biol 22(2):469-79.

(Continued)

*Primary Examiner* — Jennifer Dunston
*Assistant Examiner* — Nancy J. Leith
(74) *Attorney, Agent, or Firm* — Wolf, Greenfield & Sacks, P.C.

(57) ABSTRACT

This invention relates to nucleic acid molecules comprising at least one nucleic acid sequence encoding for a peptide or protein of interest, at least one nucleic acid sequence encoding for a selectable marker, and at least one IRES sequence, wherein the at least one IRES sequence is located between the at least one nucleic acid sequence encoding for the peptide or protein of interest and the at least one nucleic acid sequence encoding for the selectable marker. Furthermore, this invention relates to host cells comprising such nucleic acid molecule and to methods of recombinant protein expression using such host cells.

33 Claims, 19 Drawing Sheets

(56) References Cited

OTHER PUBLICATIONS

Fang et al., An antibody delivery system for regulated expression of therapeutic levels of monoclonal antibodies in vivo. Molec Ther. 2007;15:1153-9.

Fang, J., J. J. Qian, et al. (2005). "Stable antibody expression at therapeutic levels using the 2A peptide." Nature Biotechnology 23(5): 584-590.

Feng YQ, Lorincz MC, Fiering S, Greally JM, Bouhassira EE. 2001. Position effects are influenced by the orientation of a transgene with respect to flanking chromatin. Molecular and Cellular Biology 21(1):298-309.

Funston GM and Kallioinen SE, Expression of heterologous genes in oncolytic adenoviruses using picornaviral 2A sequences that trigger ribsome skipping. J of general Virology, 89(2), 389-396, 2008.

Fussenegger M, Mazur X, Bailey JE. 1998. pTRIDENT, a novel vector family for tricistronic gene expression in mammalian cells. Biotechnol Bioeng 57(1):1-10.

Fussenegger, M et al. Genetic optimization of recombinant gylcoprotein production by mammalian cells. 1999. Trends in Biotechnology 17(1): 35-42.

Gonzalez R, Andrews BA, Asenjo JA. 2002. Kinetic model of BiP- and PDI-mediated protein folding and assembly. J Theor Biol 214(4):529-37.

Gurtu V, Yan G, Zhang G. 1996. IRES bicistronic expression vectors for efficient creation of stable mammalian cell lines. Biochem Biophys Res Commun 229(1):295-8.

Harvey, DJ, Quantitative aspects of the matrix-assisted laser desorption mass spectrometry of complex oligosaccharides. Rapid Communications in mass spectrometry: RCM, 7(7):614-619, 1993.

Hastings PJ, Lupski JR, Rosenberg SM, Ira G. 2009. Mechanisms of change in gene copy number. Nature Reviews Genetics 10(8):551-564.

Hennecke M, Kwissa M, Metzger K, Oumard A, Kroger A, Schirmbeck R, Reimann J, Hauser H. 2001. Composition and arrangement of genes define the strength of IRES-driven translation in bicistronic mRNAs. Nucleic Acids Res 29(16):3327-34.

Hu, T., Q. Fu, et al. (2009). "Generation of a stable mammalian cell line for simultaneous expression of multiple genes by using 2A peptide-based lentiviral vector." Biotechnology Letters 31(3): 353-359.

Ibrahimi, A., G. V. Velde, et al. (2009). "Highly efficient multicistronic lentiviral vectors with peptide 2A sequences." Human Gene Therapy 20(8): 845-860.

Jefferis R, Glycosylation of human IgG antibodies. BioPharm 14(9):19-27, 2001.

Jefferis R, Glycosylation of recombinant antibody therapeutics. Biotechnology Progress, 21(1), 11-16, 2005.

Jiang Z, Huang Y, Sharfstein ST. 2006. Regulation of recombinant monoclonal antibody production in chinese hamster ovary cells: a comparative study of gene copy number, mRNA level, and protein expression. Biotechnol Prog 22(1):313-8.

Jostock T, Vanhove M, Brepoels E, van Gool R, Daukandt M, Wehnert A, van Hegelsom R, Dransfield D, Sexton D, Devlin M and others. 2004. Rapid generation of functional human IgG antibodies derived from Fab-on-phage display libraries. Journal of Immunological Methods 289(12):65-80.

Jun SC, Kim MS, Hong HJ, Lee GM. 2006. Limitations to the development of humanized antibody producing Chinese hamster ovary cells using glutamine synthetase-mediated gene amplification. Biotechnol Prog 22(3):770-80.

Kaminski A, Belsham GJ, Jackson RJ. 1994. Translation of Encephalomyocarditis Virus-Rna-Parameters Influencing the Selection of the Internal Initiation Site. Embo Journal 13(7):1673-1681.

Kang P et al., Comparative glycomic mapping through quantitative permethylation and stable-isotope labeling. Analytical Chemistry, 79 (16), 6064-6073, 2007.

Kao FT and Puck TT, Genetics of somatic mammalian cells, VII. Indication and isolation of nutritional mutants in chinese hamster cells. Proc. Natl. Acad. Sci. USA, vol. 60, p. 1275, 1968.

Kaufman RJ, Davies MV, Wasley LC, Michnick D. 1991. Improved Vectors for Stable Expression of Foreign Genes in Mammalian-Cells by Use of the Untranslated Leader Sequence From Emc Virus. Nucleic Acids Research 19(16):4485-4490.

Kim NS, Kim SJ, Lee GM., Clonal variability within dihydrofoloate reductase-mediated gene amplified chinese hamster ovary cells: stability in the absence of selective pressure. 1998. Biotechnology and Bioengineering 60(6):679-688.

Kim SJ, Kim NS, Ryu CJ, Hong HJ, Lee GM. Characterization of chimeric antibody producing CHO cells in the course of dihydrofolate reductase-mediated gene amplification and their stability in the absence of selective pressure. 1998. Biotechnol Bioeng 58(1):73-84.

Kim, N. S., T. H. Byun, et al. (2001). "Key determinants in the occurrence of clonal variation in humanized antibody expression of CHO cells during dihydrofolate reductase mediated gene amplification." Biotechnology Progress 17(1): 69-75.

Knappskog S, Ravneberg H, Gjerdrum C, Trosse C, Stern B, Pryme IF. 2007. The level of synthesis and secretion of *Gaussia princeps* luciferase in transfected CHO cells is heavily dependent on the choice of signal peptide. Journal of Biotechnology 128(4):705-715.

Kobayashi M, Yamauchi Y, Tanaka A, Shimamura S. 1996. Improved dicistronic mRNA expression vectors for efficient selection of transfectants highly expressing foreign genes. Biotechniques 21(3):398-402.

Kotsopoulou E, Bosteels H, Chim YT, Pegman P, Stephen G, Thornhill SI, Faulkner JD, Uden M. 2010. Optimised mammalian expression through the coupling of codon adaptation with gene amplification: Maximum yields with minimum effort. Journal of Biotechnology 146(4):186-193.

Kozac, Context effects and inefficient initiation at non-AUG codons in eucaryotic cell-free translation systems. Molec Cell Biol. 1989;9:5073-80.

Kwaks TH, Otte AP. 2006. Employing epigenetics to augment the expression of therapeutic proteins in mammalian cells. Trends Biotechnol 24(3):137-42.

Lee CJ, Seth G, Tsukuda J, Hamilton RW. 2009. A clone screening method using mRNA levels to determine specific productivity and product quality for monoclonal antibodies. Biotechnology and Bioengineering 102(4):1107-1118.

Lee JC, Wu TY, Huang CF, Yang FM, Shih SR, Hsu JTA. 2005. High-efficiency protein expression mediated by enterovirus 71 internal ribosome entry. Biotechnology and Bioengineering 90(5):656-662.

Li J, Menzel C, Meier D, Zhang C, Dubel S, Jostock T. 2007. A comparative study of different vector designs for the mammalian expression of recombinant IgG antibodies. J Immunol Methods 318(1-2):113-24.

Li, J. D., C. C. Zhang, et al. (2007). "Analysis of IgG heavy chain to light chain ratio with mutant Encephalomyocarditis virus internal ribosome entry site." Protein Engineering Design & Selection 20(10): 491-496.

Luke, G. A., H. Escuin, et al. (2009). "2A to the fore—Research, technology and applications." Biotechnology and Genetic Engineering Reviews 26: 223-260.

Ma Y, Ramezani A, Lewis R, Hawley RG, Thomson JA. 2003. High-level sustained transgene expression in human embryonic stem cells using lentiviral vectors. Stem Cells 21(1):111-117.

Martin P, Albagli O, Poggi MC, Boulukos KE, Pognonec P. 2006. Development of a new bicistronic retroviral vector with strong IRES activity. BMC Biotechnology 6.

Martinez-Salas E. 1999. Internal ribosome entry site biology and its use in expression vectors. Curr Opin Biotechnol 10(5):458-64.

Mechref and Novotny, Structural investigations of glycoconjugates at high sensitivity. Chemical Reviews, 102(2), 321-369, 2002.

Mountford and Smith, Internal ribosome entry sites and dicistronic RNAs in mammalian transenesis. Trends in Genetics, 11(5), 179-184, 1995.

Murakami, H et al., Random insertion and deletion of arbitrary number of bases for codon-based random mutations of DNAs (2002) Nat. Biotechnol. 20, 76-81.

(56) References Cited

OTHER PUBLICATIONS

Nelson AL, Dhimolea E, Reichert JM., Development trends for human monoclonal antibody therapeutics. 2010. Nat Rev Drug Discov 9(10):767-74.

Ng, SK et al., Application of destabilizing sequences on selection marker for improved recombinant protein productivity in CHO-DG44. 2007. Metabolic Engineering 9(3): 304-316.

Niwa, H et al., Efficient selection for high-expression transfectants with a novel eukaryotic vector. 1991. Gene 108(2): 193-199.

North SJ et al., Glycomics profiling of Chinese hamster ovary cell glycosylation mutants reveals N-glycans of a novel size and complexity. JBC 285(8), 5759-5775, 2010.

Omasa T, Onitsuka M, Kim WD. 2010. Cell engineering and cultivation of chinese hamster ovary (CHO) cells. Curr Pharm Biotechnol 11(3):233-40.

Pikaart MI, Recillas-Targa F, Felsenfeld G. 1998. Loss of transcriptional activity of a transgene is accompanied by DNA methylation and histone deacetylation and is prevented by insulators. Genes & Development 12(18):2852-2862.

Qiao J, Roy V, Girard MH, Caruso M. 2002. High translation efficiency is mediated by the encephalomyocarditis virus internal ribosomal entry sites if the natural sequence surrounding the eleventh AUG is retained. Human Gene Therapy 13(7):881-887.

Raju TS et al., Species-specific variation in glycosylation of IgG: evidence for the species-specific sialylation and branch-specific galactosylation and importance of engineering recombinant glycoprotein therapeutics. Glycobiology, 10(5), 477-486, 2000.

Rees et al., Bistronic vector for the creation of stable mammalian cell lines that predisposes all antibiotic-resistant cells to express recombinant protein. Coote et al. Biotechniques 20(1):102-104, 106, 108-110, 1996.

Reetz MT et al., Addressing the numbers problem in directed evolution. 2008, ChemBioChem, 21;9(11):1797-804.

Rita Costa A, Elisa Rodrigues M, Henriques M, Azeredo J, Oliveira R. 2010. Guidelines to cell engineering for monoclonal antibody production. Eur J Pharm Biopharm 74(2):127-38.

Rudd PM et al., Glycosylation and the immune system. Science. 2001;291(5512): 2370-2376.

Sanchis J et al., Improved PCR method for the creation of saturation mutagenesis libraries in directed evolution: application to difficult-to-amplify templates. Appl. Microbiol. Biotechnol. Nov. 2008; 81(2):387-97.

Sautter K, Enenkel B. 2005. Selection of high-producing CHO cells using NPT selection marker with reduced enzyme activity. Biotechnol Bioeng 89(5):530-8.

Sautter, K and Enenkel, B, Selection of high-producing CHO cells using NPT selection marker with reduced enzyme activity. 2005. Biotechnol Bioeng 89(5): 530-538.

Schlatter S, Stansfield SH, Dinnis DM, Racher AJ, Birch JR, James DC. 2005. On the optimal ratio of heavy to light chain genes for efficient recombinant antibody production by CHO cells. Biotechnol Prog 21(1):122-133.

Senigl H, Plachy J, Hejnar J. 2008. The core element of a CpG island protects avian sarcoma and leukosis virus-derived vectors from transcriptional silencing. Journal of Virology 82(16):7818-7827.

Tones, V., L. Barra, et al. (2010). "A bicistronic lentiviral vector based on the 1D/2A sequence of foot-and-mouth disease virus expresses proteins stoichiometrically." Journal of Biotechnology 146(3): 138-142.

Trichas, G., J. Begbie, et al. (2008). "Use of the viral 2A peptide for bicistronic expression in transgenic mice." BMC Biology 6.

Underhill MF, Smales CM, Naylor LH, Birch JR, James DC. 2007. Transient gene expression levels from multigene expression vectors. Biotechnology Progress 23(2):435-443.

Urlaub and L A Chasin, Isolation of Chinese hamster cell mutants deficient in dihydrofolate reductase activity. Proc. Natl. Acad. Sci. USA, vol. 77, p. 4216-4220, 1980).

Valle G, Besley J & Colman A, Synthesis and secretion of mouse immunoglobulin chains from *Xenopus* oocytes. Nature, vol. 291, p. 338-340, 1981.

Van Berkel PHC et al., N-linked glycosylation is an important parameter for optimal selection of cell lines producing biopharmaceutical human IgG. Biotechnology Progress, 25(1), 244-151, 2009.

Vanhove M, Usherwood YK, Hendershot LM. 2001. Unassembled Ig heavy chains do not cycle from BiP in vivo but require light chains to trigger their release. Immunity 15(1):105-114.

Virnekäs B, Ge L, Plückthun A, Schneider KC, Wellnhofer G, Moroney SE., Trinucleotide phosphoramidites: ideal reagents for the synthesis of mixed oligonucleotides for random mutagenesis. (1994). Nucleic Acids Res 22, 5600-5607.

Wada Y et al., Comparison of the methods for profiling glycoprotein glycans—HUPO human disease glycomics/proteome intitiative multi-institutional study. Glycobiology, 17(4):411-422,2007.

Wang, L. et al., Expanding the genetic code of *Escherichia coli*. (2001) Science 292, 498-500.

Wang, L., and Schultz, P.G., Expanding the genetic code. (2002) Chem. Comm 1, 1-11.

Westwood, AD et al., Improved recombinant protein yield using a codon deoptimized DHFR selectable marker in a CHEF1 expression plasmid. 2010. Biotechnology Progress 26(6): 1558-1566.

Williams S, Mustoe T, Mulcahy T, Griffiths M, Simpson D, Antoniou M, Irvine A, Mountain A, Crombie R. 2005. CpG-island fragments from the HNRPA2B1/CBX3 genomic locus reduce silencing and enhance transgene expression from the hCMV promoter/enhancer in mammalian cells. Bmc Biotechnology 5.

Wilson C, Bellen HJ, Gehring WJ. 1990. Position effects on eukaryotic gene expression. Annu Rev Cell Biol 6:679-714.

Wurm FM. Production of recombinant protein therapeutics in cultivated mammalian cells. 2004. Nat Biotechnol 22(11):1393-8.

Yahata K, Kishine H, Sone T, Sasaki Y, Hotta J, Chesnut JD, Okabe M, Imamoto F. 2005. Multi-gene Gateway clone design for expression of multiple heterologous genes in living cells: Conditional gene expression at near physiological levels. Journal of Biotechnology 118(2):123-134.

Yang Y, Mariati, Chusainow J, Yap MG. 2010. DNA methylation contributes to loss in productivity of monoclonal antibody-producing CHO cell lines. J Biotechnol 147(3-4):180-5.

Yang YS et al., Mutated polyadenylation signals for controlling expression levels of multiple genes in mammalian cells. Biotech and Bioeng, 102(4):1152-1160, 2009.

Yenofsky, RL et al., A mutant neomycin phosphotransferase II gene reduces the resistance of transformant to antibiotic selection pressure. 1990. PNAS. 87(9): 3435-3439.

Zaccolo et al., An approach to random mutagenesis of DNA using mixtures of triphosphate derivatives of nucloeside anologues. (1996) J. Mol. Biol. 255, 589-603.

\* cited by examiner

FIGURES

```
                  10        11        12
IRESwt    AAAACACGATGATAATATGGCCACAACCATG                         SEQ ID NO: 113

IRESatt   AAAACACGATGATAAGCTTGCCACAACCCCGGGAGATGAGGATCGTTTCGCATG   SEQ ID NO: 114
                         *
mIRES1    AAATCGATGTGATAATATGGCCGCAACCATG = IRES V1      SEQ ID NO: 18
                   *
mIRES2    AAATCGATATGATAATATGGCCGCAACCGTG = IRES V3      SEQ ID NO: 19
                              *
mIRES3    AAATCGATATGATAATGTGGCCGCAACCATG = IRES V5      SEQ ID NO: 20
                              *
mIRES4    AAATCGATGTGATAATATGGCCGCAACCGTG                SEQ ID NO: 21
                                        *
mIRES5    AAATCGATGTGATAATGTGGCCGCAACCATG = IRES V6      SEQ ID NO: 22
                              *
mIRES6    AAATCGATATGATAATGTGGCCGCAACCGTG                SEQ ID NO: 23
                                        *
mIRES7    AAATCGATGTGATAATGTGGCCGCAACCGTG                SEQ ID NO: 24
                                        *
mIRES8    AAATCGATATGATAATATG                            SEQ ID NO: 25
                   *
mIRES9    AAATCGATATGATAATGTG = IRES V19                 SEQ ID NO: 26
                         *
mIRES10   AAATCGATGTGATAATGTG                            SEQ ID NO: 27
                         *
mIRES11   AAATCGATATG                                    SEQ ID NO: 28
                   *
mIRES12   AAATCGATGTG = IRES V20                         SEQ ID NO: 29
                *
IRES V2   AAATCGATATGATAATATG                            SEQ ID NO: 83
                   *
IRES V4   AAATCGATGTGATAATATGGCCGCAACCGTG                SEQ ID NO: 84
                                        *
IRES V7   AAATCGATATG                                    SEQ ID NO: 85
                *
IRES V8   AAATCGATCTGATAATCTGGCCGCAACCCTG                SEQ ID NO: 86
                                        *
IRES V9   AAATCGATATGATAATCTGGCCGCAACCCTG                SEQ ID NO: 87
                                        *
IRES V10  AAATCGATACGATAATACGGCCGCAACCACG                SEQ ID NO: 88
                                        *
IRES V11  AAATCGATGTGATAATGTGGCCGCAACCGTG                SEQ ID NO: 89
                                        *
IRES V12  AAATCGATATGATAATACGGCCGCAACCACG                SEQ ID NO: 90
                                        *
IRES V13  AAATCGATATAATAATATAGCCGCAACCATA                SEQ ID NO: 91
                                        *
IRES V14  AAATCGATATGATAATGTGGCCGCAACCGTG                SEQ ID NO: 92
                                        *
IRES V15  AAATCGATATGATAATATAGCCGCAACCATA                SEQ ID NO: 93
                                        *
IRES V16  AAATCGATTTGATAATTTGGCCGCAACCTTG                SEQ ID NO: 94
                                        *
IRES V17  AAATCGATGTGATAATGTG                            SEQ ID NO: 95
                         *
IRES V18  AAATCGATATGATAATTTGGCCGCAACCTTG                SEQ ID NO: 96
                                        *
IRES V20  AAATCGATGTG                                    SEQ ID NO: 29
                *
```

FIG. 1C

|  |  | 10th | 11th | 12th |  |
|---|---|---|---|---|---|
| | IRES0, WT | AAAACACGATGATAATATGGCCACAACCATG | | | SEQ ID NO: 113 |
| (Commercial) | IRESatt1 | AAAACACGATGATAAGCTTGCCACAACC...(23bases).....ATG | | | SEQ ID NO: 2 |
| | IRESatt2 | AAAACACGGTGATAATATGGCCACAACCATG | | | SEQ ID NO: 11 |
| | IRESatt3 | AAAACACGATGATAATGTGGCCACAACCATG | | | SEQ ID NO: 12 |
| | IRESatt4 | AAAACACGATGATAATATGGCCACAACCGTG | | | SEQ ID NO: 13 |
| | IRESatt5 | AAAACACGGTGATAATGTGGCCACAACCATG | | | SEQ ID NO: 14 |
| | IRESatt6 | AAAACACGGTGATAATATGGCCACAACCGTG | | | SEQ ID NO: 15 |
| | IRESatt7 | AAAACACGATGATAATGTGGCCACAACCGTG | | | SEQ ID NO: 16 |
| | IRESatt8 | AAAACACGGTGATAATGTGGCCACAACCGTG | | | SEQ ID NO: 17 |

FIG. 1D

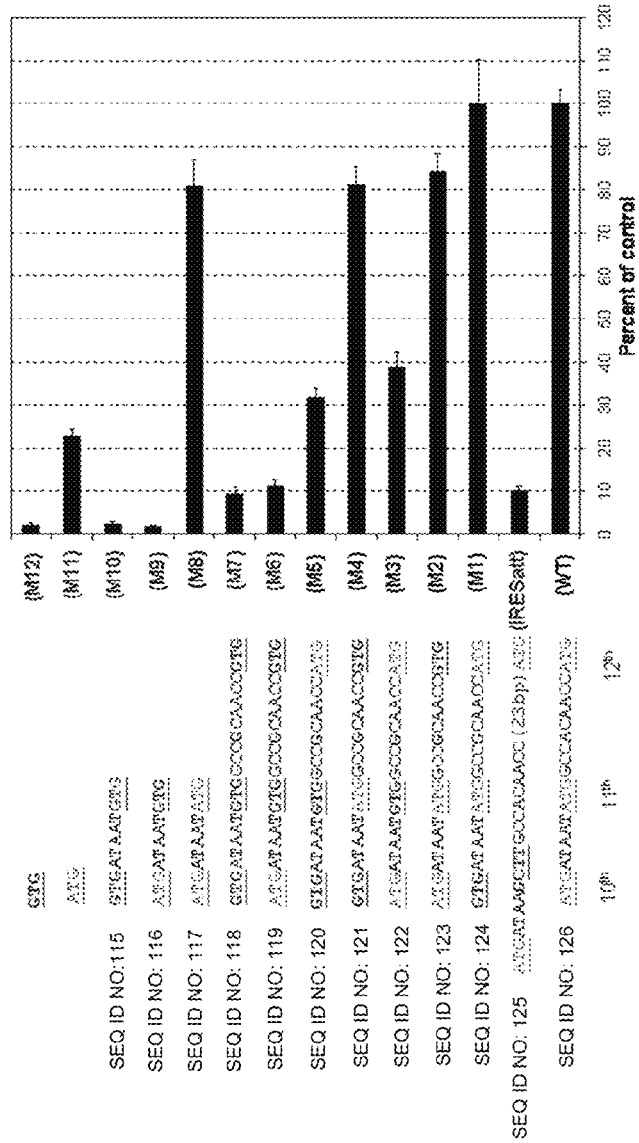

FIG. 2A

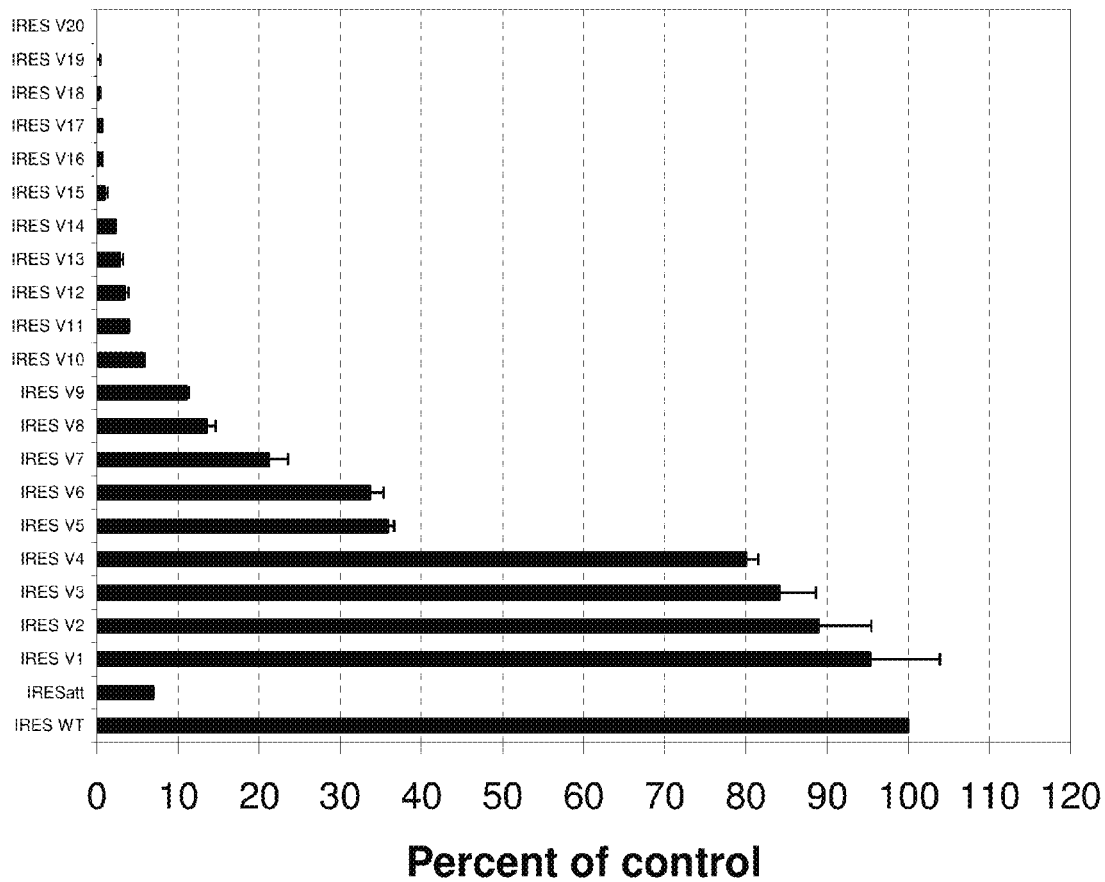

FIG. 2B

Sequence of EMCV IRES

CCCCTCTCCCTCCCCCCCCCCTAACGTTACTGGCCGAAGCCGCTTGGAATAAGGCCGGTGTG
CGTTTGTCTATATGTTATTTTCCACCATATTGCCGTCTTTTGGCAATGTGAGGGCCCGGAAA
CCTGGCCCTGTCTTCTTGACGAGCATTCCTAGGGGTCTTTCCCCTCTCGCCAAAGGAATGCA
AGGTCTGTTGAATGTCGTGAAGGAAGCAGTTCCTCTGGAAGCTTCTTGAAGACAAACAACGT
CTGTAGCGACCCTTTGCAGGCAGCGGAACCCCCCACCTGGCGACAGGTGCCTCTGCGGCCAA
AAGCCACGTGTATAAGATACACCTGCAAAGGCGGCACAACCCCAGTGCCACGTTGTGAGTTG
GATAGTTGTGGAAAGAGTCAAATGGCTCTCCTCAAGCGTATTCAACAAGGGGCTGAAGGATG
CCCAGAAGGTACCCCATTGTATGGGATCTGATCTGGGGCCTCGGTGCACATGCTTTACGTGT
GTTTAGTCGAGGTTAAAAAACGTCTAGGCCCCCGAACCACGGGGACGTGGTTTTCCTTTGA
AAAACACGATGATAATATGGCCACAACCATG   SEQ ID NO: 1

FIG. 3

(A) Co-transfection
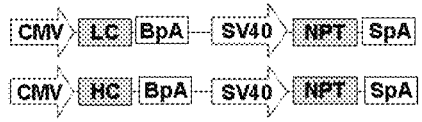
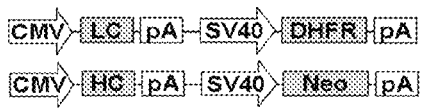
(B) Multi-promoter
(C) Tricistronic
```
              10       11           12
IRESwt    ATGATAATATGGCCACAACCATG       SEQ ID NO: 126
              10                                         NPT
IRESatt   ATGATAAGCTTGCCACAACCCCGGGAGATGAGGATCGTTTCGCATG
                                                   SEQ ID NO: 125
```
FIG. 4
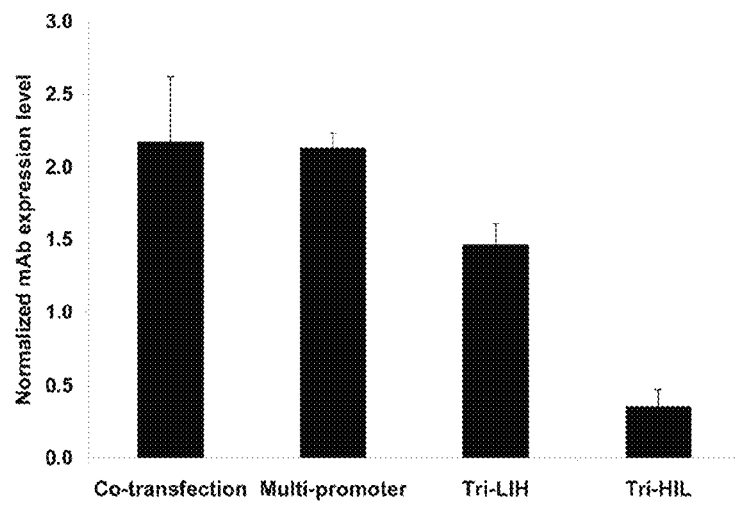
FIG. 5

|  | Co-transfection | Multi-promoter | Tri-LIH |
|---|---|---|---|
| Highest qmAb | 0.07 | 0.09 | 1.16 |
| Expressing clones% | 40 | 60 | 75 |

(A) Co-transfection
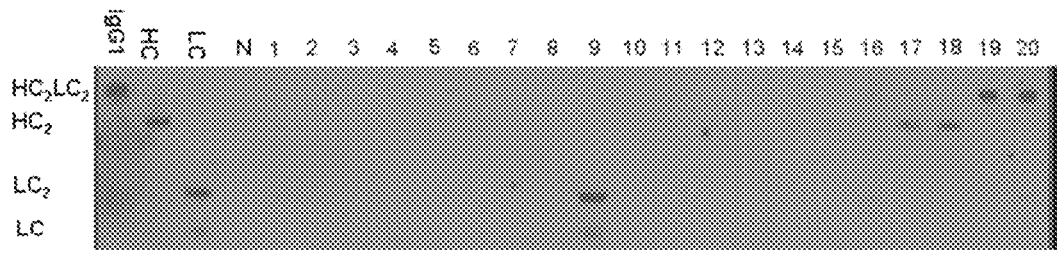
(B) Multi-promoter
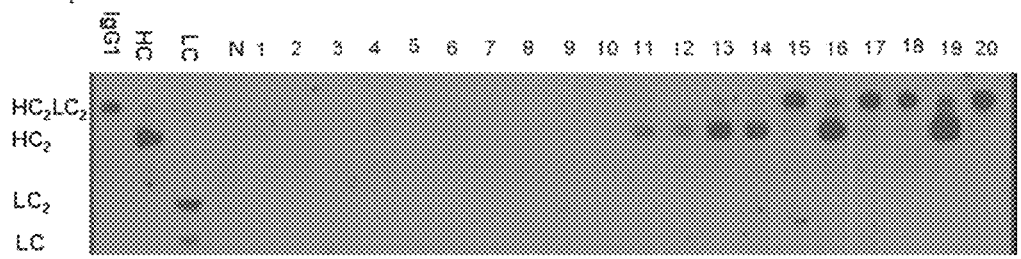
(C) Tri-LIH
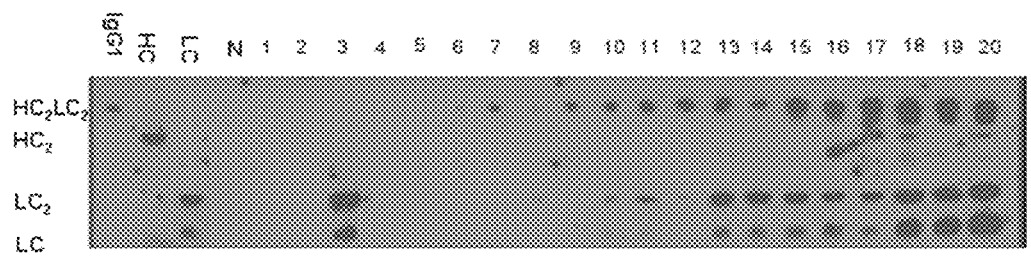
FIG. 7
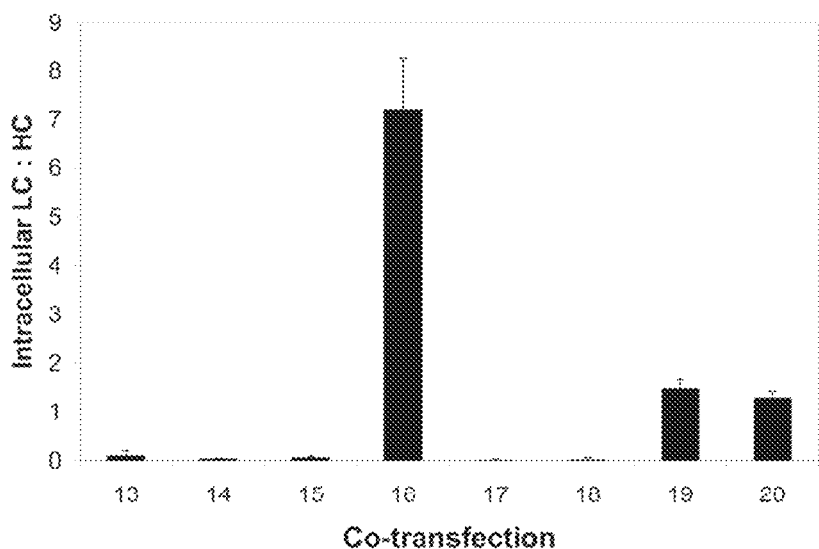
FIG. 8A

| Name | AA change | Nucleotide change | Strength% |
|---|---|---|---|
| WT | | | 100 |
| M1[a] | E182D | GAG to GAT | 22% |
| M10[a] | D261G | GAC to GGC | 3% |
| M4[b] | M001L and D261G | ATG to TTG and GAC to GGC | <0.15% |

| | WT | M1 | M10 |
|---|---|---|---|
| Amino acid substitution | None | E182D | D261G |
| Activity% | 100 | 22 | 3 |

Light scattering

1. Complete IgG control
2. HC$_2$ control
3. LC$_2$ and LC control
4. Blank control
5. LIHID
6. DILIH
7. HILID ately one IRES sequence, wherein the at least one IRES sequence is located between the at least one nucleic acid sequence encoding for the peptide or protein of interest and the at least one nucleic acid sequence encoding for the selectable marker, and the at least one nucleic acid sequence encoding for a selectable marker has a reduced translation efficiency and/or the encoded selectable marker is mutated such that it has a lowered activity compared to its

SEQUENCE LISTING

```
<160> NUMBER OF SEQ ID NOS: 126

<210> SEQ ID NO 1
<211> LENGTH: 589
<212> TYPE: DNA
<213> ORGANISM: encephalomyocarditis virus

<400> SEQUENCE: 1 ccctctccc tcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt ctttcccctc tcgccaaagg    180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa aacacgatga taatatggcc acaaccatg                 589

<210> SEQ ID NO 2
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 2
aaaacacgat gataagcttg ccacaaccc gggagatgag gatcgtttcg catg              54

<210> SEQ ID NO 3
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 3
aaaacacgdt gataatdtgg ccacaaccdt g                                     31

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t

<400> SEQUENCE: 4
```
aaaacacgat nataatdtgg ccacaaccdt g                                    31

<210> SEQ ID NO 5
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: n is a, c, g, or t

<400> SEQUENCE: 5
aaaacacgdt gataatatng ccacaaccdt g                                    31

<210> SEQ ID NO 6
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: n is a, c, g, or t

<400> SEQUENCE: 6
aaaacacgdt gataatdtgg ccacaaccat n                                    31

<210> SEQ ID NO 7
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 7
aaaacacgat nataatatng ccacaaccdt g                                    31

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 8
aaaacacgdt gataatatng ccacaaccat n                                    31

<210> SEQ ID NO 9
<211> LENGTH: 31
<212> TYPE: DNA

<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 9
aaaacacgat nataatdtgg ccacaaccat n        31

<210> SEQ ID NO 10
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 10
aaaacacgat nataatatng ccacaaccat n        31

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 11
aaaacacggt gataatatgg ccacaaccat g        31

<210> SEQ ID NO 12
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 12
aaaacacgat gataatgtgg ccacaaccat g        31

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 13
aaaacacgat gataatatgg ccacaaccgt g        31

<210> SEQ ID NO 14
<211> LENGTH: 31

```
<212> TYPE: DNA
<213> ORGANISM: Artificial Sequence
<220> FEATURE:
<223> OTHER INFORMATION: Synthetic oligonucleotide

<400> SEQUENCE: 14
aaaacacggt gataatgtgg ccacaaccat g                              31

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 15
aaaacacggt gataatatgg ccacaaccgt g                              31

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 16
aaaacacgat nataatdtgg ccacaaccat n                              31

<210> SEQ ID NO 17
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 17
aaaacacggt gataatgtgg ccacaaccgt g                              31

<210> SEQ ID NO 18
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 18
aaatcgatgt gataatatgg ccgcaaccat g                              31

<210> SEQ ID NO 19
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 19
aaatcgatat gataatatgg ccgcaaccgt g                              31

<210> SEQ ID NO 20
```

```
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 20
aaatcgatat gataatgtgg ccgcaaccat g                              31

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 21
aaatcgatgt gataatatgg ccgcaaccgt g                              31

<210> SEQ ID NO 22
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 22
aaatcgatgt gataatgtgg ccgcaaccat g                              31

<210> SEQ ID NO 23
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 23
aaatcgatat gataatgtgg ccgcaaccgt g                              31

<210> SEQ ID NO 24
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 24
aaatcgatgt gataatgtgg ccgcaaccgt g                              31

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
aaatcgatat gataatatg                                            19

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
```

```
aaatcgatat gataatgtg                                              19

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
aaatcgatgt gataatgtg                                              19

<210> SEQ ID NO 28
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 28
aaatcgatat g                                                      11

<210> SEQ ID NO 29
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 29
aaatcgatgt g                                                      11

<210> SEQ ID NO 30
<211> LENGTH: 612
<212> TYPE: DNA
<213> ORGANISM: Artificial Sequence
<220> FEATURE:
<223> OTHER INFORMATION: Synthetic oligonucleotide

<400> SEQUENCE: 30
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggg cttttccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtaccccca ttgtatggga tctgatctgg ggcctcggtg     480
cacatgcttt acgtgtgttt agtcgaggtt aaaaaacgtc taggcccccc gaaccacggg     540
gacgtggttt cctttgaaa aacacgatga taagcttgcc acaaccccgg gagatgagga     600
tcgtttcgca tg                                                        612

<210> SEQ ID NO 31
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
```

<221> NAME/KEY: misc_feature
<222> LOCATION: (1)..(589)
<223> OTHER INFORMATION: at least one d is not a

<400> SEQUENCE: 31

```
ccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctagggt cttccctc tcgccaaagg    180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtaccca ttgtatggga tctgatctgg ggcctcggtg    480
cacatgcttt acgtgtgttt agtcgaggtt aaaaaacgtc taggcccccc gaaccacggg   540
gacgtggttt tcctttgaaa aacacgdtga taatdtggcc acaaccdtg               589
```

<210> SEQ ID NO 32
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one d is not a or n is not g
<220> FEATURE:
<221> NAME/KEY: misc_feature
<222> LOCATION: (569)..(569)
<223> OTHER INFORMATION: n is a, c, g, or t

<400> SEQUENCE: 32

```
ccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctagggt cttccctc tcgccaaagg    180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtaccca ttgtatggga tctgatctgg ggcctcggtg    480
cacatgcttt acgtgtgttt agtcgaggtt aaaaaacgtc taggcccccc gaaccacggg   540
gacgtggttt tcctttgaaa aacacgatna taatdtggcc acaaccdtg               589
```

<210> SEQ ID NO 33
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one d is not a or n is not g
<220> FEATURE:
<221> NAME/KEY: misc_feature
<222> LOCATION: (577)..(577)
<223> OTHER INFORMATION: n is a, c, g, or t

<400> SEQUENCE: 33

```
cccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttccctc tcgccaaagg    180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtaccccca ttgtatggga tctgatctgg ggcctcggtg   480
cacatgcttt acgtgtgttt agtcgaggtt aaaaaacgtc taggccccccc gaaccacggg   540
gacgtggttt tcctttgaaa aacacgdtga taatatngcc acaaccdtg             589
```

<210> SEQ ID NO 34
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one d is not a or n is not g
<220> FEATURE:
<221> NAME/KEY: misc_feature
<222> LOCATION: (589)..(589)
<223> OTHER INFORMATION: n is a, c, g, or t

<400> SEQUENCE: 34

```
cccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttccctc tcgccaaagg    180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtaccccca ttgtatggga tctgatctgg ggcctcggtg   480
cacatgcttt acgtgtgttt agtcgaggtt aaaaaacgtc taggccccccc gaaccacggg   540
gacgtggttt tcctttgaaa aacacgdtga taatdtggcc acaaccatn              589
```

<210> SEQ ID NO 35
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one n is not g or d is not a
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (577)..(577)

<223> OTHER INFORMATION: n is a, c, g, or t

<400> SEQUENCE: 35

| ccctctccc | tccccccccc | ctaacgttac | tggccgaagc | cgcttggaat | aaggccggtg | 60 |
| tgcgtttgtc | tatatgttat | tttccaccat | attgccgtct | tttggcaatg | tgagggcccg | 120 |
| gaaacctggc | cctgtcttct | tgacgagcat | tcctaggggt | cttccctc | tcgccaaagg | 180 |
| aatgcaaggt | ctgttgaatg | tcgtgaagga | agcagttcct | ctggaagctt | cttgaagaca | 240 |
| aacaacgtct | gtagcgaccc | tttgcaggca | gcggaacccc | ccacctggcg | acaggtgcct | 300 |
| ctgcggccaa | aagccacgtg | tataagatac | acctgcaaag | gcggcacaac | cccagtgcca | 360 |
| cgttgtgagt | tggatagttg | tggaaagagt | caaatggctc | tcctcaagcg | tattcaacaa | 420 |
| ggggctgaag | gatgcccaga | aggtacccca | ttgtatggga | tctgatctgg | ggcctcggtg | 480 |
| cacatgcttt | acgtgtgttt | agtcgaggtt | aaaaaacgtc | taggcccccc | gaaccacggg | 540 |
| gacgtggttt | tcctttgaaa | aacacgatna | taatatngcc | acaaccdtg | | 589 |

<210> SEQ ID NO 36
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t

<400> SEQUENCE: 36

| ccctctccc | tccccccccc | ctaacgttac | tggccgaagc | cgcttggaat | aaggccggtg | 60 |
| tgcgtttgtc | tatatgttat | tttccaccat | attgccgtct | tttggcaatg | tgagggcccg | 120 |
| gaaacctggc | cctgtcttct | tgacgagcat | tcctaggggt | cttccctc | tcgccaaagg | 180 |
| aatgcaaggt | ctgttgaatg | tcgtgaagga | agcagttcct | ctggaagctt | cttgaagaca | 240 |
| aacaacgtct | gtagcgaccc | tttgcaggca | gcggaacccc | ccacctggcg | acaggtgcct | 300 |
| ctgcggccaa | aagccacgtg | tataagatac | acctgcaaag | gcggcacaac | cccagtgcca | 360 |
| cgttgtgagt | tggatagttg | tggaaagagt | caaatggctc | tcctcaagcg | tattcaacaa | 420 |
| ggggctgaag | gatgcccaga | aggtacccca | ttgtatggga | tctgatctgg | ggcctcggtg | 480 |
| cacatgcttt | acgtgtgttt | agtcgaggtt | aaaaaacgtc | taggcccccc | gaaccacggg | 540 |
| gacgtggttt | tcctttgaaa | aacacgdtga | taatatngcc | acaaccatn | | 589 |

<210> SEQ ID NO 37
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one n is not g or d is not a
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature

```
<222> LOCATION: (589)..(589)
<223> OTHER INFORMATION: n is a, c, g, or t

<400> SEQUENCE: 37
cccctctccc tcccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctagggggt cttttcccctc tcgccaaagg    180 aatgcaaggt ctgttgaatg tcgtgaagga agcagttcct ctggaagctt cttgaagaca     240
aacaacgtct gtagcgaccc tttgcaggca gcggaaccc ccacctggcg acaggtgcct      300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa aacacgatna taatdtggcc acaaccatn                 589

<210> SEQ ID NO 38
<211> LENGTH: 589
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(589)
<223> OTHER INFORMATION: at least one n is not g
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t

<400> SEQUENCE: 38 ccctctccc tccccccccc ctaacgttac tggccgaagc cgcttggaat aaggccggtg       60
tgcgtttgtc tatatgttat tttccaccat attgccgtct tttggcaatg tgagggcccg    120
gaaacctggc cctgtcttct tgacgagcat tcctagggggt cttttcccctc tcgccaaagg   180 aatgcaaggt ctgttgaatg tcgtgaagga agcagttcct ctggaagctt cttgaagaca    240
aacaacgtct gtagcgaccc tttgcaggca gcggaaccc ccacctggcg acaggtgcct     300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acgtgtgttt agtcgaggtt aaaaaacgtc taggcccccc gaaccacggg   540
gacgtggttt tcctttgaaa aacacgatna taatatngcc acaaccatn                589

<210> SEQ ID NO 39
<211> LENGTH: 589
<212> TYPE: DNA
<213> ORGANISM: Artificial Sequence
<220> FEATURE:
<223> OTHER INFORMATION: attenuated IRES sequence
```

<400> SEQUENCE: 39

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat cctagggggt cttcccctc tcgccaaagg     180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa aacacggtga taatatggcc acaaccatg                589
```

<210> SEQ ID NO 40
<211> LENGTH: 589
<212> TYPE: DNA
<213> ORGANISM: Artificial Sequence
<220> FEATURE:
<223> OTHER INFORMATION: attenuated IRES sequence

<400> SEQUENCE: 40

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat cctagggggt cttcccctc tcgccaaagg     180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa aacacgatga taatgtggcc acaaccatg                 589
```

<210> SEQ ID NO 41
<211> LENGTH: 589
<212> TYPE: DNA
<213> ORGANISM: Artificial Sequence
<220> FEATURE:
<223> OTHER INFORMATION: attenuated IRES sequece

<400> SEQUENCE: 41

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat cctagggggt cttcccctc tcgccaaagg     180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
```

```
gacgtggttt cctttgaaa aacacgatga taatatggcc acaaccgtg        589
```

```
<210> SEQ ID NO 42
<211> LENGTH: 589
<212> TYPE: DNA
<213> ORGANISM: Artificial Sequence
<220> FEATURE:
<223> OTHER INFORMATION: attenuated IRES sequence

<400> SEQUENCE: 42
cccctctccc tcccccccc ctaacgttac tggccgaagc cgcttggaat aaggccggtg         60
tgcgtttgtc tatatgttat tttccaccat attgccgtct tttggcaatg tgagggcccg        120
gaaacctggc cctgtcttct tgacgagcat cctaggggt cttccctc tcgccaaagg          180
aatgcaaggt ctgttgaatg tcgtgaagga agcagttcct ctggaagctt cttgaagaca        240
aacaacgtct gtagcgaccc tttgcaggca gcggaacccc ccacctggcg acaggtgcct        300
ctgcggccaa agccacgtg tataagatac acctgcaaag gcggcacaac cccagtgcca         360
cgttgtgagt tggatagttg tggaaagagt caaatggctc tcctcaagcg tattcaacaa        420
ggggctgaag gatgcccaga aggtacccca ttgtatggga tctgatctgg ggcctcggtg        480
cacatgcttt acgtgtgttt agtcgaggtt aaaaaacgtc taggccccc gaaccacggg         540
gacgtggttt cctttgaaa aacacggtga taatgtggcc acaaccatg                     589
```

```
<210> SEQ ID NO 43
<211> LENGTH: 589
<212> TYPE: DNA
<213> ORGANISM: Artificial Sequence
<220> FEATURE:
<223> OTHER INFORMATION: attenuated IRES sequence

<400> SEQUENCE: 43
cccctctccc tcccccccc ctaacgttac tggccgaagc cgcttggaat aaggccggtg         60
tgcgtttgtc tatatgttat tttccaccat attgccgtct tttggcaatg tgagggcccg        120
gaaacctggc cctgtcttct tgacgagcat cctaggggt cttccctc tcgccaaagg          180
aatgcaaggt ctgttgaatg tcgtgaagga agcagttcct ctggaagctt cttgaagaca        240
aacaacgtct gtagcgaccc tttgcaggca gcggaacccc ccacctggcg acaggtgcct        300
ctgcggccaa agccacgtg tataagatac acctgcaaag gcggcacaac cccagtgcca         360
cgttgtgagt tggatagttg tggaaagagt caaatggctc tcctcaagcg tattcaacaa        420
ggggctgaag gatgcccaga aggtacccca ttgtatggga tctgatctgg ggcctcggtg        480
cacatgcttt acgtgtgttt agtcgaggtt aaaaaacgtc taggccccc gaaccacggg         540
gacgtggttt cctttgaaa aacacggtga taatatggcc acaaccgtg                     589
```

```
<210> SEQ ID NO 44
<211> LENGTH: 589
<212> TYPE: DNA
<213> ORGANISM: Artificial Sequence
<220> FEATURE:
<223> OTHER INFORMATION: attenuated IRES sequence

<400> SEQUENCE: 44
cccctctccc tcccccccc ctaacgttac tggccgaagc cgcttggaat aaggccggtg         60
tgcgtttgtc tatatgttat tttccaccat attgccgtct tttggcaatg tgagggcccg        120
gaaacctggc cctgtcttct tgacgagcat cctaggggt cttccctc tcgccaaagg          180
```

```
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt cctttgaaa aacacgatga taatgtggcc acaaccgtg               589
```

<210> SEQ ID NO 45
<211> LENGTH: 589
<212> TYPE: DNA
<213> ORGANISM: Artificial Sequence
<220> FEATURE:
<223> OTHER INFORMATION: attenuated IRES sequence

<400> SEQUENCE: 45

```
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt ctttcccctc tcgccaaagg    180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt cctttgaaa aacacggtga taatgtggcc acaaccgtg                589
```

<210> SEQ ID NO 46
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 46

```
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt ctttcccctc tcgccaaagg    180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt cctttgaaa atcgatgtga taatatggcc gcaaccatg                589
```

<210> SEQ ID NO 47
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 47

```
ccoctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttccccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acgtgtgttt agtcgaggtt aaaaaacgtc taggcccccc gaaccacggg   540
gacgtggttt tcctttgaaa atcgatatga taatatggcc gcaaccgtg              589
```

<210> SEQ ID NO 48
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 48

```
ccoctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttccccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acgtgtgttt agtcgaggtt aaaaaacgtc taggcccccc gaaccacggg   540
gacgtggttt tcctttgaaa atcgatatga taatgtggcc gcaaccatg              589
```

<210> SEQ ID NO 49
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 49

```
ccoctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttccccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
```

| | |
|---|---|
| ggggctgaag gatgcccaga aggtaccca ttgtatggga tctgatctgg ggcctcggtg | 480 |
| cacatgcttt acgtgtgttt agtcgaggtt aaaaaacgtc taggccccc gaaccacggg | 540 |
| gacgtggttt tcctttgaaa atcgatgtga taatatggcc gcaaccgtg | 589 |

<210> SEQ ID NO 50
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 50

| | |
|---|---|
| cccctctccc tcccccccc ctaacgttac tggccgaagc cgcttggaat aaggccggtg | 60 |
| tgcgtttgtc tatatgttat tttccaccat attgccgtct tttggcaatg tgagggcccg | 120 |
| gaaacctggc cctgtcttct tgacgagcat cctagggggt cttttccctc tcgccaaagg | 180 |
| aatgcaaggt ctgttgaatg tcgtgaagga agcagttcct ctggaagctt cttgaagaca | 240 |
| aacaacgtct gtagcgaccc tttgcaggca gcggaacccc ccacctggcg acaggtgcct | 300 |
| ctgcggccaa aagccacgtg tataagatac acctgcaaag gcggcacaac cccagtgcca | 360 |
| cgttgtgagt tggatagttg tggaaagagt caaatggctc tcctcaagcg tattcaacaa | 420 |
| ggggctgaag gatgcccaga aggtaccca ttgtatggga tctgatctgg ggcctcggtg | 480 |
| cacatgcttt acgtgtgttt agtcgaggtt aaaaaacgtc taggccccc gaaccacggg | 540 |
| gacgtggttt tcctttgaaa atcgatgtga taatgtggcc gcaaccatg | 589 |

<210> SEQ ID NO 51
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 51

| | |
|---|---|
| cccctctccc tcccccccc ctaacgttac tggccgaagc cgcttggaat aaggccggtg | 60 |
| tgcgtttgtc tatatgttat tttccaccat attgccgtct tttggcaatg tgagggcccg | 120 |
| gaaacctggc cctgtcttct tgacgagcat cctagggggt cttttccctc tcgccaaagg | 180 |
| aatgcaaggt ctgttgaatg tcgtgaagga agcagttcct ctggaagctt cttgaagaca | 240 |
| aacaacgtct gtagcgaccc tttgcaggca gcggaacccc ccacctggcg acaggtgcct | 300 |
| ctgcggccaa aagccacgtg tataagatac acctgcaaag gcggcacaac cccagtgcca | 360 |
| cgttgtgagt tggatagttg tggaaagagt caaatggctc tcctcaagcg tattcaacaa | 420 |
| ggggctgaag gatgcccaga aggtaccca ttgtatggga tctgatctgg ggcctcggtg | 480 |
| cacatgcttt acgtgtgttt agtcgaggtt aaaaaacgtc taggccccc gaaccacggg | 540 |
| gacgtggttt tcctttgaaa atcgatatga taatgtggcc gcaaccgtg | 589 |

<210> SEQ ID NO 52
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 52

| | |
|---|---|
| cccctctccc tcccccccc ctaacgttac tggccgaagc cgcttggaat aaggccggtg | 60 |
| tgcgtttgtc tatatgttat tttccaccat attgccgtct tttggcaatg tgagggcccg | 120 |

```
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240
aacaacgtct gtagcgaccc tttgcaggca gcggaacccc ccacctggcg acaggtgcct      300
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtacccca ttgtatggga tctgatctgg ggcctcggtg      480
cacatgcttt acgtgtgttt agtcgaggtt aaaaaacgtc taggcccccc gaaccacggg      540
gacgtggttt tcctttgaaa atcgatgtga taatgtggcc gcaaccgtg                  589
```

```
<210> SEQ ID NO 53
<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 53
```

```
cccctctccc tcccccccccc ctaacgttac tggccgaagc cgcttggaat aaggccggtg       60
tgcgtttgtc tatatgttat tttccaccat attgccgtct tttggcaatg tgagggcccg      120
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240
aacaacgtct gtagcgaccc tttgcaggca gcggaacccc ccacctggcg acaggtgcct      300
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtacccca ttgtatggga tctgatctgg ggcctcggtg      480
cacatgcttt acgtgtgttt agtcgaggtt aaaaaacgtc taggcccccc gaaccacggg      540
gacgtggttt tcctttgaaa atcgatatga taatatg                               577
```

```
<210> SEQ ID NO 54
<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 54
```

```
cccctctccc tcccccccccc ctaacgttac tggccgaagc cgcttggaat aaggccggtg       60
tgcgtttgtc tatatgttat tttccaccat attgccgtct tttggcaatg tgagggcccg      120
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240
aacaacgtct gtagcgaccc tttgcaggca gcggaacccc ccacctggcg acaggtgcct      300
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtacccca ttgtatggga tctgatctgg ggcctcggtg      480
cacatgcttt acgtgtgttt agtcgaggtt aaaaaacgtc taggcccccc gaaccacggg      540
gacgtggttt tcctttgaaa atcgatatga taatgtg                               577
```

```
<210> SEQ ID NO 55
```

<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 55

| | | | | | | |
|---|---|---|---|---|---|---|
| ccctctccc | tcccccccc | ctaacgttac | tggccgaagc | cgcttggaat | aaggccggtg | 60 |
| tgcgtttgtc | tatatgttat | tttccaccat | attgccgtct | tttggcaatg | tgagggcccg | 120 |
| gaaacctggc | cctgtcttct | tgacgagcat | tcctaggggt | ctttcccctc | tcgccaaagg | 180 |
| aatgcaaggt | ctgttgaatg | tcgtgaagga | agcagttcct | ctggaagctt | cttgaagaca | 240 |
| aacaacgtct | gtagcgaccc | tttgcaggca | gcggaacccc | ccacctggcg | acaggtgcct | 300 |
| ctgcggccaa | aagccacgtg | tataagatac | acctgcaaag | gcggcacaac | cccagtgcca | 360 |
| cgttgtgagt | tggatagttg | tggaaagagt | caaatggctc | tcctcaagcg | tattcaacaa | 420 |
| ggggctgaag | gatgcccaga | aggtacccca | ttgtatggga | tctgatctgg | ggcctcggtg | 480 |
| cacatgcttt | acgtgtgttt | agtcgaggtt | aaaaaacgtc | taggcccccc | gaaccacggg | 540 |
| gacgtggttt | tcctttgaaa | atcgatgtga | taatgtg | | | 577 |

<210> SEQ ID NO 56
<211> LENGTH: 569
<212> TYPE: DNA
<213> ORGANISM: Artificial Sequence
<220> FEATURE:
<223> OTHER INFORMATION: Synthetic oligonucleotide

<400> SEQUENCE: 56

| | | | | | | |
|---|---|---|---|---|---|---|
| ccctctccc | tcccccccc | ctaacgttac | tggccgaagc | cgcttggaat | aaggccggtg | 60 |
| tgcgtttgtc | tatatgttat | tttccaccat | attgccgtct | tttggcaatg | tgagggcccg | 120 |
| gaaacctggc | cctgtcttct | tgacgagcat | tcctaggggt | ctttcccctc | tcgccaaagg | 180 |
| aatgcaaggt | ctgttgaatg | tcgtgaagga | agcagttcct | ctggaagctt | cttgaagaca | 240 |
| aacaacgtct | gtagcgaccc | tttgcaggca | gcggaacccc | ccacctggcg | acaggtgcct | 300 |
| ctgcggccaa | aagccacgtg | tataagatac | acctgcaaag | gcggcacaac | cccagtgcca | 360 |
| cgttgtgagt | tggatagttg | tggaaagagt | caaatggctc | tcctcaagcg | tattcaacaa | 420 |
| ggggctgaag | gatgcccaga | aggtacccca | ttgtatggga | tctgatctgg | ggcctcggtg | 480 |
| cacatgcttt | acgtgtgttt | agtcgaggtt | aaaaaacgtc | taggcccccc | gaaccacggg | 540 |
| gacgtggttt | tcctttgaaa | atcgatatg | | | | 569 |

<210> SEQ ID NO 57
<211> LENGTH: 569
<212> TYPE: DNA
<213> ORGANISM: Artificial Sequence
<220> FEATURE:
<223> OTHER INFORMATION: Synthetic oligonucleotide

<400> SEQUENCE: 57

| | | | | | | |
|---|---|---|---|---|---|---|
| ccctctccc | tcccccccc | ctaacgttac | tggccgaagc | cgcttggaat | aaggccggtg | 60 |
| tgcgtttgtc | tatatgttat | tttccaccat | attgccgtct | tttggcaatg | tgagggcccg | 120 |
| gaaacctggc | cctgtcttct | tgacgagcat | tcctaggggt | ctttcccctc | tcgccaaagg | 180 |
| aatgcaaggt | ctgttgaatg | tcgtgaagga | agcagttcct | ctggaagctt | cttgaagaca | 240 |
| aacaacgtct | gtagcgaccc | tttgcaggca | gcggaacccc | ccacctggcg | acaggtgcct | 300 |
| ctgcggccaa | aagccacgtg | tataagatac | acctgcaaag | gcggcacaac | cccagtgcca | 360 |

```
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggccccccc gaaccacggg    540 gacgtggttt tcctttgaaa atcgatgtg                                     569
```

<210> SEQ ID NO 58
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 58

```
gcaccggtga aacagacttt gaattttgac cttctgaagt tggcaggaga cgttgagtcc    60
aaccctgggc cc                                                        72
```

<210> SEQ ID NO 59
<211> LENGTH: 24
<212> TYPE: PRT
<213> ORGANISM: Artificial Sequence
<220> FEATURE:
<223> OTHER INFORMATION: Synthetic peptide

<400> SEQUENCE: 59

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 60
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 60

```
cggagaaagc gcgcaccggt gaaacagact ttgaattttg accttctgaa gttggcagga    60
gacgttgagt ccaaccctgg gccc                                           84
```

<210> SEQ ID NO 61
<211> LENGTH: 28
<212> TYPE: PRT
<213> ORGANISM: Artificial Sequence
<220> FEATURE:
<223> OTHER INFORMATION: Synthetic peptide

<400> SEQUENCE: 61

Arg Arg Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 62
<211> LENGTH: 795
<212> TYPE: DNA
<213> ORGANISM: Artificial Sequence
<220> FEATURE:
<223> OTHER INFORMATION: Synthetic oligonucleotide

<400> SEQUENCE: 62

-continued

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120 gcgcagggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat gggcgaagt gccggggcag     300 gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg gctcgcgcc agccgaactg ttcgccaggc tcaaggcgcg catgcccgac     540
ggcgaggatc tcgtcgtgac ccatggcgat gcctgcttgc cgaatatcat ggtgaaaat     600 ggccgctttt ctggattcat cgactgtggc cggctgggtg tggcggaccg ctatcaggac     660
atagcgttgg ctacccgtga tattgctgaa gagcttggcg cgaatgggc tgaccgcttc     720 ctcgtgcttt acggtatcgc cgctcccgat tcgcagcgca tcgccttcta tcgccttctt     780
gacgagttct tctga                                                     795
```

<210> SEQ ID NO 63
<211> LENGTH: 264
<212> TYPE: PRT
<213> ORGANISM: Artificial Sequence
<220> FEATURE:
<223> OTHER INFORMATION: Synthetic peptide

<400> SEQUENCE: 63

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220
```

```
Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 64
<211> LENGTH: 264
<212> TYPE: PRT
<213> ORGANISM: Artificial Sequence
<220> FEATURE:
<223> OTHER INFORMATION: Synthetic peptide

<400> SEQUENCE: 64

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50                 55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Asp Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 65
<211> LENGTH: 264
<212> TYPE: PRT
<213> ORGANISM: Artificial Sequence
<220> FEATURE:
<223> OTHER INFORMATION: Synthetic peptide

```
<400> SEQUENCE: 65

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Gly Glu Phe Phe
            260

<210> SEQ ID NO 66
<211> LENGTH: 264
<212> TYPE: PRT
<213> ORGANISM: Artificial Sequence
<220> FEATURE:
<223> OTHER INFORMATION: Synthetic peptide

<400> SEQUENCE: 66

Leu Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
```

```
            85                  90                  95
Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
            130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
                210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Gly Glu Phe Phe
            260
```

<210> SEQ ID NO 67
<211> LENGTH: 795
<212> TYPE: DNA
<213> ORGANISM: Artificial Sequence
<220> FEATURE:
<223> OTHER INFORMATION: Synthetic oligonucleotide

<400> SEQUENCE: 67

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcagggggc gcccggttct ttttgtcaag accgacctgt ccggtgccct gaatgaactg   180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgatgatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

<210> SEQ ID NO 68
<211> LENGTH: 795
<212> TYPE: DNA
<213> ORGANISM: Artificial Sequence
<220> FEATURE:

<223> OTHER INFORMATION: Synthetic oligonucleotide

<400> SEQUENCE: 68

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcagggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
ggcgagttct tctga                                                    795
```

<210> SEQ ID NO 69
<211> LENGTH: 795
<212> TYPE: DNA
<213> ORGANISM: Artificial Sequence
<220> FEATURE:
<223> OTHER INFORMATION: Synthetic oligonucleotide

<400> SEQUENCE: 69

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcagggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgatgatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
ggcgagttct tctga                                                    795
```

<210> SEQ ID NO 70
<211> LENGTH: 264
<212> TYPE: PRT
<213> ORGANISM: Artificial Sequence
<220> FEATURE:
<223> OTHER INFORMATION: Synthetic peptide

<400> SEQUENCE: 70

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
210                 215                 220

Thr Arg Gly Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 71
<211> LENGTH: 264
<212> TYPE: PRT
<213> ORGANISM: Artificial Sequence
<220> FEATURE:
<223> OTHER INFORMATION: Synthetic peptide

<400> SEQUENCE: 71

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

```
Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
            130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Gly Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
            210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 72
<211> LENGTH: 264
<212> TYPE: PRT
<213> ORGANISM: Artificial Sequence
<220> FEATURE:
<223> OTHER INFORMATION: Synthetic peptide

<400> SEQUENCE: 72

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Ala Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
            130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190
```

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
        210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 73
<211> LENGTH: 264
<212> TYPE: PRT
<213> ORGANISM: Artificial Sequence
<220> FEATURE:
<223> OTHER INFORMATION: Synthetic peptide

<400> SEQUENCE: 73

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Gly Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 74

<211> LENGTH: 264
<212> TYPE: PRT
<213> ORGANISM: Artificial Sequence
<220> FEATURE:
<223> OTHER INFORMATION: Synthetic peptide

<400> SEQUENCE: 74

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Ala Ile Ala Glu Glu Leu Gly Gly Glu Trp Ala Asp Arg Phe
225                 230                 235                 240

Leu Val Leu Tyr Gly Ile Ala Pro Asp Ser Gln Arg Ile Ala Phe
                245                 250                 255

Tyr Arg Leu Leu Asp Glu Phe Phe
            260
```

<210> SEQ ID NO 75
<211> LENGTH: 264
<212> TYPE: PRT
<213> ORGANISM: Artificial Sequence
<220> FEATURE:
<223> OTHER INFORMATION: Synthetic peptide

<400> SEQUENCE: 75

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
```

```
                    50                  55                  60
Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
                115                 120                 125

Ala Thr Cys Pro Phe Asp His Gln Ala Lys His Arg Ile Glu Arg Ala
                130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
210                 215                 220

Thr Arg Val Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260

<210> SEQ ID NO 76
<211> LENGTH: 264
<212> TYPE: PRT
<213> ORGANISM: Artificial Sequence
<220> FEATURE:
<223> OTHER INFORMATION: Synthetic peptide

<400> SEQUENCE: 76

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
                35                  40                  45

Val Lys Thr Asp Leu Ser Gly Ala Leu Asn Glu Leu Gln Asp Glu Ala
             50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
                115                 120                 125

Ala Thr Cys Pro Phe Asp His Gln Ala Lys His Arg Ile Glu Arg Ala
                130                 135                 140

Arg Thr Arg Met Glu Ala Gly Leu Val Asp Gln Asp Asp Leu Asp Glu
```

```
                145                 150                 155                 160
Glu His Gln Gly Leu Ala Pro Ala Glu Leu Phe Ala Arg Leu Lys Ala
                    165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
        210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asn Glu Phe Phe
                260

<210> SEQ ID NO 77
<211> LENGTH: 264
<212> TYPE: PRT
<213> ORGANISM: Artificial Sequence
<220> FEATURE:
<223> OTHER INFORMATION: Synthetic peptide

<400> SEQUENCE: 77

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
        210                 215                 220

Thr Arg Asp Ile Ala Glu Glu Leu Gly Gly Glu Trp Ala Asp Arg Ile
225                 230                 235                 240

Leu Val Leu Tyr Gly Ile Ala Ala Pro Asp Ser Gln Arg Ile Ala Phe
```

Tyr Arg Leu Leu Asp Glu Phe Phe
                260

<210> SEQ ID NO 78
<211> LENGTH: 711
<212> TYPE: DNA
<213> ORGANISM: Artificial Sequence
<220> FEATURE:
<223> OTHER INFORMATION: Synthetic oligonucleotide

<400> SEQUENCE: 78

| | | | | | |
|---|---|---|---|---|---|
| atggacatga | gggtccctgc | tcagctcctg | gggctcctgc | tgctctggct | ctcaggtgcc | 60 |
| agatgtgata | tccagatgac | ccagtccccg | agctccctgt | ccgcctctgt | gggcgatagg | 120 |
| gtcactatca | cctgccgtgc | cagtcaggat | gtgaatactg | ctgtagcctg | gtatcaacag | 180 |
| aaacccggaa | aggccccgaa | actgctgatt | tactcggcat | ccttcctcta | ctctggagtc | 240 |
| ccttctcgct | tctctggttc | ccgctctggg | acggatttca | ctctgaccat | cagctccctg | 300 |
| cagccggaag | acttcgcaac | ttattactgt | cagcaacact | atactactcc | tccgacgttc | 360 |
| ggacagggta | ccaaggtgga | gatcaaacgt | acggtggcgg | cgccatctgt | cttcatcttc | 420 |
| ccgccatctg | atgagcagtt | gaaatctgga | actgcctctg | ttgtgtgcct | gctgaataac | 480 |
| ttctatccca | gagaggccaa | agtacagtgg | aaggtggata | acgccctcca | atcgggtaac | 540 |
| tcccaggaga | gtgtcacaga | gcaggacagc | aaggacagca | cctacagcct | cagcagcacc | 600 |
| ctgacgctga | gcaaagcaga | ctacgagaaa | cacaaagtct | acgcctgcga | agtcacccat | 660 |
| cagggcctga | gctcgcccgt | cacaaagagc | ttcaacaggg | gagagtgtta | g | 711 |

<210> SEQ ID NO 79
<211> LENGTH: 236
<212> TYPE: PRT
<213> ORGANISM: Artificial Sequence
<220> FEATURE:
<223> OTHER INFORMATION: Synthetic peptide

<400> SEQUENCE: 79

Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210             215                 220

Ser Pro Val Thr Lys Ser Phe Asn Arg Gly Glu Cys
225             230                 235

<210> SEQ ID NO 80
<211> LENGTH: 1410
<212> TYPE: DNA
<213> ORGANISM: Artificial Sequence
<220> FEATURE:
<223> OTHER INFORMATION: Synthetic oligonucleotide

<400> SEQUENCE: 80
atggagttgg gactgagctg gattttcctt ttggctattt taaaaggtgt ccagtgtgag      60
gttcagctgg tggagtctgg cggtggcctg gtgcagcccg ggggctctct ccgtttgtcc     120
tgtgcagctt ctggcttcaa cattaaagac acctatatcc actgggtgcg tcaggctccg     180
ggtaagggcc tggagtgggt tgcaaggatt tatcctacga atggttatac tcgttatgcc     240
gatagcgtca agggccgttt cactataagc gcagacactt cgaaaaacac agcctacctc     300
cagatgaaca gcctgcgtgc tgaggacact gccgtctatt attgtagcag atggggtggg     360
gacggcttct atgctatgga ctactggggt caaggtacac tagtcaccgt cagcagcgct     420
agcaccaagg gcccatcggt cttccccctg gcaccctcct ccaagagcac ctctgggggc     480
acagcggccc tgggctgcct ggtcaaggac tacttccccg aaccggtgac ggtgtcatgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410

<210> SEQ ID NO 81
<211> LENGTH: 469
<212> TYPE: PRT
<213> ORGANISM: Artificial Sequence
<220> FEATURE:
```

<223> OTHER INFORMATION: Synthetic peptide

<400> SEQUENCE: 81

```
Met Glu Leu Gly Leu Ser Trp Ile Phe Leu Leu Ala Ile Leu Lys Gly
1               5                   10                  15
Val Gln Cys Glu Val Gln Leu Val Glu Ser Gly Gly Gly Leu Val Gln
            20                  25                  30
Pro Gly Gly Ser Leu Arg Leu Ser Cys Ala Ala Ser Gly Phe Asn Ile
        35                  40                  45
Lys Asp Thr Tyr Ile His Trp Val Arg Gln Ala Pro Gly Lys Gly Leu
    50                  55                  60
Glu Trp Val Ala Arg Ile Tyr Pro Thr Asn Gly Tyr Thr Arg Tyr Ala
65                  70                  75                  80
Asp Ser Val Lys Gly Arg Phe Thr Ile Ser Ala Asp Thr Ser Lys Asn
                85                  90                  95
Thr Ala Tyr Leu Gln Met Asn Ser Leu Arg Ala Glu Asp Thr Ala Val
            100                 105                 110
Tyr Tyr Cys Ser Arg Trp Gly Gly Asp Gly Phe Tyr Ala Met Asp Tyr
        115                 120                 125
Trp Gly Gln Gly Thr Leu Val Thr Val Ser Ser Ala Ser Thr Lys Gly
    130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
```

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 82
<211> LENGTH: 564
<212> TYPE: DNA
<213> ORGANISM: Artificial Sequence
<220> FEATURE:
<223> OTHER INFORMATION: Synthetic oligonucleotide

<400> SEQUENCE: 82
atggttcgac cattgaactg catcgtcgcc gtgtcccaag atatggggat tggcaagaac      60
ggagacctac cctggcctcc gctcaggaac gagttcaagt acttccaaag aatgaccaca     120
acctcttcag tggaaggtaa acagaatctg gtgattatgg gtaggaaaac ctggttctcc     180
attcctgaga gaatcgacc tttaaaggac agaattaata tagttctcag tagagaactc     240
aaagaaccac cacgaggagc tcattttctt gccaaaagtt tggatgatgc cttaagactt     300
attgaacaac cggaattggc aagtaaagta gacatggttt ggatagtcgg aggcagttct     360
gtttaccagg aagccatgaa tcaaccaggc cacctcagac tctttgtgac aaggatcatg     420
caggaatttg aaagtgacac gttttttccca gaaattgatt tggggaaata taaacttctc     480
ccagaatacc caggcgtcct ctctgaggtc caggaggaaa aaggcatcaa gtataagttt     540
gaagtctacg agaagaaaga ctaa                                            564

<210> SEQ ID NO 83
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 83
aaatcgatat gataatatg                                                   19

<210> SEQ ID NO 84
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 84
aaatcgatgt gataatatgg ccgcaaccgt g                                     31

<210> SEQ ID NO 85
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 85

-continued aaatcgatat g                                                    11

<210> SEQ ID NO 86
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 86
aaatcgatct gataatctgg ccgcaaccct g                              31

<210> SEQ ID NO 87
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 87
aaatcgatat gataatctgg ccgcaaccct g                              31

<210> SEQ ID NO 88
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 88
aaatcgatac gataatacgg ccgcaaccac g                              31

<210> SEQ ID NO 89
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 89
aaatcgatgt gataatgtgg ccgcaaccgt g                              31

<210> SEQ ID NO 90
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 90
aaatcgatat gataatacgg ccgcaaccac g                              31

<210> SEQ ID NO 91
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 91
aaatcgatat aataatatag ccgcaaccat a                              31

<210> SEQ ID NO 92
<211> LENGTH: 31
<212> TYPE: DNA
<213> ORGANISM: Artificial Sequence

```
<220> FEATURE:
<223> OTHER INFORMATION: Synthetic oligonucleotide

<400> SEQUENCE: 92
aaatcgatat gataatgtgg ccgcaaccgt g                              31

<210> SEQ ID NO 93
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 93
aaatcgatat gataatatag ccgcaaccat a                              31

<210> SEQ ID NO 94
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 94
aaatcgattt gataatttgg ccgcaaccct g                              31

<210> SEQ ID NO 95
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 95
aaatcgatgt gataatgtg                                            19

<210> SEQ ID NO 96
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 96
aaatcgatat gataatttgg ccgcaaccct g                              31

<210> SEQ ID NO 97
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 97
aaatcgatat gataatgtg                                            19

<210> SEQ ID NO 98
<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 98
cccctctccc tccccccccc ctaacgttac tggccgaagc cgcttggaat aaggccggtg    60
```

```
tgcgtttgtc tatatgttat tttccaccat attgccgtct tttggcaatg tgagggcccg      120
gaaacctggc cctgtcttct tgacgagcat tcctaggggt cttccgctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct      300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggtg     480
cacatgcttt acgtgtgttt agtcgaggtt aaaaaacgtc taggcccccc gaaccacggg     540
gacgtggttt tcctttgaaa atcgatatga taatatg                              577
```

<210> SEQ ID NO 99
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 99

```
ccctctctccc tccccccccc ctaacgttac tggccgaagc cgcttggaat aaggccggtg     60
tgcgtttgtc tatatgttat tttccaccat attgccgtct tttggcaatg tgagggcccg     120
gaaacctggc cctgtcttct tgacgagcat tcctaggggt cttccgctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acgtgtgttt agtcgaggtt aaaaaacgtc taggcccccc gaaccacggg    540
gacgtggttt tcctttgaaa atcgatgtga taatatggcc gcaaccgtg                589
```

<210> SEQ ID NO 100
<211> LENGTH: 569
<212> TYPE: DNA
<213> ORGANISM: Artificial Sequence
<220> FEATURE:
<223> OTHER INFORMATION: Synthetic oligonucleotide

<400> SEQUENCE: 100

```
ccctctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt cttccgctc tcgccaaagg     180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acgtgtgttt agtcgaggtt aaaaaacgtc taggcccccc gaaccacggg   540
gacgtggttt tcctttgaaa atcgatatg                                     569
```

<210> SEQ ID NO 101
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 101

```
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggtg     480
cacatgcttt acgtgtgttt agtcgaggtt aaaaaacgtc taggcccccc gaaccacggg     540
gacgtggttt cctttgaaa atcgatctga taatctggcc gcaaccctg                  589
```

<210> SEQ ID NO 102
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 102

```
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggtg     480
cacatgcttt acgtgtgttt agtcgaggtt aaaaaacgtc taggcccccc gaaccacggg     540
gacgtggttt cctttgaaa atcgatatga taatctggcc gcaaccctg                  589
```

<210> SEQ ID NO 103
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 103

```
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
```

```
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa atcgatacga taatacggcc gcaaccacg                589

<210> SEQ ID NO 104
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 104
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt ctttccctc tcgccaaagg    180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa atcgatgtga taatgtggcc gcaaccgtg                589

<210> SEQ ID NO 105
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 105
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt ctttccctc tcgccaaagg    180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggcccccc gaaccacggg    540
gacgtggttt tcctttgaaa atcgatatga taatacggcc gcaaccacg                589

<210> SEQ ID NO 106
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 106
```

```
ccctctccc tccccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctaggggt cttccctc tcgccaaagg     180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggccccccc gaaccacggg   540 gacgtggttt tcctttgaaa atcgatataa taatatagcc gcaaccata                589
```

<210> SEQ ID NO 107
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 107

```
ccctctccc tccccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctaggggt ctttccctc tcgccaaagg     180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggccccccc gaaccacggg   540 gacgtggttt tcctttgaaa atcgatatga taatgtggcc gcaaccgtg                589
```

<210> SEQ ID NO 108
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 108

```
ccctctccc tccccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctaggggt ctttccctc tcgccaaagg     180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acgtgtgttt agtcgaggtt aaaaaacgtc taggccccccc gaaccacggg   540
```

```
gacgtggttt tcctttgaaa atcgatatga taatatagcc gcaaccata            589
```

<210> SEQ ID NO 109
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 109

```
cccctctccc tccccccccc ctaacgttac tggccgaagc cgcttggaat aaggccggtg   60
tgcgtttgtc tatatgttat tttccaccat attgccgtct tttggcaatg tgagggcccg  120
gaaacctggc cctgtcttct tgacgagcat tcctagggg ctttcccctc tcgccaaagg  180
aatgcaaggt ctgttgaatg tcgtgaagga agcagttcct ctggaagctt cttgaagaca  240
aacaacgtct gtagcgaccc tttgcaggca gcggaacccc ccacctggcg acaggtgcct  300
ctgcggccaa aagccacgtg tataagatac acctgcaaag gcggcacaac cccagtgcca  360
cgttgtgagt tggatagttg tggaaagagt caaatggctc tcctcaagcg tattcaacaa  420
ggggctgaag gatgcccaga aggtacccca ttgtatggga tctgatctgg ggcctcggtg  480
cacatgcttt acgtgtgttt agtcgaggtt aaaaaacgtc taggccccccc gaaccacggg  540
gacgtggttt tcctttgaaa atcgatttga taatttggcc gcaaccttg             589
```

<210> SEQ ID NO 110
<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 110

```
ccctctccc tccccccccc ctaacgttac tggccgaagc cgcttggaat aaggccggtg    60
tgcgtttgtc tatatgttat tttccaccat attgccgtct tttggcaatg tgagggcccg  120
gaaacctggc cctgtcttct tgacgagcat tcctagggg ctttcccctc tcgccaaagg  180
aatgcaaggt ctgttgaatg tcgtgaagga agcagttcct ctggaagctt cttgaagaca  240
aacaacgtct gtagcgaccc tttgcaggca gcggaacccc ccacctggcg acaggtgcct  300
ctgcggccaa aagccacgtg tataagatac acctgcaaag gcggcacaac cccagtgcca  360
cgttgtgagt tggatagttg tggaaagagt caaatggctc tcctcaagcg tattcaacaa  420
ggggctgaag gatgcccaga aggtacccca ttgtatggga tctgatctgg ggcctcggtg  480
cacatgcttt acgtgtgttt agtcgaggtt aaaaaacgtc taggccccccc gaaccacggg  540
gacgtggttt tcctttgaaa atcgatgtga taatgtg                          577
```

<210> SEQ ID NO 111
<211> LENGTH: 589
<212> TYPE: DNA
<213> ORGANISM: Artificial Sequence
<220> FEATURE:
<223> OTHER INFORMATION: Synthetic oligonucleotide

<400> SEQUENCE: 111

```
ccctctccc tccccccccc ctaacgttac tggccgaagc cgcttggaat aaggccggtg    60
tgcgtttgtc tatatgttat tttccaccat attgccgtct tttggcaatg tgagggcccg  120
gaaacctggc cctgtcttct tgacgagcat tcctagggg ctttcccctc tcgccaaagg  180
aatgcaaggt ctgttgaatg tcgtgaagga agcagttcct ctggaagctt cttgaagaca  240
```

```
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtaccccca ttgtatggga tctgatctgg ggcctcggtg   480
cacatgcttt acgtgtgttt agtcgaggtt aaaaaacgtc taggccccccc gaaccacggg   540 gacgtggttt tcctttgaaa atcgatatga taatttggcc gcaaccttg                589

<210> SEQ ID NO 112
<211> LENGTH: 577
<212> TYPE: DNA
<213> ORGANISM: Artificial Sequence
<220> FEATURE:
<223> OTHER INFORMATION: Synthetic oligonucleotide

<400> SEQUENCE: 112
cccctctccc tcccccccccc ctaacgttac tggccgaagc cgcttggaat aaggccggtg    60
tgcgtttgtc tatatgttat tttccaccat attgccgtct tttggcaatg tgagggcccg    120
gaaacctggc cctgtcttct tgacgagcat tcctagggt cttccctc tcgccaaagg      180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtaccccca ttgtatggga tctgatctgg ggcctcggtg   480
cacatgcttt acgtgtgttt agtcgaggtt aaaaaacgtc taggccccccc gaaccacggg   540 gacgtggttt tcctttgaaa atcgatatga taatgtg                             577

<210> SEQ ID NO 113
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 113
aaaacacgat gataatatgg ccacaaccat g                                    31

<210> SEQ ID NO 114
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 114
aaaacacgat gataagcttg ccacaacccc gggagatgag gatcgtttcg catg            54

<210> SEQ ID NO 115
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 115
gtgataatgt g                                                          11
```

```
<210> SEQ ID NO 116
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 116
atgataatgt g                                                              11

<210> SEQ ID NO 117
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 117
atgataatat g                                                              11

<210> SEQ ID NO 118
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 118
gtgataatgt ggccgcaacc gtg                                                 23

<210> SEQ ID NO 119
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 119
atgataatgt ggccgcaacc gtg                                                 23

<210> SEQ ID NO 120
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 120
gtgataatgt ggccgcaacc atg                                                 23

<210> SEQ ID NO 121
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 121
gtgataatat ggccgcaacc gtg                                                 23

<210> SEQ ID NO 122
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 122
atgataatgt ggccgcaacc atg                                    23

<210> SEQ ID NO 123
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 123
atgataatat ggccgcaacc gtg                                    23

<210> SEQ ID NO 124
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 124
gtgataatat ggccgcaacc atg                                    23

<210> SEQ ID NO 125
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 125
atgataagct tgccacaacc ccgggagatg aggatcgttt cgcatg           46

<210> SEQ ID NO 126
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 126
atgataatat ggccacaacc atg                                    23
```

IRES MEDIATED MULTICISTRONIC VECTORS

CROSS-REFERENCE TO RELATED APPLICATIONS

This application makes reference to and claims the benefit of priority of an application for "IRES-mediated tricistronic vectors for rapid generation of stable, high monoclonal antibody expressing CHO cell lines" filed on May 24, 2011, with the United States Patent and Trademark Office, and there duly assigned Ser. No. 61/489,277. The content of said application filed on May 24, 2011, is incorporated herein by reference in its entirety for all purposes.

FIELD

The present invention lies in the field of molecular biology, recombinant peptide and protein expression and relates to nucleic acid sequences comprising at least one IRES sequences and at least one sequence encoding for a peptide or protein of interest.

BACKGROUND

The global biologics market has steadily growth in recent years. Among the biologics, the top product has been monoclonal antibodies (mAb), achieving sales of $16.9 billion in the US in 2009 (Aggarwal S 2010. Nature Biotechnology 28(11):1165-1171). There are currently over 20 mAbs approved for sale and almost a hundred more going through various stages of clinical testing (Nelson A L, Dhimolea E, Reichert J M. 2010. Nat Rev Drug Discov 9(10):767-74). Mammalian cells, particularly Chinese hamster ovary (CHO) cells are the dominant host for industrial mAb production because of their capacity for proper protein folding, assembly and appropriate post-translational modifications (Wurm F M 2004. Nat Biotechnol 22(11):1393-8).

To obtain high-level expression, the most commonly used expression system is dihydrofolate reductase deficient (DHFR−) CHO cells in conjunction with two vectors, one expressing a DHFR selection marker linked to one mAb gene, light chain (LC) or heavy chain (HC), the other vector expressing an alternative selection marker linked to the second mAb gene (Kim N S, Kim S J, Lee G M. 1998a. Biotechnology And Bioengineering 60(6):679-688; Kim S J, Kim N S, Ryu C J, Hong H J, Lee G M. 1998b. Biotechnol Bioeng 58(1):73-84.). Each gene is under the control of its own promoter and expressed as separate transcript. DHFR catalyzes the reduction of dihydrofolate into tetrahydrofolate, an essential co-factor in the synthesis of purines and amino acids.

To enrich the proportion of high producers after drug selection thus reduce efforts of clone screening, the stringency of clone selection can be improved by weakening the selection marker. The principle is that only those clones with greater transcription activity or more copies of the integrated vector, which often means higher productivity, survives the selection process (Fussenegger, M et al., 1999. Trends In Biotechnology 17(1): 35-42; Ng, S K et al. 2007. Metabolic Engineering 9(3): 304-316).

In the context of DHFR based selection systems, the expression is performed in media lacking glycine, hypoxanthine, and thymidine and enhanced expression level can be achieved by exposure to methotrexate (MTX), a DHFR inhibitor, leading to the amplification the gene copy numbers. Theoretically, after a few rounds of selection in medium containing stepwise increments of methotrexate (MTX), the copies of the gene of interest should be increased up to hundred folds leading to clones with high productivity.

Other reported strategies of weakening selection marker are based on either reducing expression level through application of weak regulatory elements like promoters on the selection marker (Barnett, R S et al. 1995. Antibody Expression And Engineering. 604: 27-40.) or use of codon deoptimized selection marker (Westwood, A D et al. 2010. Biotechnology Progress 26(6): 1558-1566), or impairment of the selection marker function, such as mutation of critical amino acids in neomycin phosphorase (NPT) selection marker (Yenofsky, R L et al. 1990. PNAS 87(9): 3435-3439; Niwa, H et al. 1991. Gene 108(2): 193-199; Sautter, K and Enenkel, B 2005. Biotechnol Bioeng 89(5): 530-538).

However, the above technologies are limited by the fact that, e.g., due to vector fragmentation with concomitant deletion of the mAb gene expression cassettes effective simultaneous amplification of both antibody chains is rare. In many cases, only the mAb chain linked to the marker is amplified or even none of both mAb genes is amplified. As a result, a large number of clones have to be screened to obtain high producing clones, making the cell line generation process labor intensive and extremely time consuming.

Internal ribosome entry site (IRES) and 2A peptide provides alternative approaches for co-expression of multiple genes. Internal ribosome entry site (IRES) elements allow expression of multiple genes in one transcript (Mountford and Smith 1995). IRES-based bicistronic or tricistronic vectors, which express the product and selection marker genes in one transcript, can minimize the escape of non-expressing clones from selection, as none of the two genes will be expressed should vector fragmentation happen. In these vectors, the product and selection marker genes are under the control of the same promoter. However, one concern for the use of IRES in expressing mAbs is that the gene driven by IRES has lower translation efficiency than the gene under the 5′-cap dependent translation.

In contrast, the 2A peptide allows translation of multiple proteins in a single open reading frame into a polyprotein that is subsequently cleaved into individual proteins through a ribosome-skipping mechanism (Funston, Kallioinen et al. 2008). As compared to IRES, 2A peptide may provide more balanced expression of LC and HC. However, the large size of the polyprotein, e.g., the sum of LC and HC, is believed to result in lower translation efficiency and product instability.

So far, there are very few studies on the use of IRES and 2A for the generation of stable recombinant expressing cell lines.

There is still need in the art for nucleic acid molecules encoding for recombinant peptides or proteins and comprising 2A and/or IRES sequences that allow for an improved production of highly productive and/or stable cell lines.

SUMMARY

The present invention meets this need and, in a first aspect, relates to a nucleic acid molecule comprising at least one nucleic acid sequence encoding for a peptide or protein of interest, at least one nucleic acid sequence encoding for a selectable marker, and at least one IRES sequence, wherein the at least one IRES sequence is located between the at least one nucleic acid sequence encoding for the peptide or protein of interest and the at least one nucleic acid sequence encoding for the selectable marker, and the at least one nucleic acid sequence encoding for a selectable marker has a reduced translation efficiency and/or the encoded selectable marker is mutated such that it has a lowered activity compared to its wildtype variant and/or the at least one IRES sequence is located 5' to a nucleic acid sequence encoding for a selectable marker and is mutated such that it has a reduced ribosome binding affinity compared to the corresponding wildtype IRES sequence wherein the at least one IRES sequence comprises or consists of a nucleic acid sequence selected from the group of nucleic acid sequences set forth in SEQ ID NO:02-57 and 83-112.

In certain embodiments, the at least one IRES sequence of the nucleic acid molecule is mutated such that it has a reduced ribosome binding affinity compared to the corresponding wildtype IRES sequence.

In some embodiments, the at least one IRES sequence is selected from the group of nucleic acid sequences set forth in SEQ ID NO:30-57 and 98-112.

In various embodiments, the nucleic acid molecule comprises two nucleic acid sequences encoding for a peptide or protein of interest and two IRES sequences, wherein the two nucleic acid sequences encoding for a peptide or protein of interest encode for two distinct peptides or proteins of interest.

In some embodiments, the nucleic acid molecule has the following 5' to 3' organization: A-B-C-D-E, A-B-E-D-C, or E-B-A-D-C, wherein A is a first nucleic acid sequence encoding for the first peptide or protein of interest, B is a first IRES sequence, C is a second nucleic acid sequence encoding for the second peptide or protein of interest, D is a second IRES sequence, and E is a nucleic acid sequence encoding for a selectable marker.

In certain embodiments, the nucleic acid molecule has the organization A-B-C-D-E and D has a reduced ribosome binding affinity compared to the corresponding wildtype IRES sequence or wherein D is selected from the group of sequences set forth in SEQ ID NO:30-57 and 98-112.

In various embodiments, the nucleic acid molecule has the organization A-B-E-D-C and B has a reduced ribosome binding affinity compared to the corresponding wildtype IRES sequence or wherein B is selected from the group of sequences set forth in SEQ ID NO:30-57 and 98-112.

In still further embodiments, the nucleic acid molecule has the organization E-B-A-D-C and E has reduced translation efficiency and/or E has a lowered selection activity compared to its wildtype variant.

In some embodiments, the at least one selection marker is selected from the group consisting of a fluorescent protein, an enzyme, an antibiotic resistance gene, and an auxotrophic marker gene.

In various embodiments, the selectable marker is selected from the group consisting of GFP, a luciferase, a peroxidase, neomycin phosphotransferase, dihydrofolate reductase, glutamine synthetase, thymidylate synthase, puromycin-N-acetyl transferase, and the enzyme encoded by the Sh ble gene.

In certain embodiments, the nucleic acid sequence encoding for the at least one selectable marker is selected from the group of nucleic acid sequences set forth in SEQ ID NOs:62, 67-69 or wherein the nucleic acid sequence encoding for the at least one selectable marker encodes for a protein having a sequence as set forth SEQ ID NOs:63-66, 70-77.

In some embodiments, the nucleic acid molecule encoding for the selectable marker encodes for a selectable marker which is less active than its corresponding wildtype selectable marker, wherein the reduction in activity is by at least 10, 20, 30, 40, 50, 60, 70, 80, 90, 95, 97, 98, or 99% compared to the wildtype selectable marker.

In various embodiments, the nucleic acid molecule further comprises a nucleic acid sequence directly 5' to the nucleic acid sequence encoding the selectable marker that when expressed in a cell forms a secondary structure within the mRNA and causes a reduced translation efficiency of the sequence encoding the selectable marker.

In certain embodiments, the sequence being directly 5' to the at least one nucleic acid sequence encoding the selectable marker forms a secondary structure within the mRNA and causes a reduced translation efficiency of the sequence encoding the selectable marker is selected from the group consisting of sequences forming a hairpin and a sequence forming a stem-loop.

In certain embodiments, the nucleic acid sequence has a modified codon usage and/or comprises a non-ATG start codon.

In some embodiments, the at least one selectable marker is a neomycin phosphotransferase having a reduced enzymatic activity which is lowered at least by 10, 20, 30, 40, 50, 60, 70, 80, 90, 95, 97, 98, or 99% compared to the wildtype enzyme.

In various embodiments, the nucleic acid sequence encoding for the neomycin phosphotransferase is selected from the group of sequences as set forth in SEQ ID NO:67-69 or wherein the nucleic acid sequence encoding for the neomycin phosphotransferase encodes for a protein having a sequence as set forth SEQ ID NOs:64-66, 70-77.

In certain embodiments, the at least one nucleic acid sequence encoding for the peptide or protein of interest is selected from the group of sequences consisting of sequences encoding for an antibody, an antibody fragment, an antibody light chain (LC), an antibody heavy chain (HC), an fab fragment, and a fusion protein comprising or consisting of an antibody light chain (LC), a protein2A, and an antibody heavy chain (LC).

In some embodiments, the two peptides or proteins of interest encoded by the two nucleic acid sequences encoding for a peptide or protein of interest a) interact with each other, and/or b) form a complex.

In certain embodiments, the nucleic acid molecule has the following 5' to 3' organization:
a) A-B-C-D-E, wherein A is an antibody light chain, C is an antibody heavy chain, D has a reduced ribosome binding affinity compared to the corresponding wildtype IRES sequence or wherein D is selected from the group of sequences as set forth in SEQ ID NO:30-57 and 98-112, and E is a neomycin phosphotransferase having a sequence as set forth in SEQ ID NO:64-66, 70-77;
b) A-B-E-D-C, wherein A is an antibody light chain, B has a reduced ribosome binding affinity compared to the corresponding wildtype IRES sequence or wherein B is selected from the group of sequences set forth in SEQ ID NO:30-57 and 98-112, E is a neomycin phosphotransferase having a sequence as set forth in SEQ ID NO:64-66, 70-77, C is an antibody heavy chain;
c) E-B-A-D-C, wherein E is a neomycin phosphotransferase having a sequence as set forth in SEQ ID NO:64-66, 70-77 or is a dihydrofolate reductase, A is an antibody light chain, C is an antibody heavy chain, wherein E comprises a sequence with reduced translation efficiency and/or E has a lowered activity compared to its wildtype variant;
d) A-B-C-D-E, wherein A is an antibody heavy chain, C is an antibody light chain, D has a reduced ribosome binding affinity compared to the corresponding wildtype IRES sequence or wherein D is selected from the group of sequences as set forth in SEQ ID NO:30-57 and 98-112, and E is a neomycin phosphotransferase having a sequence as set forth in SEQ ID NO:64-66, 70-77;

e) A-B-E-D-C, wherein A is an antibody heavy chain, B has a reduced ribosome binding affinity compared to the corresponding wildtype IRES sequence or wherein B is selected from the group of sequences set forth in SEQ ID NO:30-57 and 98-112, E is a neomycin phosphotransferase having a sequence as set forth in SEQ ID NO:64-66, 70-77, and C is an antibody light chain; or f) E-B-A-D-C, wherein E is a neomycin phosphotransferase having a sequence as set forth in SEQ ID NO:64-66, 70-77 or is a dihydrofolate reductase, A is an antibody heavy chain, C is an antibody light chain, and wherein E comprises a sequence with reduced translation efficiency and/or E has a lowered selection activity compared to its wildtype variant.

In various embodiments, nucleic acid molecule further comprises a promoter and a polyadenylation signal sequence.

In some embodiments, the nucleic acid molecule is comprised in a vector.

In a second aspect, the present invention relates to a host cell comprising a nucleic acid molecule as disclosed herein.

In some embodiments, the nucleic acid molecule is integrated in the genome of the host cell.

In another aspect, the present invention relates to a method for expression of at least one recombinant peptide or protein of interest, wherein the method comprises:
 (a) cultivating a host cell as disclosed herein in a culture medium under conditions that allow expression of the at least one recombinant peptide or protein of interest; and optionally
 (b) purifying the at least one recombinant peptide or protein of interest.

In various embodiments, the nucleic acid molecule encodes at least two recombinant peptides or proteins of interest and the method further comprises a step (c) of cultivating the host cell in a culture medium under conditions that allow expression of the at least two recombinant peptides or proteins of interest.

In certain embodiments, the at least two recombinant proteins are an antibody light chain (LC) and an antibody heavy chain (HC).

In a further aspect, the present invention relates to a nucleic acid molecule comprising or consisting of a nucleic acid sequence as set forth in SEQ ID NOs: 03-29, 31-57, and 83-112 and complements and fragments thereof.

In another aspect, the present invention relates to a nucleic acid molecule comprising: A: at least one nucleic acid sequence encoding for a selectable marker, B: a first IRES sequence, C: a first nucleic acid sequence encoding for a first recombinant peptide or protein of interest, D: a second IRES sequence, and E: a second nucleic acid sequence encoding for a second recombinant peptide or protein of interest, wherein the 5' to 3' organization of the nucleic acid molecule is A-B-C-D-E.

In some embodiments, a) the at least one selectable marker is selected from the group consisting of GFP, a luciferase, a peroxidase, neomycin phosphotransferase, dihydrofolate reductase, glutamine synthetase, puromycin-N-acetyl transferase, and the enzyme encoded by the Sh ble gene, and/or b) the first recombinant protein is an antibody light chain (LC) and the second recombinant protein is an antibody heavy chain (HC), or c) the first recombinant protein is an antibody heavy chain (HC) and the second recombinant protein is an antibody light chain (LC).

In a further aspect, the present invention relates to a method for expression of at least one recombinant peptide or protein of interest, wherein the method comprises:
 (a) cultivating a host cell comprising a nucleic acid molecule as disclosed herein, wherein the host cell is cultivated in a culture medium under conditions that allow expression of the at least one recombinant peptide or protein of interest, and
 (b) supplementing the culture medium with an inhibitor which increases the selection pressure on the host cell, and optionally
 (c) purifying the at least one recombinant peptide or protein of interest.

In another aspect, the present invention relates to a method of differentially expressing an at least bicistronic nucleic acid construct, wherein the at least bicistronic construct comprises at least one first nucleic acid sequence encoding for a first recombinant peptide or protein of interest, at least one second nucleic acid sequence encoding for a second recombinant peptide or protein of interest, and at least one IRES sequence, wherein the at least one IRES sequence is located between the at least one first nucleic acid sequence encoding for the first recombinant peptide or protein of interest and the at least one second nucleic acid sequence encoding for the second recombinant peptide or protein of interest, wherein the first and the second recombinant peptide or protein of interest interact with each other and/or form a complex, and the at least bicistronic construct is comprised in a host cell which has been transformed with the nucleic acid molecule, and the method comprises cultivating the host cell in a culture medium suitable for expressing the first and the second recombinant peptide or protein of interest, wherein the at least one IRES sequence comprises or consists of a nucleic acid sequence selected from the group of nucleic acid sequences set forth in SEQ ID NOs:3-29, 31-57, and 83-112, and optionally the first recombinant peptide or protein is an antibody light chain and the second recombinant protein is an antibody heavy chain.

In another aspect, the present invention relates to a nucleic acid molecule comprising at least one first nucleic acid sequence encoding for a first peptide or protein of interest, at least one second nucleic acid sequence encoding for a second peptide or protein of interest, and at least one IRES sequence, wherein the at least one IRES sequence is located between the at least one first nucleic acid sequence encoding for the first peptide or protein of interest and the at least one second nucleic acid sequence encoding for the second peptide or protein of interest, and the at least one IRES sequence comprises or consists of a nucleic acid sequence selected from the group of nucleic acid sequences set forth in SEQ ID NO:2-57 and 83-112, and wherein the two nucleic acid sequences encoding for a peptide or protein of interest encode for two distinct peptides or proteins of interest, wherein the at least one IRES sequence optionally is mutated such that it has a reduced ribosome binding affinity compared to the corresponding wildtype IRES sequence.

In certain embodiments, the at least one IRES sequence is optionally selected from the group of nucleic acid sequences set forth in SEQ ID NO:30-57 and 98-112.

In various embodiments, the nucleic acid molecule comprises a nucleic acid sequences encoding for a selectable marker and two IRES sequences.

In certain embodiments, the nucleic acid molecule has the following 5' to 3' organization: A-B-C-D-E, A-B-E-D-C, or E-B-A-D-C, wherein A is a first nucleic acid sequence encoding for the first peptide or protein of interest, B is a first IRES sequence, C is a second nucleic acid sequence encoding for the second peptide or protein of interest, D is a second IRES sequence, and E is a nucleic acid sequence encoding for a selectable marker.

In some embodiments, the nucleic acid molecule encoding for the selectable marker encodes for a selectable marker which is less active than its corresponding wildtype selectable marker, wherein the reduction in activity is by at least 10, 20, 30, 40, 50, 60, 70, 80, 90, 95, 97, 98, or 99% compared to the wildtype selectable marker.

In further embodiments, the two IRES sequences comprise or consist of a nucleic acid sequence selected from the group of nucleic acid sequences set forth in SEQ ID NO:2-57 and 83-112.

In certain embodiments, the nucleic acid molecule further comprises a nucleic acid sequence directly 5' to the nucleic acid sequence encoding the selectable marker that when expressed in a cell forms a secondary structure within the mRNA and causes a reduced translation efficiency of the sequence encoding the selectable marker.

In some embodiments, the sequence being directly 5' to the at least one nucleic acid sequence encoding the selectable marker forms a secondary structure within the mRNA and causes a reduced translation efficiency of the sequence encoding the selectable marker is selected from the group consisting of sequences forming a hairpin and a sequence forming a stem-loop.

In various embodiments, the nucleic acid sequence has optionally a modified codon usage and/or comprises a non-ATG start codon.

In some embodiments, the at least one selectable marker is a neomycin phosphotransferase or dihydrofolate reductase having a reduced enzymatic activity which is lowered at least by 10, 20, 30, 40, 50, 60, 70, 80, 90, 95, 97, 98, or 99% compared to the wildtype enzyme.

In certain embodiments, the nucleic acid sequence encoding for the neomycin phosphotransferase is selected from the group of sequences as set forth in SEQ ID NO:67-69 or wherein the nucleic acid sequence encoding for the neomycin phosphotransferase encodes for a protein having a sequence as set forth SEQ ID NOs:64-66, 70-77.

In various embodiments, the at least one nucleic acid sequence encoding for the peptide or protein of interest is selected from the group of sequences consisting of sequences encoding for an antibody, an antibody fragment, an antibody light chain (LC), an antibody heavy chain (HC), an fab fragment, and a fusion protein comprising or consisting of an antibody light chain (LC), a protein2A, and an antibody heavy chain (LC).

In certain embodiments, nucleic acid molecule comprises four nucleic acid sequences encoding for four distinct peptides or proteins of interest and four IRES sequences, wherein at least two IRES sequences are selected from the group of nucleic acid sequences set forth in SEQ ID NO:2-57 and 83-112.

In some embodiments, the four nucleic acid sequences encoding for four distinct peptides or proteins of interest encode for two distinct antibody light chains and two distinct antibody heavy chains.

BRIEF DESCRIPTION OF THE DRAWINGS

FIG. 2 shows the results of an analysis of the relative strength of EMCV IBES variants in expressing a gene (A and B). Equal amounts of dual-luciferase vectors encoding Rluc and Fluc genes were transfected into CHO K1 cells. In each dual-luciferase vector, a mutated IRES was 5' of the Fluc gene, wherein the in FIG. 1C highlighted start codon was the start codon of the Fluc gene. At 24 h post-transfection, the luciferase activities of the Rluc and Fluc gene were quantified by Dual-Glo Luciferase assay. The results are represented as normalized luciferase activities of Fluc to Rluc and relative to the wild type EMCV IRES activities. Each point represents the average and standard deviation of measurements from four transfections.

FIG. 3 shows the sequence of EMCV IRES (Genebank accession number: X74312, version X74312.1 GI:396509). Highlighted bold and underlined type correspond to the 10th, 11th, and 12th ATGs of the IRES sequence.

FIG. 4 shows a schematic representation of vectors expressing light chain (LC) and/or (HC) cDNAs of, e.g., anti-HER2. A: Co-transfection systems comprising two different vectors, e.g. expression of LC, HC and neomycin phosphotransferase (NPT) using two separate vectors, or co-expression of LC, HC, neomycin phosphotransferase (NPT), and DHFR using two separate vectors. B: Multi-promoter systems, expression of LC, HC and NPT in one vector using multiple promoters. C: Tricistronic vector systems, expression of LC, HC, and NPT in one vector using one promoter, with either LC in the first location (Tri-LIH) or HC in the first location (Tri-HIL). Below of the vector diagrams, a detail of the wildtype EMCV IRES sequence and of a modified variant (IRESatt) are shown. CMV, human cytomegalovirus IE gene promoter; SV40, simian virus 40 promoter; BpA, bovine growth hormone polyadenylation signal; SpA, simian virus 40 early polyadenylation signal; IRESwt; wild type internal ribosomal entry site from encephalomyocarditis virus (EMCV); IRESatt, mutated IRES with attenuated translation efficiency.

FIG. 5 shows a comparison of the expression levels obtained after transient CHO K1 cell transfection with different vectors for mAb in. CHO K1 cells were transfected with different vectors expressing the anti-HER2 LC and HC cDNA. At 48-h post transfection, the mAb concentration in the culture supernatant was determined by ELISA. The diagram shows the obtained mAb concentration normalized to an internal control, GFP expression, and mAb expression from the tricistronic vectors Tri-LIH and TRI-HIL. Each point represents the average and standard deviation of four measurements of two samples from two transfections.

FIG. 7 shows an immunoblot analysis of HC and LC polypeptides secreted from different clones generated using (A) Co-transfection, (B) Multi-promoter, and (C) Tricistronic vectors. Non-reduced supernatant from different clones was loaded on each lane. A commercial human affinity purified myeloma IgG1 (Sigma) and supernatant from cells transfected with a vector expressing only HC and a vector expressing only LC were loaded in separate lanes as positive controls. Supernatant from non-transfected cells was loaded in one lane as negative control (N). The size of secreted $HC_2LC_2$, $HC_2$, $LC_2$, and LC are indicated.

DETAILED DESCRIPTION

Figure 1A:
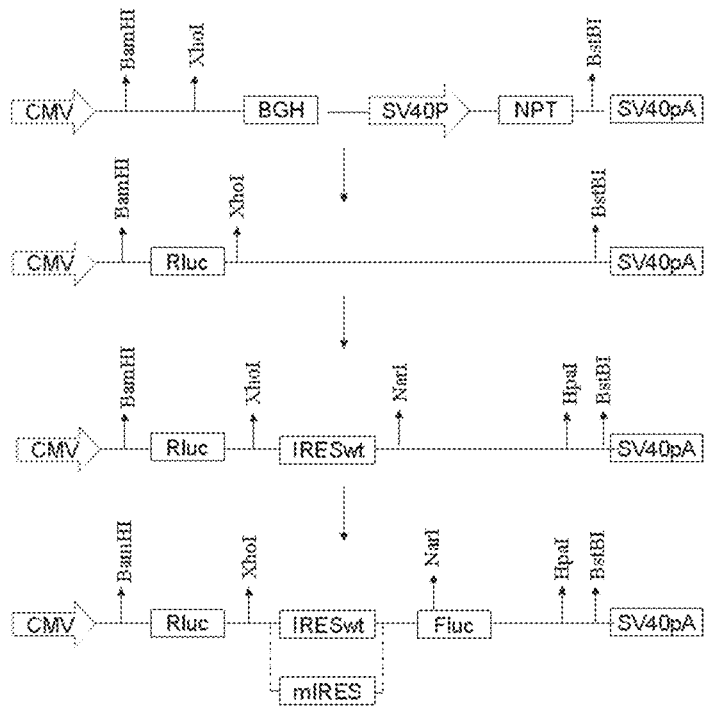
FIG. 1 shows a schematic representation of vectors and IRES sequences. A: Structure of dual-luciferase vectors for determination of the strength of encephalomyocarditis virus (EMCV) IRES variants. B: Structures of vectors for generation of stable cell lines expressing single gene product or mAb. C: Excerpt of the wild type and mutated EMCV IRES sequences. Sequences mutated are highlighted with bold and * denote the start codon of the gene to be expressed. D: Excerpt of the wild type and mutated EMCV IRES sequences. The ATGs of the IRES sequence and the mutated corresponding nucleotide positions are highlighted with underlined type. CMV, human cytomegalovirus IE gene promoter; SV40P, simian virus 40 promoter; BGH, bovine growth hormone polyadenylation signal; S40pA, simian virus 40 early polyadenylation signal; NPT, neomycin phosphorase; IRESwt, wild type EMCV IRES; mIRES, mutated EMCV IRES; Rluc, renilla luciferase cDNA; Fluc, firefly luciferase cDNA; GOI, gene of interest, e.g. single gene product like EPO, or multiple gene product mAb; DHFR, dihydrofolate reductase; IRESatt, commercially available attenuated IRES sequence.

The terms used herein have, unless explicitly stated otherwise, the following meanings.

"At least one", as used herein, relates to one or more, in particular 1, 2, 3, 4, 5, 6, 7, 8, 9, 10 or more.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value The term "nucleic acid molecule" refers to natural nucleic acids, artificial nucleic acids, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "a peptide or protein of interest" as disclosed herein covers any naturally or non-naturally occurring peptide or protein. In some embodiments, the peptide or protein of interest is a non-natural/synthetic peptide or protein. Synthetic in this connection means that the sequence of the peptide or protein has been artificially designed. Thus, a sequence encoding for a peptide or protein of interest may comprise a nucleic acid sequence encoding for one, two or more naturally occurring peptides or proteins. These naturally occurring peptides or proteins may have been further modified, e.g., by mutagenesis of the encoding sequence.

If the peptide or protein of interest comprises two or more naturally occurring peptides or proteins fused together, the two or more peptides or proteins may be separated by protease cleavage sites and/or a protein 2A sequence.

Also encompassed by the term "a peptide or protein of interest" are peptides or proteins comprising one or more affinity tags. Generally, any peptide or protein may be chosen as protein of interest. In certain embodiments, the protein of interest is a protein which does not form a homo-dimer or homo-multimer. The avoidance of self-interacting peptides or proteins may be advantageous if the recombinant peptide or protein is to be secreted into the cell culture supernatant, because the formation of larger protein complexes may disturb an efficient protein export. However, the protein of interest may also be a peptide or protein which is usually a subunit of a larger peptide or protein complex. Such a peptide or protein may be isolated after expression and optionally secretion and be suitable for an in vitro reconstitution of the multi peptide or protein complex. In certain embodiments, the protein or peptide of interest is a peptide having less than 100 amino acid residues, for example about 2 to 80, 3 to 60, 5 to 50, or 10 to 40 amino acid residues. If these peptides comprise pre- and/or pro-sequences in their native state after translation the nucleic acid sequence encoding for the peptide of interest may be engineered to be limited to the sequence encoding the mature peptide. One exemplary peptide is insulin, e.g., human insulin.

In certain embodiments, the peptide or protein of interest further comprises an affinity tag and/or a protease cleavage site.

The term "affinity tag" as used herein relates to entities which are coupled to a molecule of interest and allow enrichment of the complex between the molecule of interest and the affinity tag using an affinity tag receptor. In certain embodiments affinity tags may be selected from the group consisting of the Strep-Tag® or Strep-Tag® II, the myc-tag, the FLAG-tag, the His-tag, the small ubiquitin-like modifier (SUMO) tag, the covalent yet dissociable NorpD peptide (CYD) tag, the heavy chain of protein C (HPC) tag, the calmodulin binding peptide (CBP) tag, or the HA-tag or proteins such as Streptavidin binding protein (SBP), maltose binding protein (MBP), and glutathione-S-transferase.

The term "protease cleavage site" refers to peptide sequence which can be cleaved by a selected protease thus allowing the separation of peptide or protein sequences which are interconnected by a protease cleavage site. In certain embodiments the protease cleavage site is selected from the group consisting of a Furin, a Factor Xa-, a tobacco edge virus (TEV) protease-, a enterokinase-, a SUMO Express protease-, an Arg-C proteinase-, an Asp-N endopeptidases-, an Asp-N endopeptidase+N-terminal Glu-, a caspase1-, a caspase2-, a caspase3-, a caspase4, a caspase5, a caspase6, a caspase7, a caspase8, a caspase9, a caspase10, a chymotrypsin-high specificity, a chymotrypsin-low specificity-, a clostripain (Clostridiopeptidase B)-, a glutamyl endopeptidase-, a granzymeB-, a pepsin-, a proline-endopeptidase-, a proteinase K-, a staphylococcal peptidase I—, a Thrombin-, a Trypsin-, and a Thermolysin-cleavage site.

Also, the peptide or protein of interest may be a fusion protein encoded in a single cistron.

The term "fusion protein" as used herein concerns peptides and proteins which are N- or C-terminally connected to each other. Such fusion proteins may be encoded by nucleic acid sequences which are operably fused to each other.

A fusion protein may be constituted by any two or more proteins which may be directly fused together or be linked by additional amino acid, such as an affinity tag and/or a protease cleavage site.

Generally, the skilled person understands that for putting the present invention into practice any nucleotide sequence described herein may or must comprise an additional start and/or stop codon or that a start and/or stop codon of any of the sequences described herein may or must be deleted depending on the nucleic acid construct used. The skilled person will base this decision, e.g., on whether a nucleic acid sequence comprised in the nucleic acid molecule of the present invention is to be translated and/or is to be translated as a fusion protein, in particular a protein or peptide N- or C-terminally fused with polypeptides encoded by 3' preceding or 5' following nucleic acid sequences.

In various embodiments, the peptide or protein of interest is an enzyme.

The International Union of Biochemistry and Molecular Biology has developed a nomenclature for enzymes, the EC numbers; each enzyme is described by a sequence of four numbers preceded by "EC". The first number broadly classifies the enzyme based on its mechanism.

The complete nomenclature can be browsed at http://www.chem.qmul.ac.uk/iubmb/enzyme/.

Accordingly, a peptide or protein of interest according to the present invention may be chosen from any of the classes EC 1 (Oxidoreductases), EC 2 (Transferases), EC 3 (Hydrolases), EC 4 (Lyases), EC 5 (Isomerases), and EC 6 (Ligases), and the subclasses thereof.

In certain embodiments, the peptide or protein of interest may be an antibody. This may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include HC, Fab, Fv and F(ab')2, Fab', and the like. Also, the peptide or protein of interest may be an antibody light chain (LC) or heavy chain (HC). The group of antibody heavy chain comprises alpha ($\alpha$), delta ($\delta$), epsilon ($\epsilon$), gamma ($\gamma$), and mu ($\mu$) chains. The group of light chains comprises lambda ($\lambda$) and kappa ($\kappa$) chains.

The peptide or protein of interest may include modified amino acids (e.g., phosphorylated, glycated, etc.) and amino acid analogs, regardless of its size or function.

The term "IRES" as used herein is intended to mean internal ribosomal entry site. In general, an IRES sequence is a feature that allows eukaryotic ribosomes to bind and begin translation without binding to a 5' capped end. In certain embodiments the IRES region is derived from a virus, such as picornavirus, encephalomyocarditis virus, hepatitis C virus IRES sequence. In various embodiments, the IRES sequence is chosen from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus.

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

The inventors of the present application surprisingly found that in the field of recombinant protein production, e.g., antibody production, as compared to co-transfection and multi-promoter vectors, using the presently claimed nucleic acid molecules, e.g., comprised in a bicistronic vector or tricistronic vector, minimizes the number of non-expressing clones, enhances the productivity of the individual clones, and controls the product quality. These advantages are for example obtained when using the tricistronic vectors as discussed herein. The following features have been found to be advantageous: (1) expression of LC, HC, and selection marker in one transcript, (2) arrangement of LC as the first cistron and the HC as the second cistron where translation is driven by the IRES, and (3) use of a selectable marker which has lower selection capabilities compared to normal conditions/the wildtype selectable marker.

The use of a marker with reduced selection capabilities in a multicistronic, for example a bi- or tricistronic construct allows for increasing the selection pressure in the course of identifying transfectants which express the desired peptide or protein of interest.

"Multicistronic", as used herein, relates to constructs comprising two or more, for example 2, 3, 4 or more, cistrons.

There are numerous options how to attenuate a selectable marker. For example, in one embodiment, the marker may be attenuated by addition of agents which inactivate the marker, for example inhibitors that interfere with an enzymatic function of the marker. These inhibitors may be other proteins as well as small molecules. For example, if DHFR is used as a selectable marker, MTX may be used to inhibit DHFR function. However, when such an agent that inactivates the marker is used, its concentration is selected such that it does not completely abolish marker function, as at least a certain degree of selectivity by means of the marker has to be retained.

Alternatively or in addition, the translation of a marker may be reduced by using a non-ATG start codon, non-optimal codons, sequences 5' of the maker sequence which form structures on RNA level which hamper the translation, mutants of the selectable marker which lower the activity of the marker. Also IRES sequences which have a sequence with lowered ribosome binding affinity compared to the wildtype sequence may be employed. These sequences reduce also the expression of the marker. Any combination of these strategies is possible in artificial selection of transformed/transfected cells. For example, impaired IRESatt (SEQ ID NO:30) driven translation may be combined with a weakened mutant of NPT for selection.

In addition, the use of a bi- or tricistronic vector ensures that all gene products encoded by the vector are expressed in a constant ratio towards each other. Furthermore, in case stable transfection is desired, the selection of clones expressing all encoded peptides/proteins is facilitated, because only one promoter is present. As disclosed in the Examples, using tricistronic vectors due to tight coupling of the three genes in one transcript the number of transfected, non-expressing clones is minimized, e.g., to 25%, as compared to 50 to 60% observed in those generated using Co-transfection and Multi-promoter vectors.

To enhance production stability, the tricistronic vector can be designed to use two different IRES elements and the inclusion of insulators, CpG island elements, or matrix attachment regions which have been reported to be able to prevent DNA methylation.

By avoiding gene amplification and enhancing stringency of selection, the herein disclosed optimized nucleic acid molecules, e.g., tricistronic vectors, enable generation of stably transfected cell pools which can produce recombinant antibodies with titers over 150 mg/L within two months. Furthermore, clones with specific antibody productivities greater than 30 pg/cell/day can be selected from only 100 clones in less than 6 months. Thus, the time for monoclonal protein production can be significantly reduced. In particular, the timeline can be further shortened by carrying out a drug selection and clone screening directly under protein-free conditions. Fast generation of mAb is critical to the different stages of mAb development. High producing pools can be quickly generated to provide mAb for preclinical studies, where only small amounts of mAb are needed and timing is great importance. In parallel, high producing clones can be picked for mAb production for late stage clinical trials and large scale manufacturing where high productivity is more critical. As compared to the use of transient transfection technology, use of stable pool for preclinical studies is preferred as product quality between stable pool and clones picked is more consistent Furthermore, the above described tricistronic vectors allow for expression of two peptides or proteins of interest, e.g., LC and HC, in a single transcript and thus enables the control of the expression ratio between the two peptides or proteins of interest, e.g., the LC:HC ratio. This gives a consistent product patterns for all clones. For example, without a strict control of LC:HC expression, as in Co-transfection and Multi-promoter, the generated clones could produce either full mAb, HC fragments, LC fragments, or a mixture of them.

In addition, the data show that a consistent ratio of the expressed peptides or proteins of interest also influences their posttranslational modification. For example, a fixed LC:HC expression ratio leads to a consistent glycan distribution of the resulting which resembles the glycosylation of the commercially available and clinically approved mAb. Without wishing to be bound by any theory, it is believed that that glycosylation is affected by the protein folding and assembly process, which in turn is affected by the peptide or protein of interest ratio, e.g., the LC:HC ratio.

As IRES-driven gene translation efficiency is several folds lower than that of cap-dependant translation, placement of two peptides or proteins of interest, e.g., LC and HC, either in the first cistron of a tricistronic vector determines which peptide or protein is expressed in excess. In certain embodiments it is advantageous to place a certain peptide or protein of interest in the first cistron, to achieve excess of this entity over the peptide or protein of interest placed in the second cistron. For example, excess LC is more desirable for mAb production than excess HC, the LC-IRES-HC arrangement leads to higher mAb expression than the HC-IRES-LC configuration. Extra expression of LC may be also beneficial for minimization of mAb aggregation. Also, for purification purposes, excess of LC over HC may be beneficial, e.g., if mAbs are to be purified using an antibody which is directed against the HC.

The data show that the ratio of LC:HC affects both mAb expression level and quality.

Furthermore, a weakened selection marker allows enhancing selection for high producers. Generally, the weaker the selection marker, the higher the threshold expression level required for clones to survive selection. The tricistronic design makes this strategy more effective as non-expressing clones can be minimized. The combination of attenuated IRES sequences controlling attenuated selectable markers further improves the selection of high producing clones.

Thus, the present invention relates in a first aspect to a nucleic acid molecule comprising at least one nucleic acid sequence encoding for a peptide or protein of interest, at least one nucleic acid sequence encoding for a selectable marker, and at least one IRES sequence, wherein the at least one IRES sequence is located between the at least one nucleic acid sequence encoding for the peptide or protein of interest and the at least one nucleic acid sequence encoding for the selectable marker, and the at least one nucleic acid sequence encoding for a selectable marker has a reduced translation efficiency and/or the encoded selectable marker is mutated such that it has a lowered activity compared to its wildtype variant and/or the at least one IRES sequence is located 5' to a nucleic acid sequence encoding for a selectable marker and is mutated such that it has a reduced ribosome binding affinity compared to the corresponding wildtype IRES sequence wherein the at least one IRES sequence comprises or consists of a nucleic acid sequence selected from the group of nucleic acid sequences set forth in SEQ ID NO:02-57 and 83-112.

As used herein, the term "selectable marker" is typically used to refer to a gene and/or protein that very generally confers a trait suitable for artificial selection, i.e. the presence or absence of which can be detected directly or indirectly in a cell. Examples for such markers include, but are not limited to a gene and/or a protein that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein and derivatives, luciferase, or alkaline phosphatase).

The selectable marker enables discrimination of cells, which may or may not contain said selectable marker. For example, a selectable marker may be the expression of a specific molecule, i.e. a reporter molecule, a resistance marker, like a marker conferring drug resistance to a cell, etc. The selection marker allows for simpler preparation, manufacturing, characterization or testing of the cell or cell line. The reporter gene or reporter molecule refers to a typical reporter or marker known in the art. For example, said reporter gene may be a gene encoding GFP or other marker molecules known in the art, like cellular and extracellular expression markers. Also, a selection marker may be a gene and/or a protein that inactivates a selection agent and protects the host cell from the agent's lethal or growth-inhibitory effects (e.g., an antibiotic resistance gene and/or protein), a gene and/or a protein which rescues a host being incapable of survival or growth under certain environmental conditions, e.g., if being cultivated in minimal culture medium, a gene encoding an enzyme which catalyzes a detectable reaction or which supplements the host's metabolism and allows growth under selection conditions, or a beta galactosidase, a secreted alkaline phosphatase, fluorescence markers, or cell surface markers. That is, the reporter groups are in general groups that make the introduced cell line distinguishable from the non-transfected cell line. This distinction can be made by selecting the reporter gene from the group of directly or indirectly detectable groups. Directly detectable groups are for example fluorescent compounds, like fluorescein or its derivatives, such as hexachlorofluorescine and hexafluorofluorescine, or fluorescent particles. Of course, other markers may be used, like radioactive isotopes of carbon, hydrogen, nitrogen, etc. In certain embodiments, the selection marker induces cell survival or cell growth and thus the transfected cells comprising the selection marker can be distinguished from non-transfected cells by monitoring the expansion of the cell culture.

In certain embodiments, the selectable marker is a nucleic acid sequences selected from the group consisting of sequences encoding for a fluorescent protein, GFP, an enzyme, a luciferase, a peroxidase, an antibiotic resistance gene, neomycin phosphotransferase, dihydrofolate reductase, glutamine synthetase (GS), puromycin-N-acetyl transferase, and the Sh ble gene.

A common strategy to obtain high producing cell lines is through amplification of gene copies by using amplifiable selection markers coupled with a corresponding amplification reagent, such as DHFR/methotrexate and glutamine synthetase (GS)/methionine.

The term "activity" as used herein shall be understood as a measure for the ability of a transcription product or a translation product to produce a biological effect or a measure for a level of biologically active molecules. The term "activity" also refers to enzymatic activity.

The terms "level" and/or "activity" as used herein further refer to gene expression levels or gene activity. Gene expression can be defined as the utilization of the information contained in a gene by transcription and translation leading to the production of a gene product. A gene product comprises either RNA or protein and is the result of expression of a gene. The amount of a gene product can be used to measure how active a gene is. The term "gene" as used in the present specification and in the claims comprises both coding regions (exons) as well as non-coding regions (e.g. non-coding regulatory elements such as promoters or enhancers, introns, leader and trailer sequences). The term "fragment" as used herein is meant to comprise e.g. an alternatively spliced, or truncated, or otherwise cleaved transcription product or translation product. A "modified version" of a gene can be understood as a fragment of a gene, or an alternative splice variant, or a gene comprising a modified nucleic acid sequence, said modified nucleic acid sequence comprising deletions, insertions, inversions, or mutations. The term "derivative" as used herein refers to a mutant, or an RNA-edited, or a chemically modified, or otherwise altered transcription product, or to a mutant, or chemically modified, or otherwise altered translation product. For instance, a "derivative" may be generated by processes such as altered phosphorylation, or glycosylation, or lipidation, or by altered signal peptide cleavage or other types of maturation cleavage. These processes may occur post-translationally. The term "modulator" as used in the present invention and in the claims refers to a molecule capable of changing or altering the level and/or the activity of a gene, or a transcription product of a gene, or a translation product of a gene. Preferably, a "modulator" is capable of changing or altering the biological activity of a transcription product or a translation product of a gene. Said modulation, for instance, may be an increase or a decrease in enzyme activity, a change in binding characteristics, or any other change or alteration in the biological, functional, or immunological properties of said translation product of a gene.

In certain embodiments, the at least one IRES sequence of the nucleic acid molecule is mutated such that it has a reduced ribosome binding affinity compared to the corresponding wildtype IRES sequence.

The terms "binding affinity" and "affinity" as used herein interchangeably, relate to the level of attraction between molecular entities. Affinity can be expressed quantitatively as a dissociation constant (Kd) or its inverse, the association constant (Ka). The term "ribosome binding affinity" means the binding affinity of a ribosome in a host cell to another entity, for example an IRES sequence. As used herein, the term "at least one IRES sequence has a reduced ribosome binding affinity compared to the corresponding wildtype IRES sequence" means that a given IRES sequence is mutated in order to reduce the ribosome binding affinity of the IRES sequence relative to the corresponding wildtype IRES sequence. The ribosome binding affinity is reduced such that the relative binding to the IRES sequence is reduced but still significant binding occurs. Binding of a ribosome is significant if the ribosome is still binding to the IRES sequence and is capable to initiate the translation of the sequence which lies 3' to the IRES sequence. The skilled person is aware of suitable techniques to determine the translation of a protein which is under control of an IRES sequence. For example, the person skilled in the art may employ the luciferase assay, as described herein.

In some embodiments, the at least one IRES sequence is selected from the group of nucleic acid sequences set forth in SEQ ID NO:30-57 and 98-112.

In various embodiments, the nucleic acid molecule comprises two nucleic acid sequences encoding for a peptide or protein of interest and two IRES sequences, wherein the two nucleic acid sequences encoding for a peptide or protein of interest encode for two distinct peptides or proteins of interest.

In some embodiments, the nucleic acid molecule has the following 5' to 3' organization: A-B-C-D-E, A-B-E-D-C, or E-B-A-D-C, wherein A is a first nucleic acid sequence encoding for the first peptide or protein of interest, B is a first IRES sequence, C is a second nucleic acid sequence encoding for the second peptide or protein of interest, D is a second IRES sequence, and E is a nucleic acid sequence encoding for a selectable marker.

In certain embodiments, the nucleic acid molecule has the organization A-B-C-D-E and D has a reduced ribosome binding affinity compared to the corresponding wildtype IRES sequence or wherein D is selected from the group of sequences set forth in SEQ ID NO:30-57 and 98-112; or the nucleic acid molecule has the organization A-B-E-D-C and B has a reduced ribosome binding affinity compared to the corresponding wildtype IRES sequence or wherein B is selected from the group of sequences set forth in SEQ ID NO:30-57 and 98-112, or the nucleic acid molecule has the organization E-B-A-D-C and E has reduced translation efficiency and/or E has a lowered selection activity compared to its wildtype variant.

In some embodiments, the at least one selection marker is selected from the group consisting of a fluorescent protein, an enzyme, an antibiotic resistance gene, and an auxotrophic marker gene.

The term "auxotrophic marker gene" refers to a marker that is used to complement specific nutritional requirements in mutant strains which are auxotrophic for the nutrient in question due to the absence of a functional chromosomal copy of the marker gene. Examples for auxotrophic marker genes are dihydrofolate reductase (DHFR), glutamine synthetase (GS), and thymidylate synthase (TS).

In various embodiments, the selectable marker is selected from the group consisting of GFP, a luciferase, a peroxidase, neomycin phosphotransferase, dihydrofolate reductase, glutamine synthetase, puromycin-N-acetyl transferase, and the enzyme encoded by the Sh ble gene.

In certain embodiments, the nucleic acid sequence encoding for the at least one selectable marker is selected from the group of nucleic acid sequences set forth in SEQ ID NOs:62, 67-69 or wherein the nucleic acid sequence encoding for the at least one selectable marker encodes for a protein having a sequence as set forth SEQ ID NOs:63-66, 70-77.

In some embodiments, the nucleic acid molecule encoding for the selectable marker encodes for a selectable marker which is less active than its corresponding wildtype selectable marker, wherein the reduction in activity is by at least 10, 20, 30, 40, 50, 60, 70, 80, 90, 95, 97, 98, or 99% compared to the wildtype selectable marker.

Any suitable marker and IRES sequence disclosed herein may be subjected to mutagenesis in order to further improve the selectable maker function or to further attenuate the IRES sequence and thereby reduce the ribosome binding affinity towards the IRES sequence. Accordingly, also disclosed herein are mutants of IRES sequences and selectable markers.

The term "mutation" as used herein relates to a variation in the nucleotide and/or amino acid sequence of a given nucleotide sequence or protein and includes substitutions, deletions, truncations, and insertions. In one specific example, the mutation is a point mutation, i.e. the replacement of one or more nucleotides and/or amino acids in a given sequence. It is understood that if the term "mutation" is used in relation to a protein sequence, that the nucleotide sequence encoding the protein can comprise multiple mutations or modifications, including silent mutations that, for example, serve the purpose to increase expression efficiency (codon-optimization) without changing the amino acid sequence. In the present invention, the mutation is preferably the substitution of one or two amino acids by other amino acids. Alternatively or in addition, the nucleic acid molecule may comprise nucleotide exchanges which do not alter the encoded protein sequence, so called silent mutations. In some embodiments, the mutations, e.g., silent mutations increase the expression and/or secretion efficiency of the peptide or protein encoded by the nucleic acid molecule. Importantly, mutations may be induced throughout the nucleic acid molecule of the present invention. Thus, the mutations may not be limited to sequences encoding for a peptide or protein. Accordingly, also non-coding sequence stretches may be subjected to mutagenesis. This type of mutation also falls within the scope of the term silent mutation. The mutagenesis of non-coding sequences may be advantageous, e.g., for the achievement of an improved expression and/or secretion of a peptide or protein encoded by a different sequence stretch within the nucleic acid molecule.

The term "mutagenesis" as used herein means that the experimental conditions are chosen such that the amino acid naturally occurring at a given sequence position of a protein sequence can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis.

The term "random mutagenesis" means that no predetermined single amino acid (mutation) is present at a certain sequence position but that one of at least two different amino acids can be incorporated with a certain probability at a predefined sequence position during mutagenesis.

The natural coding sequence of a protein sequence, i.e. the respective gene segment of an enzyme, can be used as a starting point for the mutagenesis of the amino acid positions selected in the present invention. For the mutagenesis of the recited amino acid positions, the person skilled in the art has at his disposal the various established standard methods for site-directed mutagenesis (Sambrook, J. et al. (2001) Molecular Cloning: A Laboratory Manual, 3rd Ed., Cold Spring Harbor Laboratory Press, Cold Spring Harbor, N.Y.). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine, cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence (V=adenine, guanine, or cytosine); use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. Another possibility is the use of codons NDT or NDC (wherein D=adenine, guanine, or thymine) as this provides a 1:1 ratio between the number of codons and the encoded amino acids, thus reduces the screening effort, and leads to a balanced set of 12 polar, non-polar, aromatic, non-aromatic, hydrophilic and hydrophobic amino acid residues (Arg, Asn, Asp, Cys, Gly, His, Ile, Leu, Phe, Ser, Tyr, Val (Reetz M T et al., 2008, ChemBioChem, 21; 9(11):1797-804)).

In this respect it is noted that codons for other amino acids (than the regular 20 naturally occurring amino acids) such as selenocysteine or pyrrolysine can also be incorporated into a nucleic acid molecule of the present invention. It is also possible, as described by Wang, L. et al ((2001) Science 292, 498-500) or Wang, L., and Schultz, P. G. ((2002) Chem. Comm. 1, 1-11) to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2' deoxyguanosine or 6(2-deoxy-β-D-ribofuranosyl)-3,4-dihydro-8H-pyrimidino-1,2-oxazine-7-one (Zaccolo et al. (1996) J. Mol. Biol. 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, Ge L, Plückthun A, Schneider K C, Wellnhofer G, Moroney S E. (1994). Nucleic Acids Res 22, 5600-5607).

One possible strategy for introducing mutations in the selected positions is based on the use of two oligonucleotides, each of which is partially derived from one of the corresponding sequence stretches wherein the amino acid position to be mutated is located. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a protein library.

A multitude of established procedures are available for ligation and cloning (Sambrook, J. et al. (2001), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the peptide or protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a polymerase mutein. Mutations possibly occurring outside the segments of experimental mutagenesis are often tolerated or can even prove to be advantageous, for example if they contribute to an improved folding efficiency or folding stability of the mutated peptide or protein. Particularly, for long and difficult to amplify nucleic acid sequences the PCR-based mutagenesis protocol provided by Reetz and colleagues (Sanchis J et al., Appl. Microbiol. Biotechnol. 2008 November; 81(2):387-97) may be applied.

As used herein, the term "mutated amino acid residue" means an amino acid residue that differs from the amino acid residue in the same sequence position in the wild-type peptide or protein.

For certain peptides or proteins of interest, the natural gene or cDNA encoding for the peptide or protein comprises a 5'-sequence encoding a secretion signal peptide. In certain embodiments the nucleotide sequence encoding for this peptide is comprised in the DNA encoding for the peptide or protein of interest of the present invention. In other embodiments, this nucleotide sequence has been removed by means of genetic engineering. In further embodiments, this sequence has been replaced by a different sorting/secretion peptide or affinity tag. The choice of the replacement sorting/secretion peptide may depend on the host organism chosen for protein expression, the later purification, or the application of the peptide or protein of interest. In further embodiments, the sequence of the peptide or protein of interest has been N- and/or C-terminally truncated relative to the wildtype enzyme sequence. Accordingly, in certain embodiments the peptide or protein of interest comprises a deletion of at least one N-terminal amino acid relative to the wildtype enzyme sequence. In further embodiments, the peptide or protein of interest comprises a deletion of at least one C-terminal amino acid relative to the wildtype enzyme sequence. In alternative embodiments, the peptide or protein of interest comprises a deletion of at least one N- and/or C-terminal amino acid relative to the wildtype enzyme sequence. In certain embodiments, the peptide or protein of interest comprises a deletion of at least 10, 20, 30, 40, 50, or more N- and/or C-terminal amino acid relative to the wildtype peptide or protein sequence.

Mutagenesis can be achieved by site-specific mutation based on rational design or a random mutation. One possible approach is the use of error-prone PCR, which results in random point mutations over a selected range of sequence positions of the peptide or protein of interest. The error-prone PCR can be carried out in accordance with any known protocol such as the one described by Zaccolo et al. (1996) J. Mol. Biol. 255, 589-603. Other methods of random mutagenesis which are suitable for such purposes include random insertion/deletion (RID) mutagenesis as described by Murakami, H et al. (2002) Nat. Biotechnol. 20, 76-81 or non-homologous random recombination (NRR), as described by Bittker, J. A. et al. (2002) Nat. Biotechnol. 20, 1024-1029. Rational design may be especially employed, if the crystal structure or NMR structure of the peptide or protein of interest is available. One possibility may be to mutate amino acid residues which induce a rigid folding of the peptide or protein of interest or have in comparison to other amino acid residues a rather fixed position within the 3D structure.

In various embodiments, the nucleic acid molecule further comprises a nucleic acid sequence directly 5' to the nucleic acid sequence encoding the selectable marker that when expressed in a cell forms a secondary structure within the mRNA and causes a reduced translation efficiency of the sequence encoding the selectable marker.

The expression directly 5' to the nucleic acid sequence means that the nucleic acid sequence is either directly fused to the nucleic acid sequence encoding the selectable marker or 5' to the nucleic acid sequence encoding the selectable marker but separated by a further nucleic acid sequence. However, the expression directly 5' to the nucleic acid sequence encoding the selectable marker means that the sequence forming a secondary structure within the mRNA is not separated by a cistron from the nucleic acid molecule encoding the selectable marker.

The term "fused" in this context means that nucleic acid sequences, peptides or proteins are directly connected to each other or interconnected by one or more nucleic acids, amino acids, peptides or proteins, e.g., one or more protease cleavage sites and/or affinity tags, respectively.

In certain embodiments, the sequence being directly 5' to the at least one nucleic acid sequence encoding the selectable marker forms a secondary structure within the mRNA and causes a reduced translation efficiency of the sequence encoding the selectable marker is selected from the group consisting of sequences forming a hairpin and a sequence forming a stem-loop.

The term "hairpin" as used herein refers to a structure formed by intramolecular base pairing in a single-stranded polynucleotide ending in an unpaired loop (the "hairpin loop"). In various embodiments, hairpins comprise a hairpin loop protected by stems. For example, a hairpin can comprise a first stem region, a hairpin loop region, and a second stem region. The first and second stem regions can hybridize to each other and together form a duplex region. Thus, a stem region of a hairpin monomer is a region that hybridizes to a complementary portion of the same monomer to form the duplex stem of a hairpin. The term "hairpin loop" refers to a single stranded region that loops back on itself and is closed by a single base pair.

"Interior loop" and "internal loop," are used interchangeably and refer to a loop closed by two base pairs. The closing base pairs are separate by single stranded regions of zero or more bases. A "bulge loop" is an interior loop where one of the separated single-stranded regions is zero bases in length and the other is greater than zero bases in length.

The term "stem-loop structure" used herein is intended to mean the "stem" region is a double-stranded region formed by intramolecular base pairing, while the "loop" region is a single-stranded region.

In certain embodiments, the nucleic acid sequence has a modified codon usage and/or comprises a non-ATG start codon.

The group of non-ATG start codons includes, but is not limited to GTG, ACG, ATA, TTG, ATT, and CTG.

The term "codon usage" as used herein refers to the average frequencies of specific codons in the nucleotide sequence, e.g., highly expressed mammalian genes. Codon usage patterns for mammals, including humans can be found in the literature. In the nucleic acid molecules of the present invention, the codon usage can be altered to reduce the expression of a certain coding nucleotide sequence, e.g., of a nucleic acid sequence encoding a selectable marker. According to the codon usage of the host rare codons are chosen to encode the corresponding peptide or protein or selectable marker, thereby reducing the corresponding expression. This can be achieved by a reverse codon optimization.

The term "codon optimization" as it refers to genes or coding regions of nucleic acid molecules for transformation of various hosts, refers to the alteration of codons in the gene or coding regions of the nucleic acid molecules. to reflect the typical codon usage of the host organism without altering the polypeptide encoded by the DNA:

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

In some embodiments, the at least one selectable marker is a neomycin phosphotransferase having a reduced enzymatic activity which is lowered at least by 10, 20, 30, 40, 50, 60, 70, 80, 90, 95, 97, 98, or 99% compared to the wildtype enzyme.

In various embodiments, the nucleic acid sequence encoding for the neomycin phosphotransferase is selected from the group of sequences as set forth in SEQ ID NO:67-69 or wherein the nucleic acid sequence encoding for the neomycin phosphotransferase encodes for a protein having a sequence as set forth SEQ ID NOs:64-66, 70-77.

In certain embodiments, the at least one nucleic acid sequence encoding for the peptide or protein of interest is selected from the group of sequences consisting of sequences encoding for an antibody, an antibody fragment, an antibody light chain (LC), an antibody heavy chain (HC), an fab fragment, and a fusion protein comprising or consisting of an antibody light chain (LC), a protein2A, and an antibody heavy chain (LC).

The peptides or proteins encoded by the nucleic acid molecule of the present invention may comprise a protein 2A sequence or a Furin/protein 2A sequence. Specifically, fusion proteins encoded by the nucleic acid molecule of the present invention may comprise a linker between the two peptide or protein entities consisting of a protein 2A or Furin/protein 2A sequence.

In certain embodiments, the at least one protein of interest encoded by the nucleic acid molecule of the present invention comprises a sequence as set for in SEQ ID NO:58 or 60. In further embodiments the nucleic acid molecule encodes for a peptide or protein of interest comprising a sequence as set forth in SEQ ID NOs:59 or 61.

Accordingly, if a cistron comprised in the nucleic acid molecule encodes for a heavy and a light chain of an antibody, the two proteins may be fused together by a protein 2A or Furin/protein2A sequence, e.g., as set forth in SEQ ID NOs: 59 or 61.

In some embodiments, the two peptides or proteins of interest encoded by the two nucleic acid sequences encoding for a peptide or protein of interest a) interact with each other, and/or b) form a complex.

Peptides or proteins interact with each other if they have a detectable affinity towards each other.

Two or more peptides form a complex if they interact with each other and the affinity is so strong that the binding towards each other is irreversible without changing the environment of the complex.

In certain embodiments, the nucleic acid molecule has the following 5' to 3' organization:
a) A-B-C-D-E, wherein A is an antibody light chain, C is an antibody heavy chain, D has a reduced ribosome binding affinity compared to the corresponding wildtype IRES sequence or wherein D is selected from the group of sequences as set forth in SEQ ID NO:30-57 and 98-112, and E is a neomycin phosphotransferase having a sequence as set forth in SEQ ID NO:64-66, 70-77;
b) A-B-E-D-C, wherein A is an antibody light chain, B has a reduced ribosome binding affinity compared to the corresponding wildtype IRES sequence or wherein B is selected from the group of sequences set forth in SEQ ID NO:30-57 and 98-112, E is a neomycin phosphotransferase having a sequence as set forth in SEQ ID NO:64-66, 70-77, C is an antibody heavy chain;
c) E-B-A-D-C, wherein E is a neomycin phosphotransferase having a sequence as set forth in SEQ ID NO:64-66, 70-77 or is a dihydrofolate reductase, A is an antibody light chain, C is an antibody heavy chain, wherein E comprises a sequence with reduced translation efficiency and/or E has a lowered activity compared to its wildtype variant;
d) A-B-C-D-E, wherein A is an antibody heavy chain, C is an antibody light chain, D has a reduced ribosome binding affinity compared to the corresponding wildtype IRES sequence or wherein D is selected from the group of sequences as set forth in SEQ ID NO:30-57 and 98-112, and E is a neomycin phosphotransferase having a sequence as set forth in SEQ ID NO:64-66, 70-77;
e) A-B-E-D-C, wherein A is an antibody heavy chain, B has a reduced ribosome binding affinity compared to the corresponding wildtype IRES sequence or wherein B is selected from the group of sequences set forth in SEQ ID NO:30-57 and 98-112, E is a neomycin phosphotransferase having a sequence as set forth in SEQ ID NO:64-66, 70-77, and C is an antibody light chain; or
f) E-B-A-D-C, wherein E is a neomycin phosphotransferase having a sequence as set forth in SEQ ID NO:64-66, 70-77 or is a dihydrofolate reductase, A is an antibody heavy chain, C is an antibody light chain, and wherein E comprises a sequence with reduced translation efficiency and/or E has a lowered selection activity compared to its wildtype variant.

In various embodiments, nucleic acid molecule further comprises a promoter and a polyadenylation signal sequence.

The term "promoter", as used herein, refers to a DNA region which contains an initial binding site for RNA polymerase and facilitates the transcription of a particular gene downstream thereof. That is, a promoter is an untranslated nucleotide sequence, upstream of a coding region, to which RNA polymerase binds to initiate the transcription of a gene, and is typically located near the genes it regulate, on the same strand and upstream (towards the 5' region of the sense strand). A promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., an intrinsic region of a gene or 3' to the coding region of the gene.

The promoter may be a heterologous promoter. In a particular variant the promoter is a constitutive promoter. In another particular variant the promoter is an inducible promoter. A particular promoter according to certain embodiments of the invention confers an overexpression of one or more copies of the nucleic acid molecule. In preferred embodiments, the molecule(s) is overexpressed two times, more preferred 5 times, 10 times, 20 times, 50 times, 100 times, 200 times, 500 times, 1000 times, and most preferred 2000 or more times when compared to expression from endogenous promoter. For example, where the host cell is *Pichia pastoris*, suitable promoters include, but are not limited to, aox1, aox2, das, gap, pex8, ypt1, fld1, and p40; where the host cell is *Saccharomyces cerevisiae* suitable promoters include, but are not limited to, gall, mating factor a, cyc-1, pgk1, adh2, adh, tef, gpd, met25, galL, galS, ctr1, ctr3, and cup1. Where the host cell, for example, is a mammalian cell, suitable promoters include, but are not limited to CMV, SV40, actin promoter, rps21, Rous sarcoma virus genome large genome long terminal repeats (RSV), metallothionein, thymidine kinase or interferon gene promoter. The promoter further includes, but not limited to, simian virus 40 (SV40) promoter, mouse mammary tumor virus (MMTV) promoter, human immunodeficiency virus-long terminal repeat (HIV-LTR) promoter, moloney virus promoter, cytomegalovirus (CMV) promoter, epstein-barr virus (FBV) promoter, respiratory syncytial virus (RSV) promoter, RNA polymerase II promoter, β-actin promoter, human hemoglobin promoter, human muscle creatin promoter, and so on.

A "terminator" or 3' termination sequences are able to the stop codon of a structural gene which function to stabilize the mRNA transcription product of the gene to which the sequence is operably linked, such as sequences which elicit polyadenylation. 3' termination sequences can be obtained from *Pichia* or other methylotrophic yeast or other yeasts or higher fungi or other eukaryotic organisms. Examples of *Pichia pastoris* 3' termination sequences useful for the practice of the present invention include termination sequences from the aox1 gene, p40 gene, his4 gene and fld1 gene.

The term "operably linked" in the context of nucleic acid sequences means that a first nucleic acid sequence is linked to a second nucleic acid sequence such that the first nucleic acid sequence is placed in a functional relationship with the second nucleic acid sequence. For instance, a promoter sequence is operably linked to a coding sequence of a heterologous gene if the promoter can initiate the transcription of the coding sequence. In a further context, a sequence encoding for the first peptide or protein, e.g., an affinity tag and/or protease cleavage site, is linked such to a second sequence encoding for a peptide or protein, e.g., a peptide or protein of interest, that if the two sequences are translated a single peptide/protein chain is obtained. Alternatively, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "polyadenylation signal/sequence", as used herein, relates to a nucleic acid sequence that mediates the attachment of a polyadenine stretch to the 3' terminus of the mRNA. Suitable polyadenylation signals include the SV40 early polyadenylation signal, the SV40 late polyadenylation signal, the HSV thymidine kinase polyadenylation signal, the protamine gene polyadenylation signal, the adenovirus 5 EIb polyadenylation signal, the bovine growth hormone polyadenylation signal, the human variant growth hormone polyadenylation signal and the like.

In some embodiments, the nucleic acid molecule is comprised in a vector.

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial "artificial" chromosomes (BAC) and yeast "artificial" chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

The vectors of the present invention preferably (but not always) contain a selectable marker gene.

According to certain embodiments of the invention, there is also provided a vector for the transformation of a eukaryotic host cell, comprising one or more copies of one of the nucleic acid molecules characterized above or one or more copies of the expression cassette as characterized above.

The vectors of some embodiments of the present invention can also include an autonomous replication sequence (ARS). The vectors can also contain selectable marker genes which function in bacteria, as well as sequences responsible for replication and extrachromosomal maintenance in bacteria. In alternative embodiments the selection is conferred by auxothrophic markers. Examples of bacterial selectable marker genes include ampicillin resistance (ampr), tetracycline resistance (tetr), neomycin resistance, hygromycin resistance and zeocin resistance (zeoR) genes.

In a second aspect, the present invention relates to a host cell comprising a nucleic acid molecule as disclosed herein.

The term "cell" includes any cell, including bacteria, yeast, fungi, plant, insect, and mammalian cells, amongst others. In a preferred embodiment, the cell is a mammalian cell.

Host organisms containing the transfected nucleic acid fragments are referred to as "transfectant" or "recombinant" or "transfected" organisms.

The term "transfection" as used herein refers to the process of introducing nucleic acids into a host cell.

A "host cell" is intended to relate to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. The term "cell" or "host cell" used for the production of a heterologous glycoprotein refers to a cell into which a nucleic acid, e.g. encoding a heterologous glycoprotein, can be or is introduced/transfected. Such cells include both prokaryotic cells, which are used for propagation of vectors/plasmids, and eukaryotic cells.

In preferred embodiments, the host cell is a mammalian cell. Preferably, the cell is selected from, preferably immortalized, cell lines of hybridoma cells, myeloma cells, preferably rat myeloma cells and mouse myeloma cells, hamster cells, or human cells.

In some preferred variants thereof the cell is selected from, but not limited to, CHO cells, in particular CHO K-1 and CHO DG44, BHK cells, NSO cells, SP2/0 cells, HEK293 cells, HEK293EBNA cells, PER.C6 cells, COS cells, 3T3 cells, YB2 cells, HeLa cells, and Vero cells. In preferred variants the cell is selected from DHFR-deficient CHO cells, such as dhfr-CHO (Proc. Natl. Acad. Sci. USA, Vol. 77, p. 4216-4220, 1980) and CHO K-1 (Proc. Natl. Acad. Sci. USA, Vol. 60, p. 1275, 1968).

In some preferred embodiments, the host cell is an amphibian cell. Preferably, the cell is selected from, but not limited to, *Xenopus laevis* oocytes (Nature, Vol. 291, p. 358-360, 1981).

In some preferred embodiments, the host cell is an insect cell. Preferably, the cell is selected from, but not limited to, Sf9, Sf21, and Tn5.

In some preferred embodiments, the host cell is a plant cell. Preferably, the cell is selected from, but not limited to, cells derived from *Nicotiana tabacum*, the acquatic plant Lemna minor or the moss *Physcomitrella patens*. These cells are known as a system for producing polypeptides, and may be cultured also as calli.

In some preferred embodiments; the host cell is a lower eukaryotic cell. Lower eukaryotic cells according to some embodiments of the invention include, but are not limited to, unicellular, multicellular, and filamentous fungi, preferably selected from: *Pichia* sp. *Candida* sp. *Saccharomyces* sp., *Saccharomycodes* sp., *Saccharomycopsis* sp., *Schizosaccharomyces* sp., *Zygosaccharomyces* sp. *Yarrowia* sp., *Hansenula* sp., *Kluyveromyces* sp., *Trichoderma* sp, *Aspergillus* sp., and *Fusarium* sp. and Myceteae, preferably selected from Ascomycetes, in particular *Chysosporium lucknowense*, and Basidiomycetes, in particular *Coniphora* sp. as well as *Arxula* sp.

In some preferred variants thereof the cell is selected from, but not limited to, *P. pastoris, P. stiptis, P. methanolica, P. bovis, P. canadensis, P. fermentans, P. membranaefaciens, P. pseudopolymorpha, P. quercuum, P. robertsii, P. saitoi, P. silvestrisi, P. strasburgensis; P. finlandica, P. trehalophila, P. koclamae, P. opuntiae, P. thermotolerans, P. salictaria, P. guercuum, P. pijperi; C. albicans, C. amphixiae, C. atlantica, C. corydalis, C. dosseyi, C. fructus, C. glabrata, C. fermentati, C. krusei, C. lusitaniae, C. maltosa, C. membranifaciens, C. utilis; S. bayanus, S. cerevisiae, S. bisporus, S. delbrueckii, S. fermentati, S. fragilis, S. mellis, S. rosei;* Saccharomycodes *ludwigii*, Saccharomycopsis capsularis; Schizosaccharomyces pombe, Schizosaccharomyces octosporus, Zygosaccharomyces bisporus, Zygosaccharomyces mellis, Zygosaccharomyces rouxii; Yarrowia fipolytica, Hansenula polymorpha, Kluyveromyces sp., Trichoderma reseei., A. nidulans, A. candidus, A. carneus, A. clavatus, A. fumigatus, A. niger, A. oryzae, A. versicolor, Fusarium gramineum, Fusarium venenatum*, and *Neurospora crassa* as well as *Arxula adeninivorans*.

If a genomic sequence of interest is known, one may identify such gene simply by searching publicly available DNA databases, which are available from several sources such as NCBI, Swissprot etc. For example, by searching a given genomic sequence or data base with a known gene from *S. cerevisiae*, one can identify genes of high homology in such a genome, which with a high degree of certainty encodes a gene that has a similar or identical activity. For example, homologues to known mannosyl transferases from *S. cerevisiae* in *P. pastoris* have been identified using either one of these approaches; these genes have similar functions to genes involved in the mannosylation of proteins in *S. cerevisiae* and thus their deletion may be used to manipulate the glycosylation pattern in *P. pastoris* or any other fungus with similar glycosylation pathways.

Some embodiments of the present invention also relates to genetically engineered cells where at least one endogenous enzyme activity is lacking or is being ineffective due one or more means, selected from suppression by inversion, suppression by antisense constructs, suppression by deletion, suppression on the level of transcription, suppression on the level of translation and other means. These are well known to a person skilled in molecular biology.

In some embodiments, the nucleic acid molecule is integrated in the genome of the host cell, whereas in other embodiments, the nucleic acid molecule is comprised in a vector being within a host cell.

The invention also provides, in some embodiments, respective means for direct genetic integration. The nucleotide sequence according to certain embodiments of the invention, encoding the protein to be expressed in a cell may be placed either in an integrative vector or in a replicative vector (such as a replicating circular plasmid). Integrative vectors generally include serially arranged sequences of at least a first insertable DNA fragment, a selectable marker gene, and a second insertable DNA fragment. The first and second insertable DNA fragments are each about 200 nucleotides in length and have nucleotide sequences which are homologous to portions of the genomic DNA of the species to be transformed. A nucleotide sequence containing a structural gene of interest for expression is inserted in this vector between the first and second insertable DNA fragments whether before or after the marker gene. Integrative vectors can be linearized prior to yeast transformation to facilitate the integration of the nucleotide sequence of interest into the host cell genome.

In another aspect, the present invention relates to a method for expression of at least one recombinant peptide or protein of interest, wherein the method comprises:
  (a) cultivating a host cell as disclosed herein in a culture medium under conditions that allow expression of the at least one recombinant peptide or protein of interest; and optionally
  (b) purifying the at least one recombinant peptide or protein of interest.

In various embodiments, the nucleic acid molecule encodes at least two recombinant peptides or proteins of interest and the method further comprises a step (c) of cultivating the host cell in a culture medium under conditions that allow expression of the at least two recombinant peptides or proteins of interest.

The term "expression", as used herein, refers to the transcription and stable accumulation of sense (mRNA) or antisense RNA derived from the nucleic acid fragment of certain embodiments of the invention. Expression may also refer to translation of mRNA into a polypeptide.

In certain embodiments, the at least two recombinant proteins are an antibody light chain (LC) and an antibody heavy chain (HC).

In a further aspect, the present invention relates to a nucleic acid molecule comprising or consisting of a nucleic acid sequence as set forth in SEQ ID NOs: 03-29, 31-57, and 83-112 and complements and fragments thereof.

In another aspect, the present invention relates to a nucleic acid molecule comprising: A: at least one nucleic acid sequence encoding for a selectable marker, B: a first IRES sequence, C: a first nucleic acid sequence encoding for a first recombinant peptide or protein of interest, D: a second IRES sequence, and E: a second nucleic acid sequence encoding for a second recombinant peptide or protein of interest, wherein the 5' to 3' organization of the nucleic acid molecule is A-B-C-D-E.

In some embodiments, a) the at least one selectable marker is selected from the group consisting of GFP, a luciferase, a peroxidase, neomycin phosphotransferase, dihydrofolate reductase, glutamine synthetase, puromycin-N-acetyl transferase, and the enzyme encoded by the Sh ble gene, and/or b) the first recombinant protein is an antibody light chain (LC) and the second recombinant protein is an antibody heavy chain (HC), or c) the first recombinant protein is an antibody heavy chain (HC) and the second recombinant protein is an antibody light chain (LC).

In a further aspect, the present invention relates to a method for expression of at least one recombinant peptide or protein of interest, wherein the method comprises:
(a) cultivating a host cell comprising a nucleic acid molecule as disclosed herein, wherein the host cell is cultivated in a culture medium under conditions that allow expression of the at least one recombinant peptide or protein of interest, and
(b) supplementing the culture medium with an inhibitor which increases the selection pressure on the host cell, and optionally
(c) purifying the at least one recombinant peptide or protein of interest.

In another aspect, the present invention relates to a method of differentially expressing an at least bicistronic nucleic acid construct, wherein the at least bicistronic construct comprises at least one first nucleic acid sequence encoding for a first recombinant peptide or protein of interest, at least one second nucleic acid sequence encoding for a second recombinant peptide or protein of interest, and at least one IRES sequence, wherein the at least one IRES sequence is located between the at least one first nucleic acid sequence encoding for the first recombinant peptide or protein of interest and the at least one second nucleic acid sequence encoding for the second recombinant peptide or protein of interest, wherein the first and the second recombinant peptide or protein of interest interact with each other and/or form a complex, and the at least bicistronic construct is comprised in a host cell which has been transformed with the nucleic acid molecule, and the method comprises cultivating the host cell in a culture medium suitable for expressing the first and the second recombinant peptide or protein of interest, wherein the at least one IRES sequence comprises or consists of a nucleic acid sequence selected from the group of nucleic acid sequences set forth in SEQ ID NO:03-29, 31-57, and 83-112 and optionally the first recombinant peptide or protein is an antibody light chain and the second recombinant protein is an antibody heavy chain.

In certain embodiments, an antibody light chain is a HER2 antibody light chain, preferably having a protein sequence as set forth in SEQ ID NO:79. In some embodiments, the antibody light chain is encoded by a nucleic acid sequence having the sequence set forth in SEQ ID NO:78.

In various embodiments, an antibody heavy chain is a HER2 antibody heavy chain, preferably having a protein sequence as set forth in SEQ ID NO:81. In some embodiments, the antibody heavy chain is encoded by a nucleic acid sequence having the sequence set forth in SEQ ID NO:80.

In some embodiments, DHFR is encoded by the sequence set forth in SEQ ID NO:82.

In various embodiments, the present invention relates to monospecific antibodies and/or bispecific antibodies. Bispecific antibodies comprise two distinct LC and two distinct HC. Accordingly, the present invention comprises vectors encoding such antibodies and methods of their production. In particular, such vectors comprise the attenuated selectable markers and attenuated selectable IRES sequences disclosed herein.

The term "attenuated" in the context of this invention means that a marker or peptide or protein has reduced translation efficiency and/or activity. In connection with IRES sequences, the term "attenuated" means that the IRES sequence has reduced ribosome binding affinity.

As will be apparent to the skilled person in the art, in certain embodiments the sequences disclosed herein may require 5' an additional start and/or a 3' stop codon. In further embodiments, the sequences disclosed herein may require the absence of the 5' start and/or 3' stop codon.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

EXAMPLES

Materials & Methods

Cloning Procedures

The Co-transfection vectors (FIG. 1A) were constructed by insertion of anti-HER2 LC (SEQ ID NO:78) and HC (SEQ ID NO:80) cDNA between EcoRI and XhoI sites in pcDNA3.1 (+) (Invitrogen). The nucleic acid sequences encode for the protein sequences set forth in SEQ ID NOs, 79 and 81. The Multi-promoter vector (FIG. 1B) was constructed based on an in-house dual-CMV vector expressing anti-HER2 described previously (Yang et al., 2009) by insertion of SV40-NPT-SpA cloned from pcDNA3.1(+) downstream of HC expression cassette using BstZ17I and PciI sites. Construction of the Tricistronic vectors (FIG. 1C) were based on pcDNA3.1(+). The region between the bovine growth hormone polyadenylation signal and SV40 promoter was replaced with an attenuated IRES (IRESatt) from encephalomyocarditis virus (EMCV) using XbaI and BsaBI sites. The IRESatt (SEQ ID NO:2) was cloned from pIRES-DsRed (ClonTech, Palo Alto, Calif.) based on the design described previously, in which both ATG-11 and ATG-12 were mutated and the start codon of NPT (coding sequence SEQ ID NO:62) was displaced 43 bases downstream of ATG-10 (Rees et al., 1996). Also, a SgrAI site was included at the 5' end of IRESatt during cloning. The anti-HER2 LC or HC cDNA was then inserted downstream of the human cytomegalovirus promoter (CMV) using BamHI and XbaI, followed by insertion of IRESwt-HC or IRESwt-LC element using XbaI and SgrAI site. The IRES-HC and IRES-LC element consists of the wild type EMCV IRES (IRESwt) cloned from pIRES-DsRed vector (ClonTech) and the anti-HER2 HC or LC cDNA. They were linked by overlapping PCR, with ATG-12 of the IRESwt as the start codon of HC or LC cDNA. The NPT mutants, M1 and M10, were generated using QuickChange site-directed mutagenesis kit (Stratagene, La Jolla, Calif.) as described previously study (Sautter, K and Enenkel, B (2005). Biotechnol Bioeng 89(5): 530-538), with amino acid E at 182 changed to D in M1, or D at 261 changed to G in M10. All restriction enzymes used were purchased from New England Biolabs (Ipswich, Mass., USA).

Construction of the dual-luciferase vectors for evaluating the strength of mutated encephalomyocarditis virus (EMCV) IRES (Genebank accession number: X74312, version X74312.1 GI:396509, SEQ ID NO:1) variants were based on pcDNA3.1(+) vector (Invitrogen), as summarized in FIG. 1A. The region between the bovine growth hormone polyadenylation signal (BGH) and neomycin phosphorase (NPT) was replaced with a renilla luciferase gene (Rluc) using BamHI and BstBI sites. Rluc was cloned from a pRL-CMV vector (Promega, Madison, Wis., USA). A XhoI site was included in the 3' end primer during cloning. Then the wild type IRES (IRESwt) was inserted using XhoI and BstBI. The IRESwt was cloned from pIRES-DsRed (ClonTech, Palo Alto, Calif.). A HpaI site, a NanI site, and partial sequence of firefly luciferase (Fluc) from ATG to NarI site were included at the 3' end during cloning. Finally, the rest sequence of Fluc from NanI site to the stop codon was inserted using NarI and HpaI site. Fluc was cloned from pGL3 (Promega).

Figure 1B:
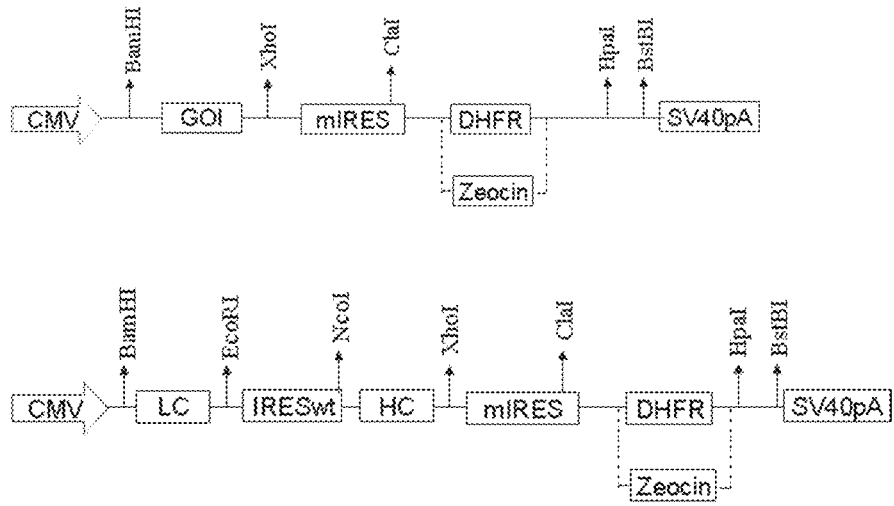

Vectors for evaluating mutated EMCV IRES for generation of stable cell lines were generated by replacing Fluc in the dual-luciferase vector with either dihydrofolate reductase (DHFR, e.g. SEQ ID NO:82) or Zeocin using ClaI and HpaI and by replacing Rluc with model product genes GFP or LC-IRESwt-HC, as shown in FIG. 1B. All restriction enzymes used were purchased from New England Biolabs (Ipswich, Mass., USA).

A series of EMCV IRES variants were generated by mutating ATG-10, ATG-11, ATG-12 to GTG, or deletion of sequences downstream of ATG-11 and/or ATG-10 (FIG. 1C). The IRESatt, commercially available, was cloned from pIRES-DsRed (ClonTech) based on the design described previously, in which ATG-11 was mutated and the start codon of selection marker was displaced 43 bases downstream of ATG-10 (Rees, Coote et al. 1996). Mutations of these variants were introduced to the 3' end of primer during cloning and inserted into the dual-luciferase vector to replace the IRESwt.

Furin/2a Constructs

Design of F2A: The 2A self-processing cleavage occurs between the last 2 amino acids at the C terminus of the 2A peptide (SEQ ID NO:59). The first protein upstream of 2A will have 23 additional amino acid residues at its C terminus after cleavage. To remove them, a furin cleavage site sequence (RRKR) was added to the 5' end of 2A peptide sequence resulting in a peptide having the sequence of SEQ ID NO:61.

Cell Culture and Media

Adherent CHO K1 cells (American Type Culture Collection, Manassas, Va.) were grown in the Dulbecco's modified Eagle's medium (DMEM+GlutaMax™, Invitrogen, Carlsbad, Calif.) supplemented with 10% fetal bovine serum (Sigma, St. Louis, Mo.) in a static humidified incubator with 5% CO2 at 37° C. Routine subculture was conducted every 3-4 days by detaching cells with 0.05% trypsin (Invitrogen), and diluting in 20 mL of fresh medium to $2\times10^5$ cells/mL in 75 cm$^2$ T-flasks.

Suspension CHO K1 and CHO DG44 cells (American Type Culture Collection) were obtained by in-house adaptation into a protein-free medium, prepared by mixing HyQ PF (HyClone, Logan, Utah) and CD CHO (Invitrogen) at a 1:1 ratio and supplemented with 1 g/L sodium carbonate (Sigma), 6 mM glutamine (Sigma), and 0.1% Pluronic F-68 (Invitrogen), designated as HyQCD. Also, 0.1 mM sodium hypoxanthine/0.016 mM thymidine (H/T, Giboco-Invitrogen) was supplemented to the HyQCD for CHO DG44 as it is dihydrofolate reductase (DHFR) deficient. Routine subculture was conducted every 3- to 4 days by diluting in 25 mL of fresh medium to $2\times10^5$ cells/mL in 125 cm$^3$ shake flasks in a humidified Kuner shaker (Adolf Kühner AG, Birsfelden, Switzerland) with 8% $CO_2$ at 37° C. Cell density and viability were determined by using the trypan blue exclusion method on an automated Cedex counter (Innovatis, Bielefeld, Germany).

Transient Transfections

Transient transfections were carried out in 6-well tissue culture plate (NUNC™, Roskilde, Denmark) using Fugene 6 (Roche, Indianapolis, Ind.). 24 h prior to transfection, 2 mL of adherent CHO K1 cells at exponential phase were seeded into each well at a cell density of $3\times10^5$ cells/mL. Transfection with appropriate mAb vectors was done in duplicates with Fugene 6 and DNA at a ratio of 6 µl:2 µg for each transfection. For the Co-transfection vector system (FIG. 1A), 1 µg of each LC and HC expressing plasmids was used. To normalize transfection efficiency, a third culture was co-transfected with 2 µg of corresponding mAb vectors and 0.2 µg of pMax-GFP (Amaxa, Gaithersburg, Md.) using 6 µL of Fugene 6 in parallel. At 48 h post-transfection, supernatant from cultures transfected with only mAb vectors was collected for analysis of mAb concentration using ELISA, and cells from cultures co-transfected with GFP were collected to measure the fluorescence intensity using a FACS Calibur (Becton Dickinson, MA, USA).

Transient transfections for evaluating the strength of EMCV variants were carried out in 96-well tissue culture plate (NUNC™, Roskilde, Denmark) using Fugene 6 (Roche, Indianapolis, Ind.). 24 h prior to transfection, 100 µL of adherent CHO K1 cells at exponential phase were seeded into each well at a cell density of $2\times10^5$ cells/mL. Each culture was co-transfected with 0.2 µg of the appropriate dual-luciferase vector by using 0.6 µL of Fugene 6.

Luciferase Assays

The luciferase activities of Fluc and Rluc were assayed by using Dual-Glo Luciferase Assay System (Promega, Madison, Wis.) on Tecan plate reader (Molecular Devices, Union City, Calif., USA). At 24 hr post-transfection, 75 µl of the Dual Glo™ luciferase reagent were added directly into cells grown in the 96-well culture plates and mixed well. The firefly luminescence was measured after 10 min incubation at room temperature. Subsequently, 75 µl of the Dual Glo™ Stop & Glo® reagent were added into each well and mixed well. After incubation for 10 min at room temperature, the renilla luminescence was measured.

Generation of Stable Cell Lines

Suspension CHO DG44 cells were used in evaluation of the Tricistronic vectors for mAb cell line generation. Transfections were carried out using electroporation on a Nucleofector (Amaxa, Gaithersburg, Md.) according to the manufacturer's instructions. In each transfection, $1\times10^7$ cells were transfected with 5 µg of plasmids linearized at BglII site. The transfected cells were then resuspended in 2 mL of protein-free HyQCD medium with HT supplemented in 6-well suspension culture plates (NUNC™). At 24 h post-transfection, they were diluted in 20 mL HyQCD medium with HT removed. Selection continued for 3 to 4 weeks to generate stably transfected pool. Gene amplification was induced by addition of 50 nM MTX to the selection medium. The higher degree of amplification was achieved by increasing MTX concentration in a stepwise manner to 100, 250, 500, 750, and 1000 nM.

Stable Cell Lines Comprising Mutated IRES Sequences

Suspension CHO DG44 cells were used in generation of stable cell lines for evaluation of mutated IRES on the DHFR and Zeocin selection marker, and suspension CHO K1 cells were used for evaluation on only Zeocin. Transfections were carried out using electroporation on a Nucleofector (Amaxa, Gaithersburg, Md.) according to the manufacturer's instructions. In each transfection, $1\times10^7$ cells were transfected with 5 µg of plasmids linearized at BglII site. The transfected cells were then resuspended in 2 mL of protein-free HyQCD medium without containing selection reagent preloaded in 6-well suspension culture plates (NUNC™). At 24 h post-transfection, they were collected by centrifuge at 1000 rpm for 5 minutes, then resuspended in 20 mL of selection reagent-containing HyQCD medium in 125 shake flasks (Corning Incorporated, Corning, N.Y.). H/T was removed if DHFR was used as the selection marker and Zeocin was added if Zeocin was used as the selection marker. Selection continued for 2 to 4 weeks and medium was changed every 3 to 4 day. Productivities of stable pools were determined in 250 mL shake flasks (Corning Incorporated, Corning, N.Y.) by seeding 50 mL of cultures at a cell density of $2\times10^5$ cells/mL. Mean fluorescence intensity of GFP expression at exponential phase was measured using FACS. Growth and mAb concentration in the supernatant were monitored every other day until viability dropped below 50%. The concentrations of mAb were measured using ELISA. The specific productivity was calculated as the mAb concentration measured at the end of culture divided by the integrated viable cell density. The integrated viable cell density was calculated using trapezoidal method.

Adherent CHO K1 cells were used in generation of stable cell lines for comparison of the Co-transfection, Multi-promoter, and tricistronic vectors containing the wild type NPT selection marker. Transfections were carried out using Fugene 6 as described in transient transfection. The plasmids were linearized using a unique BclI site prior to transfection. Selection with G418 (Sigma-Aldrich, St. Louis, Mo.) at 800 μg/mL in DMEM was started 48 h post-transfection. Non-transfected cells died after 7-10 days of selection and stably transfected pools were obtained in 2 to 3 weeks. Clones were isolated by limiting dilution in 96-well tissue culture treated plates (NCNC™, Roskilde, Denmark).

Suspension CHO K1 cells were used in generation of stable cell lines for evaluation of the improved tricistronic vector containing the NPT mutants. Transfections were carried out using electroporation on a Nucleofector (Amaxa, Gaithersburg, Md.) according to the manufacturer's instructions. In each transfection, $5\times10^6$ cells were transfected with 5 μg of plasmids linearized at BglII site. The transfected cells were then resuspended in 2 mL of protein-free HyQCD medium without containing selection reagent preloaded in 6-well suspension culture plates (NUNC™). At 24 h post-transfection, they were collected by centrifuge at 1000 rpm for 5 minutes, resuspended in 2 mL of DMEM+GlutaMax™ (Invitrogen, Carlsbad, Calif.) supplemented with 10% fetal bovine serum (Sigma, St. Louis, Mo.) and G418 at 800 μg/mL, and transferred to 6-well tissue culture plates (NUNC™). By changing media from protein-free to serum-containing medium, cells were rapidly switched from suspension to adherent. Selection continued for 4 to 5 weeks and clones were isolated using limiting dilution. The stable pools and high producing clones were then adapted back into the protein-free HyQCD medium containing G418 at 600 μg/mL by stepwise decrease of FBS from 10% to 1%, 0.5%, and 0%. Adaptation from adherent back to suspension cells took 1 to 2 months by using pre-adapted suspension cells in stable transfections, which is faster than using adherent cells.

ELISA Assay

The concentration of mAb in the supernatant was quantified using enzyme-linked immunosorbent assay (ELISA) in 96-well plate (NUNC). The plate was first coated with capture antibody of affinity purified goat antibody to human IgA+IgG+IgM (H+L) (KPL, Gaithersburg, Md., USA) in PBS at 37° C. for 1 hr. Following 3 washes with PBS buffer containing 1% albumin from bovine serum (BSA) (Sigma), 300 μL of blocking buffer (3% BSA in PBS) were added to each well and incubated at 37° C. for 1 hr. After an hour, the plate was washed as above. 50 μl of standard human affinity purified myeloma IgG1, kappa (Sigma) and diluted samples were added in duplicates and incubated at 37° C. for 1 hr. After another 3 washes, 50 μl of goat anti-human IgG (Fc specific) conjugated to alkaline phosphatase (Sigma) were added and incubated at 37° C. for 1 hr. After washing the plate again, 50 μL of FAST☐ p-Nitrophenyl Phosphate substrate (Sigma) were added and incubated at room temperature for 30 min. The reaction was stopped by 1M NaOH and absorbance at 405 nm (reference 630 nm) was measured on a Universal Microplate Spectrophotometer (Bio-TEK® Instruments, Winooski, Vt., USA).

Determination of Specific Productivity

Productivities of stable pools and clones under adherent condition were determined in 6-well tissue culture plates (NUNC™) by seeding 2 mL of culture in each well at a cell density of $2\times10^5$ cells/mL. At day 3, cells were detached by trypsin (Invitrogen) for analysis of cell density using Cedex counter (Innovatis) and supernatant was collected for analysis of mAb concentration using enzyme-linked immunosorbent assay (ELISA) as described previously (Yang et al., 2009). Productivities of stable pools and clones in suspension were determined in 250 mL shake flasks (Corning Incorporated, Corning, N.Y.) by seeding 50 mL of cultures at a cell density of $2\times10^5$ cells/mL. Growth and mAb concentration in the supernatant were monitored every other day until viability dropped below 50%.

The concentrations of mAb were measured using a nephelometric method on a Beckman Coulter Image system (Buckinghamshire, England) according to manufacturer's instructions. The specific productivity in both adherent and suspension cultures was calculated as the mAb concentration measured at the end of culture divided by the integrated viable cell density. The integrated viable cell density was calculated using trapezoidal method.

Western Blotting Analysis

The product pattern in different clones generated using Co-transfection, Multi-promoter, and different tricistronic vectors, e.g., vectors containing the wild type NPT selection marker, was determined using western blotting. 12 uL of supernatant from 6-well plate cultures were mixed with 4 uL of loading buffer, boiled for 10 min at 70° C., separated on a E-PAGE™ 48 protein Electrophoresis System, and transferred to PVDF membranes according to manufacturer's instructions. The E-PAGE™ 48 protein Electrophoresis System and all needed materials were purchased from Invitrogen. The membranes were blocked with 5% non-fat milk solution in PBS containing 0.1% Tween-20 (Sigma), probed with AffiniPure mouse anti-human IgG(H+L) polyclonal primary antibody followed by horseradish peroxidase (HRP)-conjugated goat anti-mouse IgG secondary antibody (Jackson ImmunoResearch, West Grove, Pa.). Proteins were detected using the Super Signal West Pico Chemiluminescent Substrate (Thermo Scientific). Membranes were exposed using Lumi-Film Chemiluninescent Detection Film (Roche).

Purification of mAb on Protein A Column

Culture supernatant containing mAb was loaded on a Tricorn 5/150 Protein A column packed with MabSelect SuRe (GE Healthcare, Uppsala, Sweden) using 1×PBS as a loading buffer and 0.1 M glycine buffer (Merck, Darmstadt, Germany) at pH 2.7 for elution. Samples were neutralized with 1 M sodium bicarbonate at pH 8 (Merck). The purification was performed using a GE AKTA explorer 100 (GE Healthcare) and a UV detection at 280 nm.

Production Stability Analysis

The clones generated using different Tricistronic vector were subjected to production stability studies during long term culture. For example, the top 5 producing clones generated using the Tricistronic vector that were selected based on qmAb were subjected to production stability studies during long term culture. The clones were thawed and maintained in 125 mL shake flasks with 25 mL of protein-free HyQCD medium with and without G418 selection pressure over 12 weeks. Passage was done every 3 to 4 days by diluting in 25 mL of fresh medium to $2\times10^5$ cells/mL. Growth and titer profiles as well as specific productivity were determined prior to stability testing and at week 12 in 125 mL shake flasks with 50 mL of corresponding medium as described above for suspension cultures.

Determination of Intracellular Polypeptides of LC:HC Ratios

The ratios of intracellular polypeptides LC:HC in clones generated using Co-transfection, Multi-Promoter, and tricistronic vectors containing the wild type NPT selection marker were determined based on ELISA. 2×6 cells collected from 6-well plate cultures were washed with 1×PBS (Sigma) and lysed in RIPA buffer (Thermo Scientific, Rockford, Ill.). The cell lysates were centrifuged at 14,000 rpm for 30 min at 4° C. The supernatants were quantified for concentrations of LC and HC polypeptides using ELISA as described previously (Yang et al., 2009), with goat anti-human IgG (Fc-specific) conjugated to alkaline phosphatase (Sigma) targeting HC and goat anti-human IgG (LC-specific) conjugated to alkaline phosphatase (Sigma) targeting LC, respectively. The ratio of intracellular LC:HC polypeptides in each clone was calculated as the measured concentration of LC over HC.

Glycosylation Analysis

The N-linked glycan distribution of mAb was analyzed using MALDI-TOF mass spectrometry. Culture supernatant containing mAb was loaded on a Tricorn 5/150 Protein A column (MabSelect SuRe, GE Healthcare, USA). IgG were eluted with 0.1 M glycine buffer (Merck) with pH at 2.7 and immediately neutralized with 1M sodium bicarbonate (Merck) with pH at 8. Subsequently, 200 µg of purified mAb was dissolved in a 50 mM ammonium bicarbonate buffer (Merck) with pH at 8.2 and incubated with 8 µg of trypsin (Sequencing grade modified trypsin, Promega Corporation, USA) for 4 hours at 37° C. The digestion was then stopped by heating at 95° C. for 15 minutes. The resulting mixture was deglycosylated by incubation with 70 U of PNGase F (Prozyme, USA) for overnight at 37° C. The released N-glycans were then purified using the GlycoClean H cartridges (GKI-4025) according to the manufacturer's instructions (Prozyme, USA). The N-glycan preparation was permethylated since permethylation modification has been commonly used to neutralize acidic glycans and erase the different ionization efficiency between neutral and acidic glycans (Harvey, 1993; Kang et al., 2007; Mechref and Novotny, 2002; Wada et al., 2007). This strategy allowed a relative quantification of the different N-glycan species based on the MALDI-MS data (Kang et al., 2007; Wada et al., 2007). This treatment has been performed using the sodium hydroxide procedure as described previously (Ciucanu and Kerek, 1984; Dell et al., 1994). After, the permethylated N-glycans were cleanup using Sep-Pack C18 cartridges (Waters Corporation, USA) according to the procedure described previously (North et al., 2010).

Aggregation Analysis

The aggregation of protein A purified mAb was investigated using dynamic light scattering detector, based on the hydrodynamic radius. The instrument setup consisted of a HPLC system (Shimadzu, Kyoto, Japan) operated by the Class VP software, with a binary pump, an auto injector, a thermostated column oven and a UV-visible detector. The Chromatography columns used were TSK Guard column SWXL, 6×40 mm and TSK gel G3000 SWXL, 7.8×300 mm (Tosoh Corporation, Tokyo, Japan). Column Oven temperature was set at 25° C. and mobile phase included 0.2M sodium phosphate (Merck) and 0.1M Potassium Sulfate Buffer (Merck, SEC Sulfate, pH~6.0). Flow rate was 0.5 mL·min$^{-1}$. Dawn 8 (light scattering), Optilab (refractive index), and QELS (dynamic light scattering), were connected in series following the UV visible detector. All the three detectors were purchased from Wyatt Technology Corporation and were operated by the ASTRA software (CA, USA).

Results

Generation of Mutated IRES with Varying Strength

EMCV IRES (cf. FIG. 3, SEQ ID NO:1) has three ATGs at the 3' end. It has been reported that ATG-11 is the dominant translation initiation site and that ATG-10 and ATG-12 can also be used. Sequences around ATG-10, ATG-11, and ATG-12 can affect which of the three ATGs is used as the translation initiation site and affect translation efficiency. In the following experiment, a set of mutated IRES sequences was generated by mutating one to three ATGs to GTG or deleting them and their surrounding sequences. The strength of each IRES sequence variant (SEQ ID NOs:2, 18-30, 46-57, 83-112) in inducing expression of a gene was determined using dual-luciferase vectors (FIGS. 1 and 2). Each dual-luciferase vector carries a Rluc and a Fluc gene. Both genes are under the control of the same CMV promoter. The Fluc gene is under control of the corresponding IRES sequence. The Fluc was used to report the strength of IRES variants and Rluc was used as an internal control to correct for the variability of transfection efficiency. The strength of each IRES variant was determined as the Fluc activity normalized to the Rluc activity and normalized to the control, the wild-type IRES (FIG. 1C). IRES sequences having a sequence as set forth in SEQ ID Nos:31-45 have also been analyzed.

Mutation of ATG-11 and insertion of extra bases between the start codon of Fluc and the IRES sequence, as in commercial IRESatt IRES sequence, reduced the strength to 6.9% of the IRESwt sequence. Among the tested IRES variants, IRES V10 to V20 (SEQ ID NO:57, 88-97, 103-112) showed further reduced strengths ranging from 5.9% to 0.

M6 (=mIRES6, SEQ ID NOs:23,51) with ATG-11 and ATG12 mutated to GTG and M7 (=mIRES7, SEQ ID NOs:24,52) with all three ATGs mutated to GTGs also reduced the strength to 10%. M9 (=mIRES9, SEQ ID NOs:25,53), M10 (=mIRES10, SEQ ID NOs:27,55), M12 (=mIRES12, SEQ ID NOs:29,57) exhibited further reduced strengths to about 2% by deletion of ATG-12 and ATG-11 together with mutations of one or two ATG to GTG. The sequence details experimental results are shown in and FIG. 2. Furthermore, it was found that the IRES sequence having a sequence as set forth in SEQ ID NO:37 is more strongly attenuated than the commercially available IRESatt sequence.

Construction of Tricistronic Vectors

To overcome the problems associated with separate expression design, meaning the use of two separate expression vectors, tricistronic vectors were designed to express the LC, HC and NPT (neomycin phosphotransferase) selection marker in one transcript under the control of one CMV promoter (cf. FIG. 4). Either LC or HC was arranged as the first cistron to obtain different ratios of LC:HC expression. EMCV IRES was applied on the second mAb gene. For higher translation efficiency, the sequence around ATG-10, ATG-11, and ATG-12 was maintained and ATG-12 was used as the start codon of mAb gene. Though three extra amino acids are added, it will not affect correct cleavage of the signal peptide and be cleaved of together with signal peptide. NPT instead of amplifiable selection markers, such as DHFR, was used to avoid gene amplification with the aim of reducing the cell line generation timeline. To enhance the stringency of selection for high producer, either IRESatt was applied on NPT to reduce its expression or used a combination of IRE-Satt and NPT mutants to further weakening its strength.

DILIH and DIHIL were constructed based on the tricistronic vectors containing NPT, with either LC or HC as the first cistron. IRESatt-NPT-SpA region was replaced with SpA, then addition of DHFR downstream of CMV promoter, respectively.

Evaluation of Tricistronic Vector for mAb Expression in Transient Transfections

The tricistronic vectors with these two designs, Tri-LIH and Tri-HIL, were compared with the Co-transfection and Multi-promoter vectors in transient transfections in CKO K1 cells (cf. FIG. 5). The Co-transfection and Multi-promoter vectors exhibited similar mAb expression levels. In contrast, both tricistronic vectors had lower expression, with Tri-LIH design 33% lower and Tri-HIL design 84% lower as compared to that from the Co-transfection system. As IRES-driven gene has lower translation efficiency. Arrangement of LC as the first cistron in the tricistronic vector leads to expression of LC in excess, and vice versa for the arrangement of HC as the first cistron.

Evaluation of Tricistronic Vector for mAb Expression in Stable Transfections

Figure 6A:
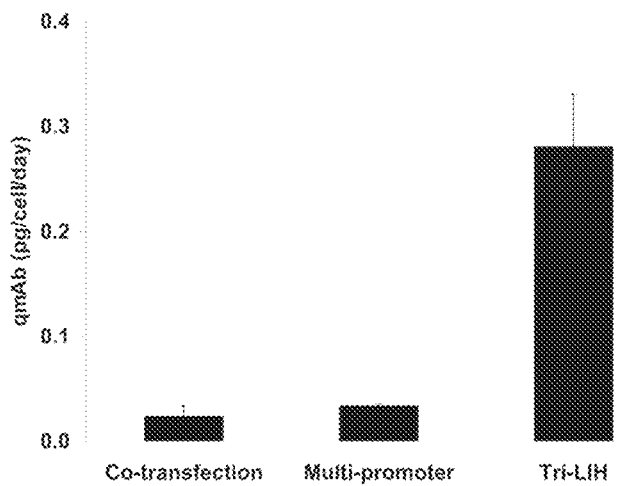
FIG. 6 shows a comparison of different vectors for mAb expression levels after stable CHO K1 cell transfection. A: Specific productivity in stably transfected pools. Each point represents the average and standard deviation of measurements of three transfected pools. B: Percentage of the expressing clones and specific productivity of expressing clones. The mAb concentration was determined using ELISA employing a detection antibody targeting the Fc region.
Figure 6B:
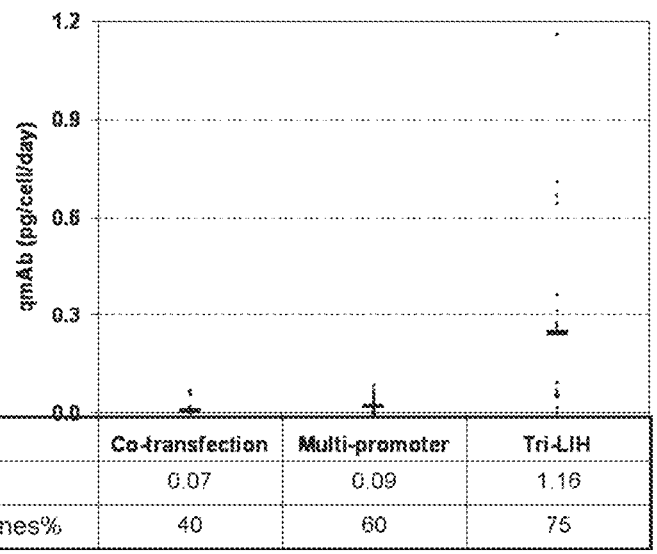

The tricistronic vector with the optimal arrangement, Tri-LIH, was then compared with the Co-transfection and Multi-promoter systems in stable transfections. For a correct comparison of the performance, the same selection marker, the wild type NPT, was used in all three vector system. In stably transfected pools, the Co-transfection and Multi-promoter vector systems gave similar specific productivities (qmAb), with 0.02 pg/cell/day and 0.03 pg/cell/day, respectively. In contrast to lower expression in transient transfections, the tricistronic vector enhanced stable pool expression levels by almost 10-fold, reaching 0.28 pg/cell/day (FIG. 6A). Among 20 clones randomly picked from stable pools generated by each of the three vector systems, 40% of clones generated by Co-transfection system and 60% of clones generated by Multi-promoter system produced detectable levels of mAb using ELISA with Fc-specific antibody for detection, while 75% of clones generated using the tricistronic vector were positive. The tricistronic vector also enhanced productivity of clones. The average qmAb of 20 clones from the tricistronic vector is 0.25 pg/cell/day and the highest producing clone had qmAb of 1.16 pg/cell/day compared to average qmAb of 0.01 pg/cell/day and highest qmAb of 0.07 pg/cell/day for Co-transfection system, and average qmAb of 0.02 pg/cell/day and highest qmAb of 0.09 pg/cell/day for the Multi-promoter system (cf: FIG. 6B).

The clones were then sorted in ascending order based on their qmAb from 1 to 20 for further analysis using western blotting. The supernatant collected from different clones was analyzed under non-reduced conditions. Besides complete antibody $HC_2LC_2$, antibody fragments including $LC_2$, LC monomer and $HC_2$ were observed in different clones (FIG. 7). Among 20 clones examined, only 2 clones generated using Co-transfection system and 4 clones generated using Multi-promoter system produced complete antibodies, the other clones produced mainly HC, LC fragments or no detectable antibody components. These results suggested that a portion of the positive clones detected using ELISA were false positive clones expressing mainly HC fragments. In contrast thereto, using the tricistronic vector for transfection, 15 out of 20 clones produced mainly complete antibodies and some LC dimmers and monomer.

Figure 8B:
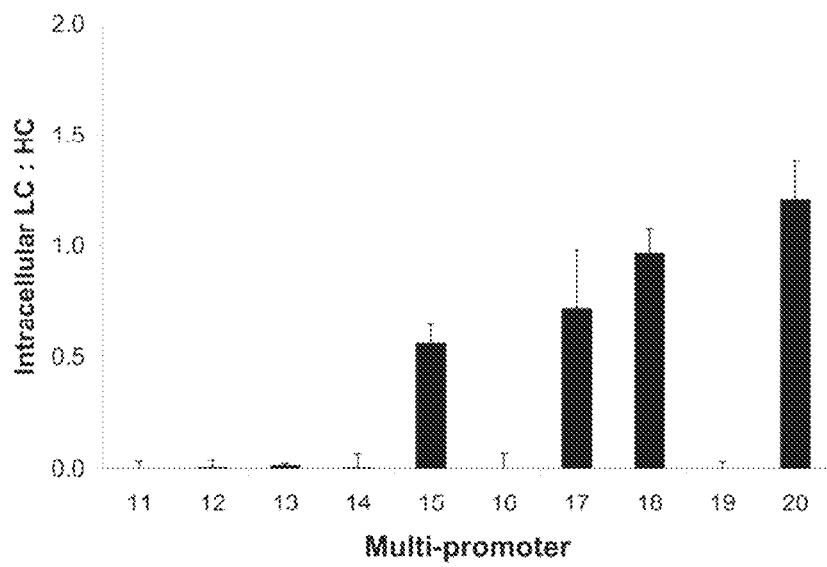
FIG. 8 shows the ratios of the intracellular abundance of LC over HC polypeptides obtained for different clones generated using (A) Co-transfection, (B) Multi-promoter, and (C) Tricistronic vectors. Equal numbers of cells were lysed in RIPA buffer. The concentration of LC and HC polypeptides in the lysates was determined by using ELISA, with detection antibody targeting LC and Fc region, respectively.
Figure 8C:
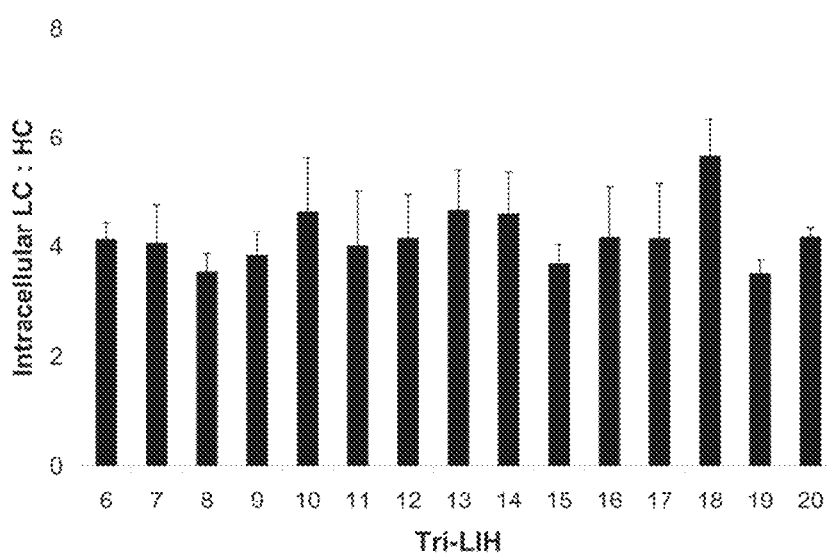

Further analysis of the ratios of intracellular abundance of LC over HC polypeptides explained why different product patterns were observed in clones generated using different vector systems. The intracellular product patterns (LC:HC rations) observed for clones generated using the Co-transfection and Multi-promoter systems varied from more than 7 to close to 0 (FIG. 8). In case the ratio was close to 1, as for Multi-promoter clones 15, 17, 18, and 20, the secreted product was mainly complete mAb. Expression of LC or HC in excess resulted in the secretion of mainly mAb fragments, like Co-transfection clone 9 and Multi-promoter clones 11 to 14. The tricistronic vector controlled the ratio of LC:HC polypeptides around 4:1 for all positive clones. This matched well with the consistent product pattern in all clones and explains the excess of secreted LC monomers and dimers.

Figure 9A:
FIG. 9 shows specific productivities of stably transfected cells generated using Tricistronic vectors with the wild type NPT (WT), mutant M1, mutant M10, and mutant M4 as selection markers. (A) The architecture of the tricistronic vectors is shown. Below, the table shows the nucleotide and amino acid substitutions and reported normalized enzyme activity for each mutant. The NPT mutants were generated based according to (Sautter, K and Enenkel, B (2005). Biotechnol Bioeng 89(5): 530-538). (B) Shows the specific productivities obtained for each construct. Each specific productivity point represents the average and standard deviation of measurements from three stably transfected cell pools. For M4 transfection, no viable clones were obtained.
Figure 9B:
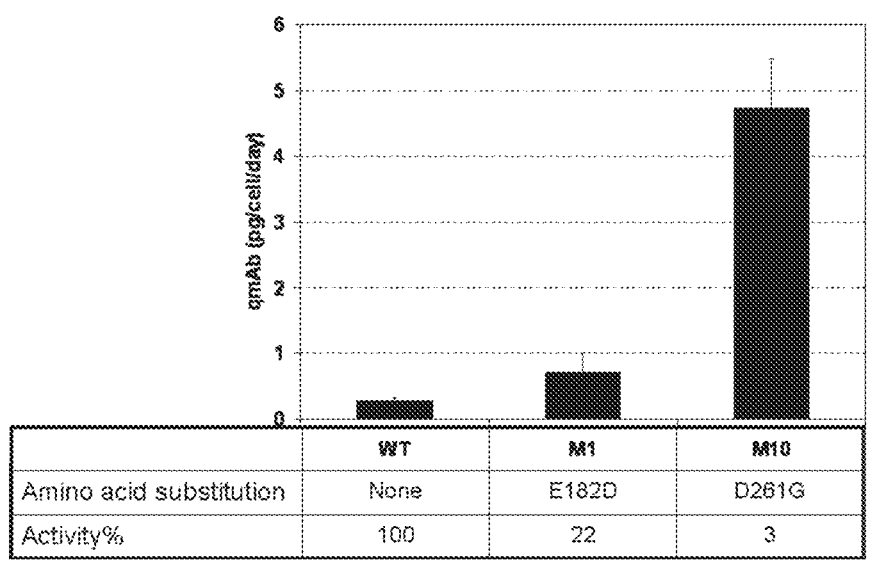
Figure 10:
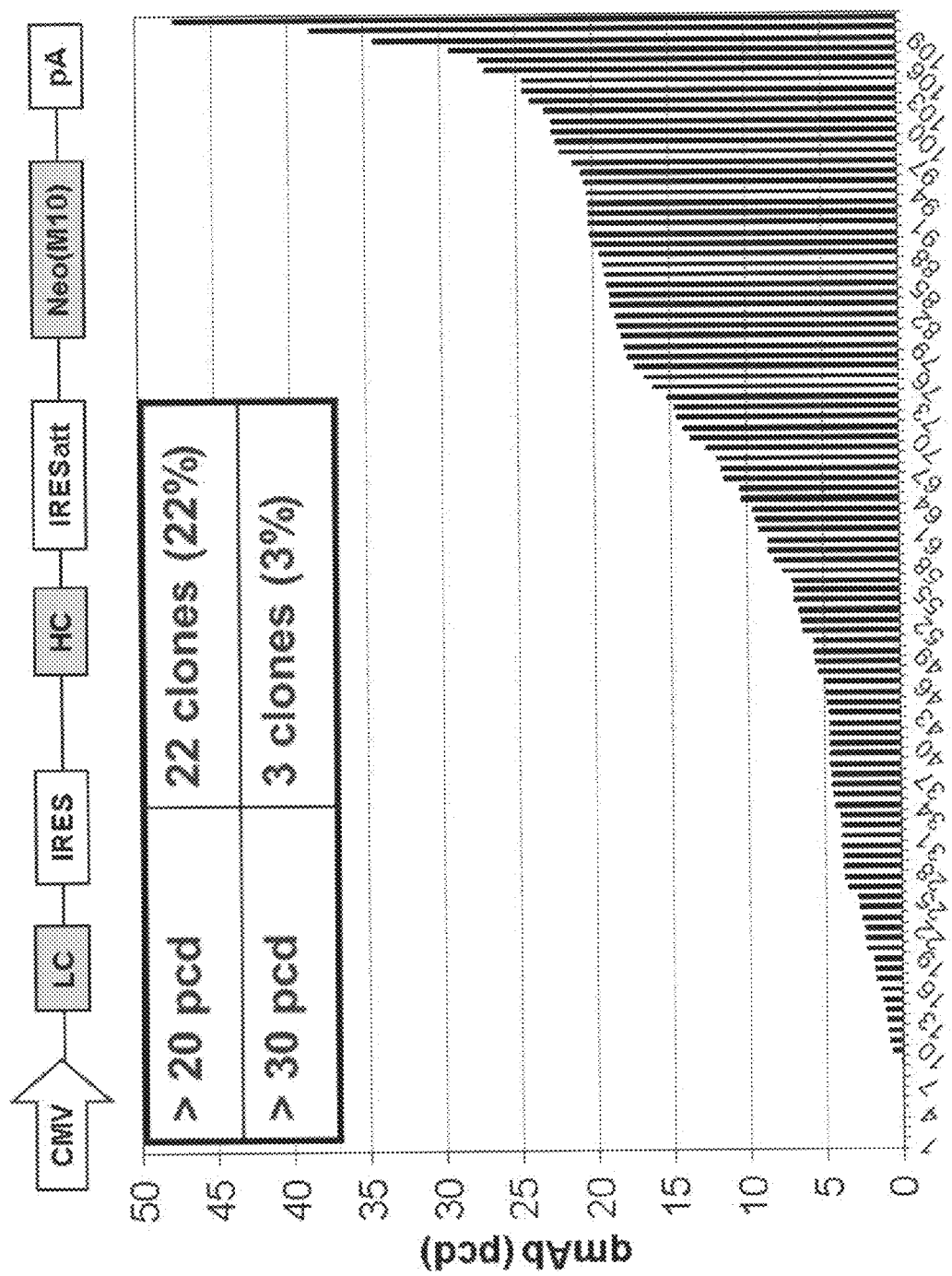
FIG. 10 shows a scheme of a tricicstronic construct which has been used for stable transfection of cells. This construct carries a gene encoding for the M2 mutant of the neomycin phosphotransferase. Below the results of an analysis of 111 clones of accordingly transfected cells are shown. After transformation, the cells were grown for 3 days in 6-well plates using DMEM+10% FBS as medium.

Weakening Selection Marker in Tricistronic Vector for Selection of High Producers Though tricistronic vector minimized non-expressing clones and enhanced productivity by expressing three genes in one transcript and applying the IRESatt on the wild type NPT, the highest expressing clone out of 20 picked had qmAb of only 1.16 pg/cell/day. To improve the efficiency of selection for high producers, the tricistronic vector was improved by further weakening selection marker through the use of NPT mutants, M1 (SEQ ID NOs:64, 67) and M10 (SEQ ID NOs:65, 68, cf. FIG. 9A). M1 and M10 mutations would reduce the enzymatic activity of NPT to 22% and 3% compared to the wild-type NPT (Sautter, K and Enenkel, B (2005). Biotechnol Bioeng 89(5): 530-538). In preliminary attempts at generating stable pools, about $5 \times 10^5$ attached CHO K1 cells were transfected with 2 μg of improved tricistronic vectors using Fugene 6. No clones survived selection in pools transfected with tricistronic vector containing the M10 mutant due to the high stringency of selection and low transfection efficiency. To address this issue, $5 \times 10^6$ suspended cells were transfected using electroporation to obtain more transfectants and selected for stable transfectants under adherent conditions. This protocol allowed the successful generation of stable pools. Thousands of clones survived the selection process after transfection with the tricistronic vectors carrying wild type NPT or the M1 mutant. In contrast thereto, only tens of clones transfected with the M10 tricistronic construct survived selection suggesting that the strength of NPT has been optimized to the lowest level for selection. As compared to the control tricistronic vector containing the wild type NPT, the improved tricistronic vector containing M1 mutant increased the qmAb of the stable pool by 2-fold to 0.72 pg/cell/day and using the even weaker M10 pushed qmAb higher to 4.73 pg/cell/day (cf. FIG. 9B). A stable pool generated using M10-containing vector was adapted to protein free suspension culture. The specific productivity was maintained at around 5 pg/cell/day after adaptation. The culture reached a peak cell density of 5.7e6 cells/mL and a titer of 168 mg/L in a 9 days batch shake flask experiment.

A total of 111 clones were randomly picked from the stable cell pool generated using the M10 tricistronic vector and were screened for high producing clones in 6-well plates. Based on the amount of qmAb measured, the top 20 clones were adapted to protein-free suspension conditions and characterized in shake flasks for growth and productivity. The results of the 5 clones with highest qmAb, clone 50, 63, 87, 97, and 98, are listed in Table 1 below. In non-optimized shake flask batch cultures using commercial protein-free medium, the 5 clones maintained viability above 50% for 7 to 9 days, with peak cell density ranging from $2.1 \times 10^6$ to $7.6 \times 10^6$ cells/mL. The specific productivity, calculated based on the entire culture process, ranged from 20 to 33 pg/cell/day and the maximal titer of the highest producing clone, 87, reached 513 mg/L. Productivities of these clones can be considered relatively high as the culture conditions were under non-optimized shake flask batch cultures using commercial available medium.

TABLE 1

Productivity of mAb in top expressing clones in shake flask batch culture. VCD represents viable cell density.

| Clone | Max. VCD (×10⁶ cell/mL) | Culture length (days) | Max. titer (mg/L) | qP (pg/cell/day) |
|---|---|---|---|---|
| 50 | 2.1 | 8 | 399 | 31 |
| 63 | 4.0 | 7 | 434 | 33 |
| 87 | 5.6 | 9 | 513 | 20 |
| 97 | 7.6 | 9 | 461 | 20 |
| 98 | 3.8 | 7 | 268 | 22 |

Production Stability of Clones Generated Using Improved Tricistronic Vector

Monoclonal antibody production stability tests were conducted for the 5 clones with the highest qmAb for 12 weeks, corresponding to 25 passages, in the presence and absence of G418. Table 2 below summarizes the maximal titer and qmAb prior to stability testing, designated as P0, and at the end of the stability testing at passage 25, designated as P25. Growth rates of all clones gradually increased during passaging regardless of with and without G418 (data not shown). Clone 50, 63, and 97 were unstable both in the presence and absence of G418 with maximal titer dropped by 41 to 72% and qmAb dropped by 50 to 85%. A good correlation exists between the drop in qmAb and the maximal titers, indicating that the loss in production was mainly due to loss in qmAb. Clone 87 was relatively stable under selection conditions with a drop in the maximal titer and qmAb less than 15%. When the selection was removed, the maximal titer and qmAb of clone 87 dropped by more than 35%. Interestingly, clone 98 exhibited no change in qmAb and increased maximal titer in the absence of G418 but loss in production with the presence of G418.

TABLE 2

Production stability analysis of top mAb expressing clones

| Clone | Selection (±) | Max. titer (mg/L) P0 | P25 | Decrease (%) | qP (pg/cell/day) P0 | P25 | Decrease (%) |
|---|---|---|---|---|---|---|---|
| 50 | + | 399 | 113 | 72 | 31 | 7 | 77 |
|    | − |     | 87  | 78 |    | 5 | 84 |
| 63 | + | 434 | 187 | 57 | 33 | 12 | 64 |
|    | − |     | 132 | 70 |    | 5 | 85 |
| 87 | + | 513 | 441 | 14 | 20 | 18 | 10 |
|    | − |     | 279 | 46 |    | 13 | 35 |
| 97 | + | 461 | 271 | 41 | 20 | 10 | 50 |
|    | − |     | 209 | 55 |    | 5 | 75 |
| 98 | + | 268 | 224 | 16 | 22 | 8 | 32 |
|    | − |     | 320 | −19 |   | 22 | 0 |

Product Quality in Clones Generated Using Improved Tricistronic Vector

Figure 11A:
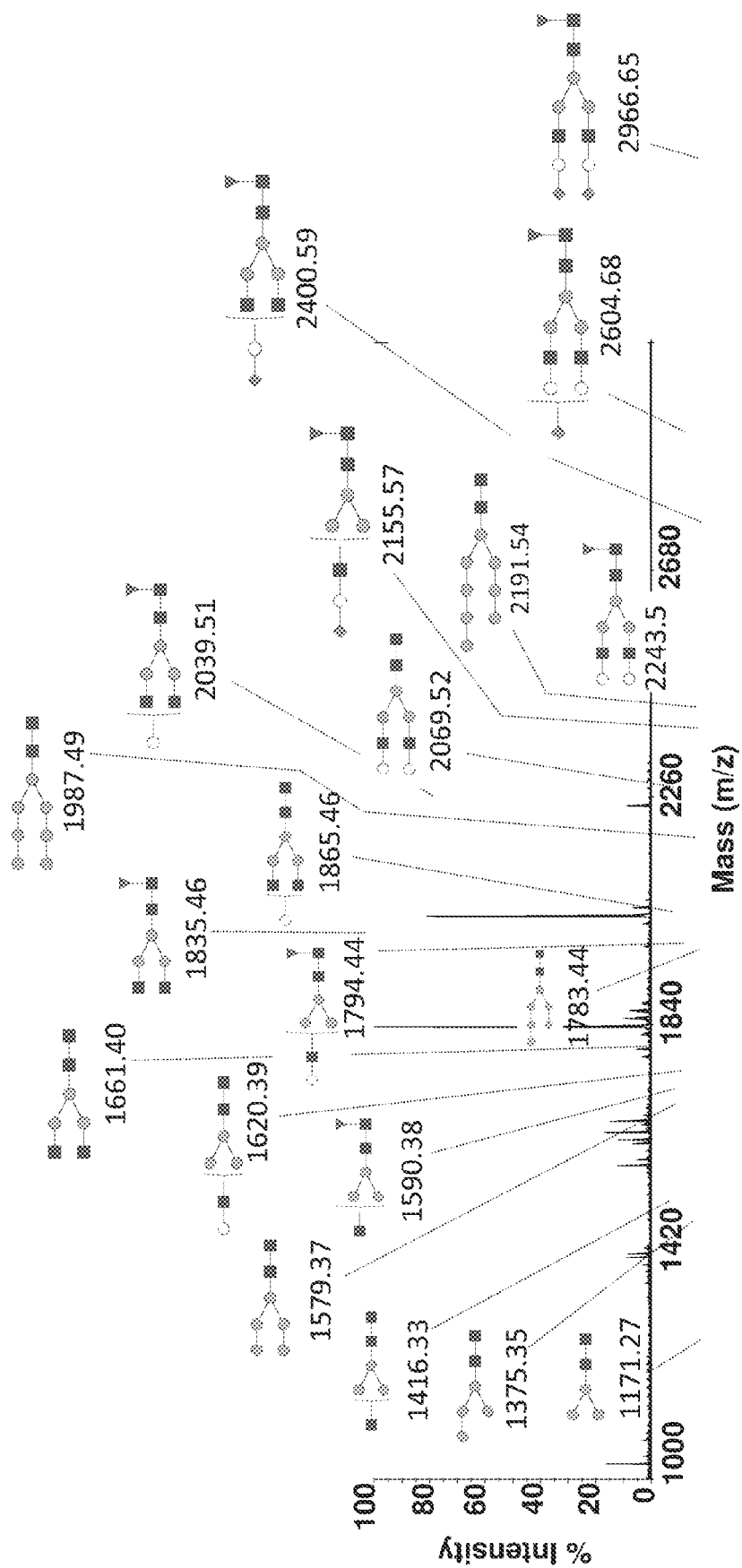
FIG. 11 shows glycan structures and distribution on recombinant mAb produced by the clones described in the legend of FIG. 10. (A) MALDI-TOF analysis of the permethylated N-glycans released from the recombinant mAb produced in the clone 50 as an example. The mass spectrum presented was of the 35% and 50% acetonitrile combined fractions. Solid square, N-acetylglucosamine; solid circle, mannose; open circle, galactose; solid triangle, fucose and solid diamond, sialic acid. (B) Glycan distribution on recombinant mAb produced in selected clones. N-glycans are categorized into high mannose-type, complex-type, sialylated which are substituted at least by one sialic acid residue in terminal position, fucosylated complex N-glycans, G0 without bearing terminal galactose residue, G1 bearing one terminal galactose residue and G2 bearing two terminal galactose. The numbers presented given are the average and standard deviation of 3 independent N-glycan preparations.
Figure 11B:
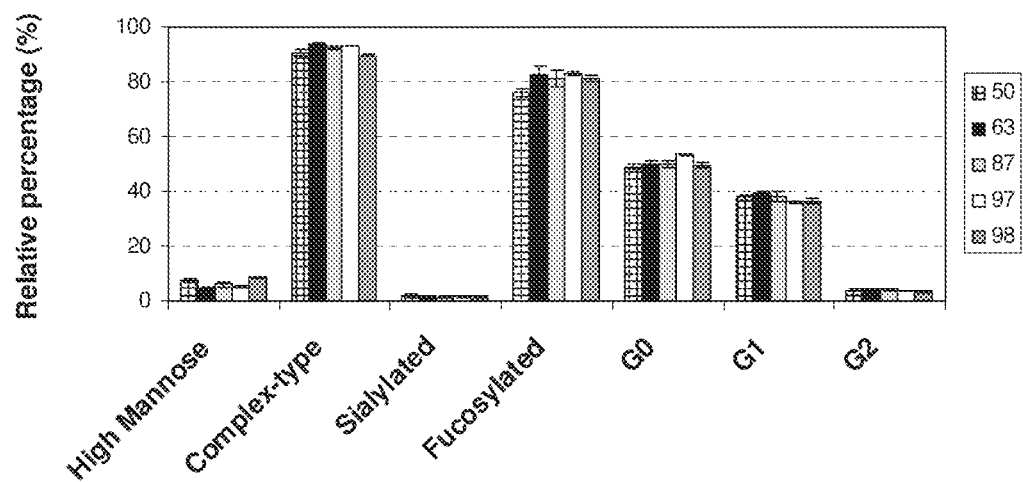

Beside productivity and production stability, mAb quality, such as glycosylation and aggregation, are also important parameters for clone selection. High aggregation of mAb will result in immunogenicity and glycosylation can affect both mAb activity and clearance. Glycosylation on mAb produced in the top 5 expressing clones was analyzed using MALDI-TOF mass spectrometry. A typical N-linked glycan profile for a recombinant IgG produced in CHO cells was presented (FIG. 11A). Ions were assigned to permethylated N-linked glycan structures corresponding to high mannose type N-glycans going from Man-4 to Man-8, complex-type N-glycans without any terminal galactose residue, G0, having one terminal galactose residue, G1, two terminal galactose residue, G2, and finally sialylated N-glycans which are bearing at least one sialic acid as a substituent of the non-reducing end of the N-glycans (FIG. 8A). A relative quantification of the N-glycans profile gave the same results across the five clones and statistical analysis (ANOVA test) of all the observed glycoforms did not show any significant differences between the different clones (FIG. 11B, Table 3, below). These latter structures are representing less than two percent of the total N-glycans which is expected for an IgG as reported in the literature (Jefferis, 2001; Raju et al., 2000; Rudd et al., 2001). The detected N-glycan profiles were comparable with the glycosylation of other IgGs produced in CHO cells (Jefferis, 2005; Van Berkel et al., 2009), regarding the dominant N-glycan structures such as core-fucosylated complex-type N-glycans with zero or one galactose, fully galactosylated core-fucosylated complex-type N-glycans.

TABLE 3

| Clones | 50 | 63 | 98 | 87 | 97 |
|---|---|---|---|---|---|
| High Mannose-Type | | | | | |
| 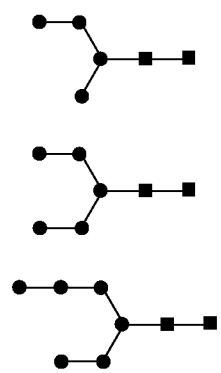 | 0.72 +/− 0.25 | 0.54 +/− 0.04 | 0.77 +/− 0.09 | 0.53 +/− 0.05 | 0.49 +/− 0.03 |
|  | 4.93 +/− 0.32 | 2.35 +/− 0.45 | 6.36 +/− 0.30 | 3.58 +/− 0.84 | 3.12 +/− 0.343 |
|  | 0.74 +/− 0.22 | 0.70 +/− 0.16 | 0.60 +/− 0.06 | 0.8 +/− 0.04 | 0.66 +/− 0.07 |

TABLE 3-continued
| Clones | 50 | 63 | 98 | 87 | 97 |
|---|---|---|---|---|---|
| 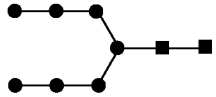 | 0.63 +/- 0.20 | 0.59 +/- 0.16 | 0.48 +/- 0.07 | 0.76 +/- 0.22 | 0.62 +/- 0.07 |
| 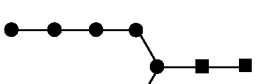 | 0.52 +/- 0.23 | 0.38 +/- 0.05 | 0.32 +/- 0.07 | 0.36 +/- 0.03 | 0.37 +/- 0.05 |
| G0 | | | | | |
| 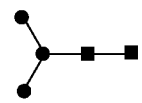 | 0.62 +/- 0.24 | 0.49 +/- 0.01 | 0.59 +/- 0.09 | 0.56 +/- 0.05 | 0.43 +/- 0.03 |
| 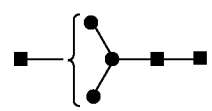 | 3.36 +/- 0.67 | 2.52 +/- 1.26 | 3.01 +/- 0.74 | 2.58 +/- 1 | 3.44 +/- 0.13 |
| 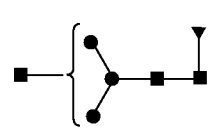 | 2.16 +/- 0.19 | 1.18 +/- 0.08 | 2.98 +/- 0.11 | 1.47 +/- 0.3 | 1.16 +/- 0.10 |
| 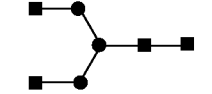 | 5.80 +/- 0.25 | 4.57 +/- 0.84 | 2.65 +/- 0.15 | 4.68 +/- 0.77 | 3.20 +/- 0.26 |
| 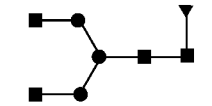 | 36.96 +/- 1.17 | 41.43 +/- 0.90 | 40.33 +/- 0.70 | 40.62 +/- 1.79 | 45.3 +/- 0.74 |
| G1 | | | | | |
| 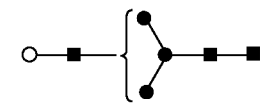 | 2.84 +/- 0.47 | 2.22 +/- 0.97 | 2.35 +/- 0.48 | 2.2 +/- 0.6 | 2.54 +/- 0.10 |
| 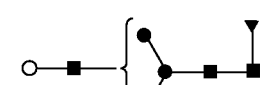 | 2.30 +/- 0.09 | 1.34 +/- 0.13 | 2.80 +/- 0.02 | 1.31 +/- 0.19 | 1.19 +/- 0.05 |
|  | 3.04 +/- 0.15 | 2.32 +/- 0.19 | 1.36 +/- 0.09 | 2.16 +/- 0.24 | 1.60 +/- 0.09 |
| 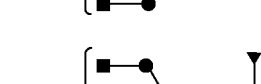 | 29.64 +/- 1.3 | 33.45 +/- 1.77 | 30.00 +/- 1.26 | 32.59 +/- 2.25 | 30.67 +/- 0.50 |
| G2 | | | | | |
| 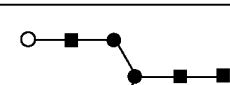 | 0.77 +/- 0.27 | 0.58 +/- 0.07 | 0.41 +/- 0.10 | 0.48 +/- 0.07 | 0.50 +/- 0.06 |

TABLE 3-continued

| Clones | 50 | 63 | 98 | 87 | 97 |
|---|---|---|---|---|---|
| [glycan structure] | 3.08 +/− 0.02 | 3.75 +/− 0.17 | 3.16 +/− 0.24 | 3.80 +/− 0.24 | 3.12 +/− 0.21 |
| Sialylated | | | | | |
| [glycan structure] | 0.63 +/− 0.12 | 0.59 +/− 0.16 | 0.79 +/− 0.17 | 0.48 +/− 0.10 | 0.48 +/− 0.10 |
| [glycan structure] | 0.43 +/− 0.25 | 0.35 +/− 0.05 | 0.44 +/− 0.06 | 0.34 +/− 0.04 | 0.37 +/− 0.04 |
| [glycan structure] | 0.47 +/− 0.23 | 0.39 +/− 0.07 | 0.37 +/− 0.07 | 0.45 +/− 0.06 | 0.45 +/− 0.03 |
| [glycan structure] | 0.36 +/− 0.22 | 0.26 +/− 0.04 | 0.23 +/− 0.07 | 0.25 +/− 0.05 | 0.29 +/− 0.06 |

Microheterogeneity of N-glycans structures found on the purified mAb produced in the top expressing clones. Five categories of N-glycans have been distinguished: high mannose-type N-glycans, complex-type N-glycans G0 which are the ones bearing no terminal galactose residue, complex-type N-glycans G1 which are having one terminal galactose, complex-type N-glycans G2 which are the ones with two terminal galactose and then, sialylated N-glycans which are the complex structures substituted by one or two sialic acids. The numbers reported here correspond to the percentage (%) of each N-glycan and are the mean of 3 independent analyses. Solid square, N-acetylglucosamine; solid circle, mannose; open circle, galactose; solid triangle, fucose; solid diamond, sialic acid.

Figure 12A:
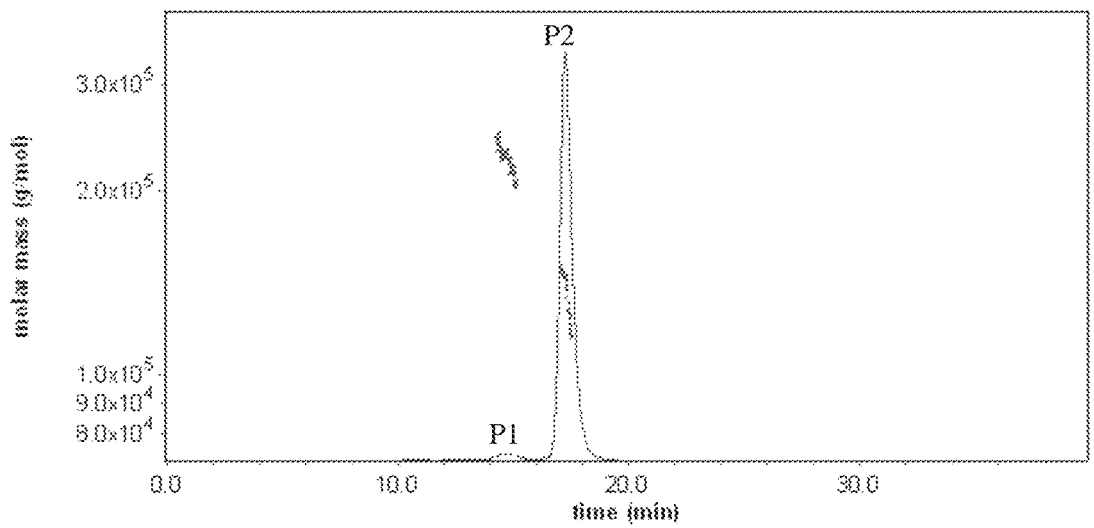
FIG. 12 shows a typical SEC chromatogram obtained for the top five expressing clones. (A) Species within protein A purified mAb from the top 5 expressing clones were separated by size exclusion chromatography followed by the identification of species based on molecular weight generated by light scattering detection. Peak P1 corresponds to aggregates and peak P2 corresponds to non-aggregated IgG monomers. (B) Chromatogram from UV detector showing similar peaks. Peak areas were used for the quantification of proteins detected as P1 and P2.

Furthermore, the aggregation of protein A purified mAb was determined using dynamic light scattering and UV detector, based on the hydrodynamic radius coupled with SEC chromatography. A typical SEC chromatogram of purified mAb is presented in FIG. 12. Based on the principle of SEC, the larger proteins were eluted first and the smaller proteins were eluted later. The second peak was identified as IgG monomer and the first peak was aggregates based on its molecular weight. On the basis of the area on the chromatogram, the proportion of aggregates was calculated. In all five samples, the IgG monomer fractions were above the same and had a hydrodynamic radius (Rh) of 5.6 nm and represented more than 98% of total protein composition. The results are shown in Table 4 below. Hence, the obtained clones produce mAbs with a very low degree of aggregation.

TABLE 4

| Clone | LC:HC | Aggregate % |
|---|---|---|
| 50 | ≈4 | 0.91 |
| 63 | ≈4 | 1.30 |
| 87 | ≈4 | 1.36 |
| 97 | ≈4 | 1.50 |
| 98 | ≈4 | 1.55 |

Table 4 shows that the high producing clones express excess of LC over HC and that after purification of the expressed mAbs only minimal amounts of aggregates are present.

As compared to Co-transfection and Multi-promoter vectors, using tricistronic vectors minimizes the number of non-expressing clones, enhances productivity, and controlled consistent product quality. These advantages are specifically obtained if tricistronic vectors comprise three key features: (1) expression of LC, HC, and selection marker in one transcript, (2) arrangement of LC as the first cistron and the HC as the second cistron where translation is driven by the IRES, and (3) attenuated IRES driven translation (by use of an attenuated IRES sequence, e.g., IRESatt) of an attenuated selectable marker, e.g., a weakened mutant NPT for selection. Tight coupling of the three genes in one transcript minimizes the number of non-expressing clones to 25%, as compared to 50 to 60% observed in those generated using Co-transfection and Multi-promoter vectors.

It was expected that the expression of the product and selection genes in one transcript would eliminate all non-expressing clones that arise due to vector fragmentation, as none of three genes will be expressed should incomplete vectors be integrated. However, the observation of non-expressing clones surviving drug selection is likely due to insertion of an intact NPT gene from a fragmented tricistronic vector, downstream of an endogenous promoter.

Furthermore, the above described tricistronic vectors allow for expression of two peptides or proteins of interest, e.g., LC and HC, in a single transcript and thus enables the control of the expression ratio between the two peptides or proteins of interest, e.g., the LC:HC ratio. This gives a consistent product patterns for all clones. For example, without a strict control of LC:HC expression, as in Co-transfection and Multi-promoter, the generated clones could produce either full mAb, HC fragments, LC fragments, or a mixture of them.

In addition, the data show that a consistent ratio of the expressed peptides or proteins of interest also influences their posttranslational modification. For example, the fixed LC:HC expression ratio leads to a consistent glycan distribution of the resulting which resembles the glycosylation of the commercially available and clinically approved mAb. Without wishing to be bound by any theory, it is believed that that glycosylation is affected by the protein folding and assembly process, which in turn is affected by the peptide or protein of interest ratio, e.g., the LC:HC ratio.

As IRES-driven gene translation efficiency is several folds lower than that of cap-dependant translation, placement of two peptides or proteins of interest, e.g., LC and HC, either in the first cistron of a tricistronic vector determines which peptide or protein is expressed in excess. In certain embodiments it is advantageous to place a certain peptide or protein of interest in the first cistron, to achieve excess of this entity over the peptide or protein of interest placed in the second cistron. For example, excess LC is more desirable for mAb production than excess HC, the LC-IRES-HC arrangement leads to higher mAb expression than the HC-IRES-LC configuration. Extra expression of LC may be also beneficial for minimization of mAb aggregation. Also, for purification purposes, excess of LC over HC may be beneficial, e.g.; if mAbs are to be purified using an antibody which is directed against the HC.

The data show that the ratio of LC:HC affects both mAb expression level and quality.

Furthermore, a weakened selection marker allows to enhance selection for high producers. In theory, the weaker the selection marker, the higher the threshold expression level required for clones to survive selection. The tricistronic design makes this strategy more effective as non-expressing clones can be minimized. The combination of attenuated IRES sequences controlling attenuated selectable markers further improves the selection of high producing clones.

Figures 12B, 13:
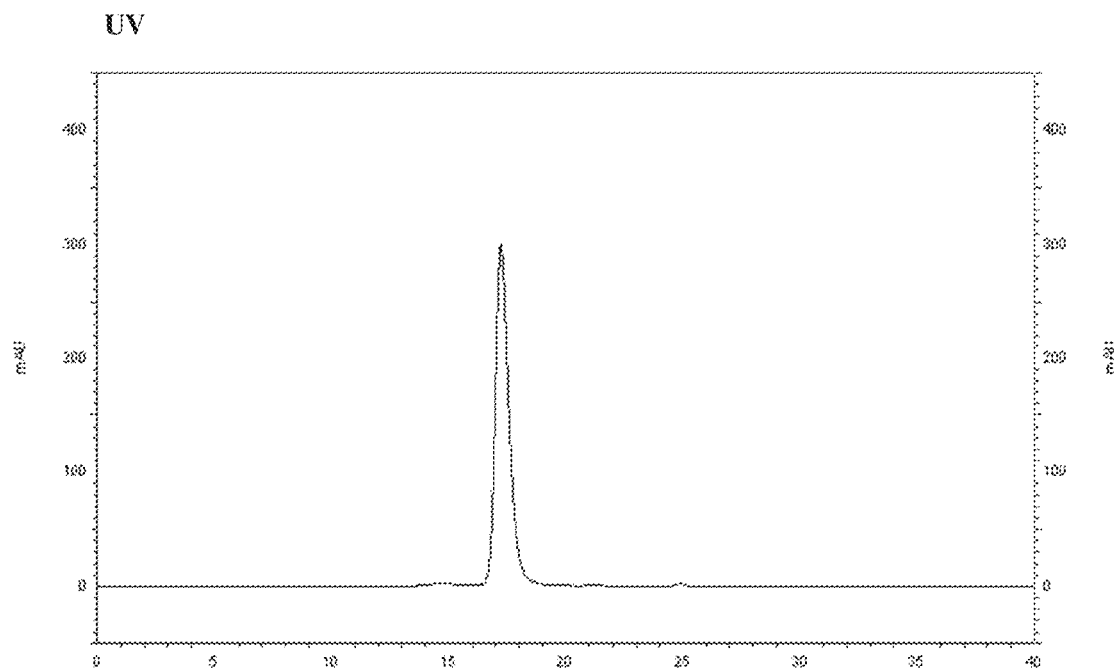
FIG. 13 shows schematic drawings of four tricistronic constructs employed in the following analyses. The name of each construct reflects the order of the cassettes comprised in the construct. L, antibody light chain (LC), H, antibody heavy chain (HC), I, IRES sequence, D, dihydrofolate reductase (DHFR). Furthermore, the table discloses the LC:HC expression ratio obtained using the corresponding construct.

Tricistronic Vectors Having a Selection Marker Under the Control of the Promoter In further experiments, tricistronic vectors for HER2 LC and HC expression having a selection marker under the control of the promoter were cloned. FIG. 13 shows schematic drawings of four tricistronic constructs employed in the following analyses. Vectors DILIH and DIHIL comprise the selection maker under the control of the CMV promoter.

Figure 14:
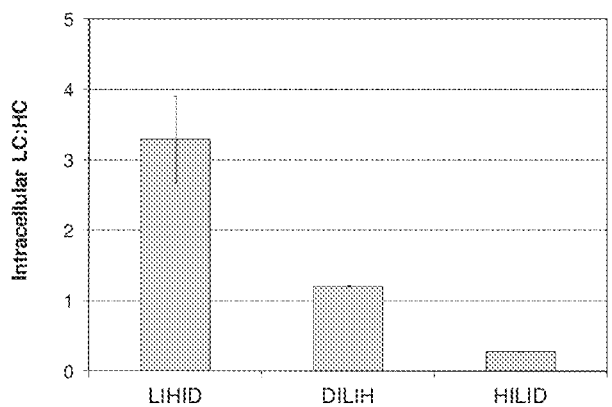
FIG. 14 shows the results of an expression analysis of CHO DG44 cells transfected with the indicated tricistronic constructs. The determined intracellular LC:HC ratio is given for each construct. Stably transfected pools were obtained by HT removal and MTX amplification. $10^7$ cells from each population were lysed using RIPA buffer supplemented with a protease inhibitor cocktail. Intracellular proteins collected were quantified by ELISA using anti-human IgG Fc and anti-human IgG Kappa primary antibodies for detection of heavy chain and light chain peptides respectively. The ratio of the amounts of LC:HC was determined for each vector design. Each point and error bar represents replicates from 2 separate transfected pools for each plasmid.

CHO DG44 cells were transfected with the indicated tricistronic constructs. FIG. 14 shows the results of an analysis of the expression of the transfected cells. For each construct the intracellular LC:HC ratio was determined. Stably transfected cell pools were obtained by HT removal and MTX amplification. $10^7$ cells of each population were lysed using RIPA buffer supplemented with a protease inhibitor cocktail. The intracellular antibody proteins were collected and quantified by ELISA using anti-human IgG Fc and anti-human IgG Kappa primary antibodies for detection of heavy chain and light chain peptides, respectively. The ratio of the amounts of LC:HC was determined for each vector design. The results show that in transiently transfected cells the LIHID construct, wherein the marker is under control of an IRES sequence has the strongest excess of LC:HC, DILIH having a almost perfect 1:1 ratio, whereas HILID shows excess HC.

Figure 15:
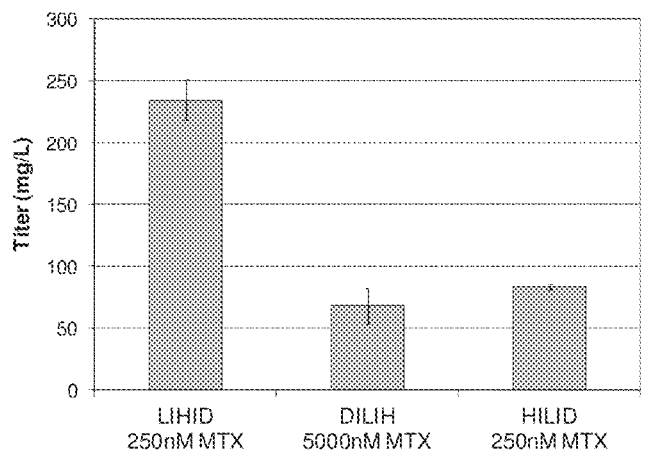
FIG. 15 shows a comparison of the antibody expression levels observed for different tricistronic vectors in stable transfections. The constructs are described in FIG. 13. In these experiments, cells were seeded with a density of $2 \times 10^5$ cells/mL in 50 mL of 50:50 media. The cell viability was tracked until it dropped to 50%. The supernatant was collected and the titer determined using a nephelometer. The peak average titer was determined. Each point in the graph represents average of 2 separately transfected cultures. The same samples were also used for the following Western Blot analysis and glycosylation analysis.

Afterwards, the constructs were tested in stably transfected CHO DG44 cells. FIG. 15 shows a comparison of the antibody expression levels observed for the three different tricistronic vectors. In these experiments, cells were seeded with a density of $2\times10^5$ cells/mL in 50 mL of 50:50 media. The cell viability was tracked until it dropped to 50%. The supernatant was collected and the titer determined using a nephelometer. The peak average titer was determined. LIHID shows the highest titer using cell culture medium supplemented with 250 nM MTX. The same samples were also used for the following Western Blot analysis and glycosylation analysis.

Figure 16:
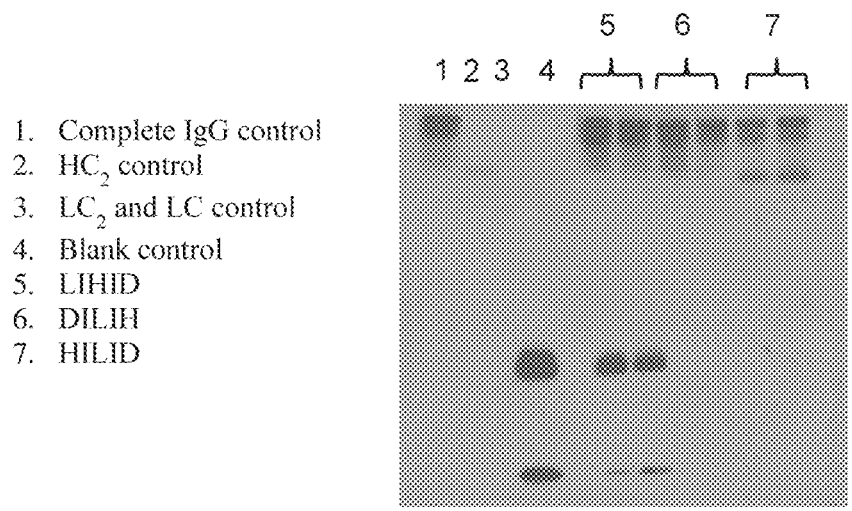
FIG. 16 shows the results of a western blot analysis. In this analysis, the supernatants of the cell culture described in the figure legend of FIG. 14 and suitable controls were loaded on an SDS-gel under non-reducing condition, as disclosed herein.

The western blot analysis revealed (cf. FIG. 16) that LIHID transfected cells besides intact mAbs produced large amounts of LC and $LC_2$. DILIH transfected cells produced intact mAbs only, whereas HILID produced intact mAbs and $HC_2$.

Figure 17:
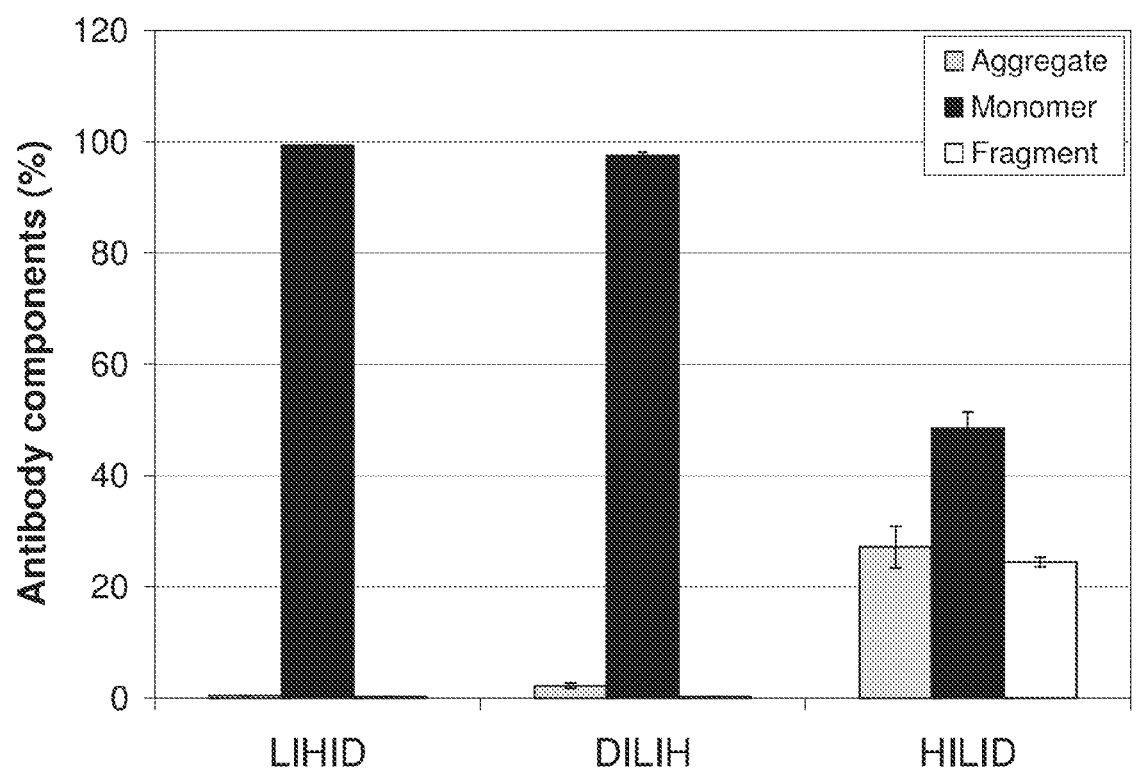
FIG. 17 shows the results of an aggregation analysis of the antibodies produced in the experiment described in the figure legend of FIG. 14. In more detail, the cell cultures maintained until viability reached 50% and the supernatant was collected and purified using protein A. The degree of aggregation was determined using size exclusion chromatography and protein species identified using light scattering and UV detector. The peak areas of the chromatogram were used for quantification of respective IgG aggregates, monomers and fragments. The purified products from LIHID and DILIH comprised almost only the desired IgG monomer product while significant undesired aggregates and fragments were observed for HILID. Only 50% of the product from HILID was monomers whereas 25% were aggregates and another 25% were fragments.

Afterwards, the aggregation state of the mAbs resulting from the culture of transfected cells was analyzed (cf. FIG. 17). Therefore, the cell cultures were maintained until viability reached 50% and the supernatant was collected and purified using protein A. The aggregation of protein A purified mAb was determined using dynamic light scattering and a UV detector, using the hydrodynamic radius in combination with SEC chromatography. Based on the principle of SEC, the larger proteins were eluted first and the smaller proteins were eluted later.

The peak areas of the chromatogram were used for quantification of respective IgG aggregates, monomers and fragments. The purified products from LIHID and DILIH comprised almost only the desired IgG monomer product while significant undesired aggregates and fragments were observed for HILID. Only 50% of the product from HILID was monomers whereas 25% were aggregates and another 25% were fragments. Hence, the protein secreted from DILIH transfected cells is mainly monomeric mAbs.

Figure 18A:
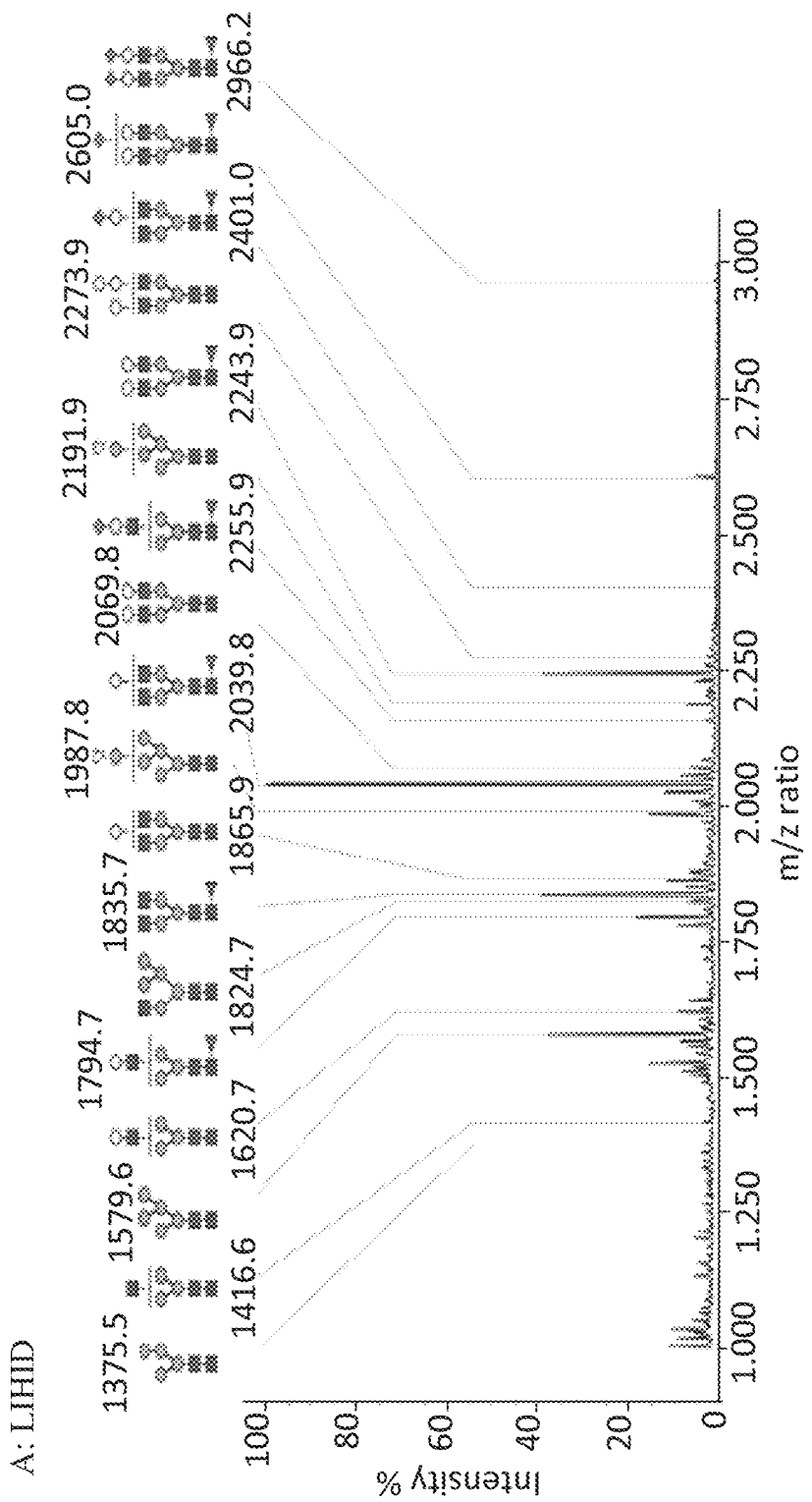
FIG. 18 shows the results obtained from an MS analysis of the glycosylation state of the antibodies obtained from the experiment described in the figure legend of FIG. 14. For all species, N-linked glycoforms were identified using MALDI-TOF mass spectrometry analysis of protein A purified samples. (A), (B) LIHID and DILIH, respectively, glycan species observed were similar to that reported by the manufacturer of Herceptin antibody. (C) for HILID a lot more complex glycan species were detected which have previously not been observed.
Figure 18B:
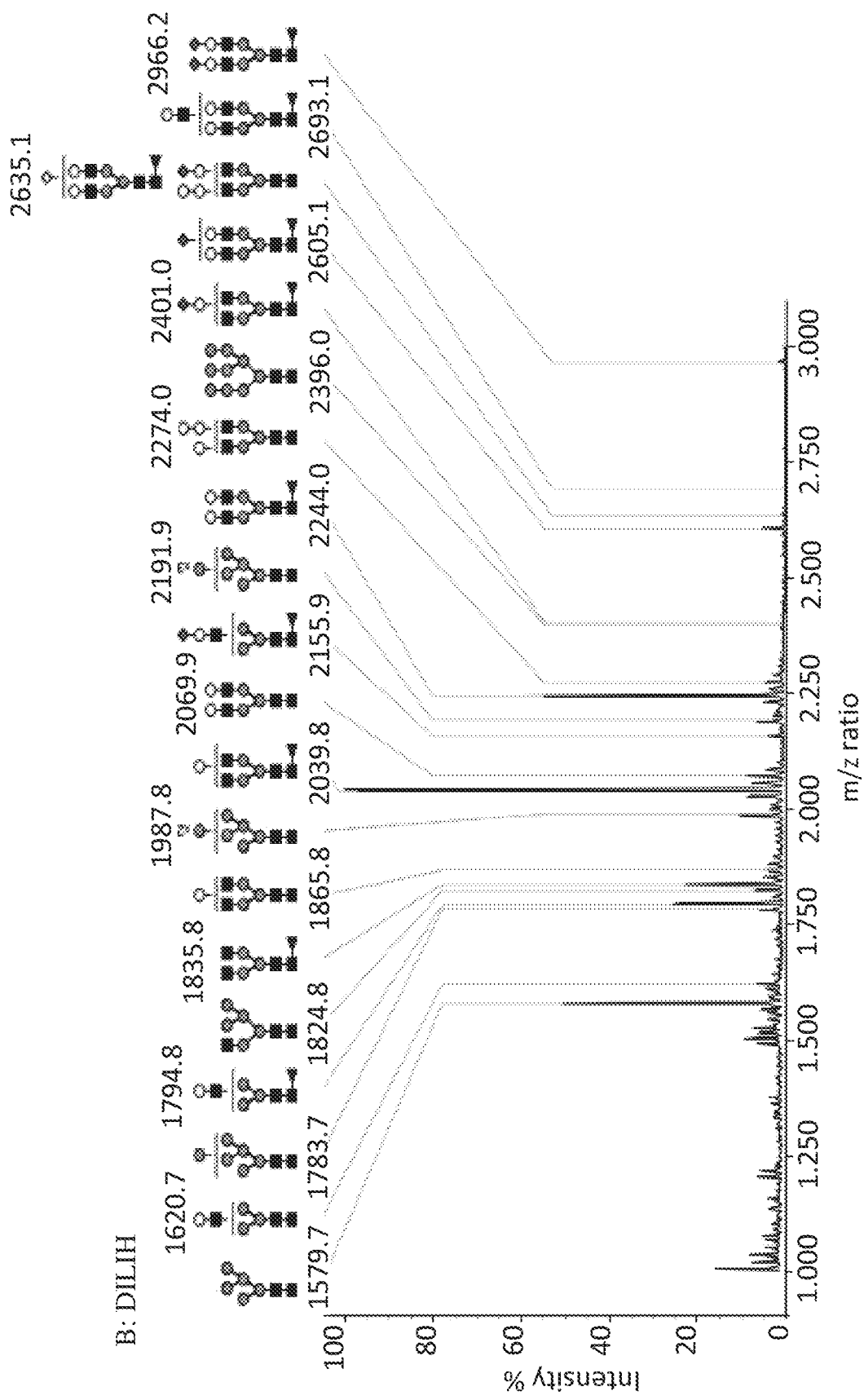
Figure 18C:
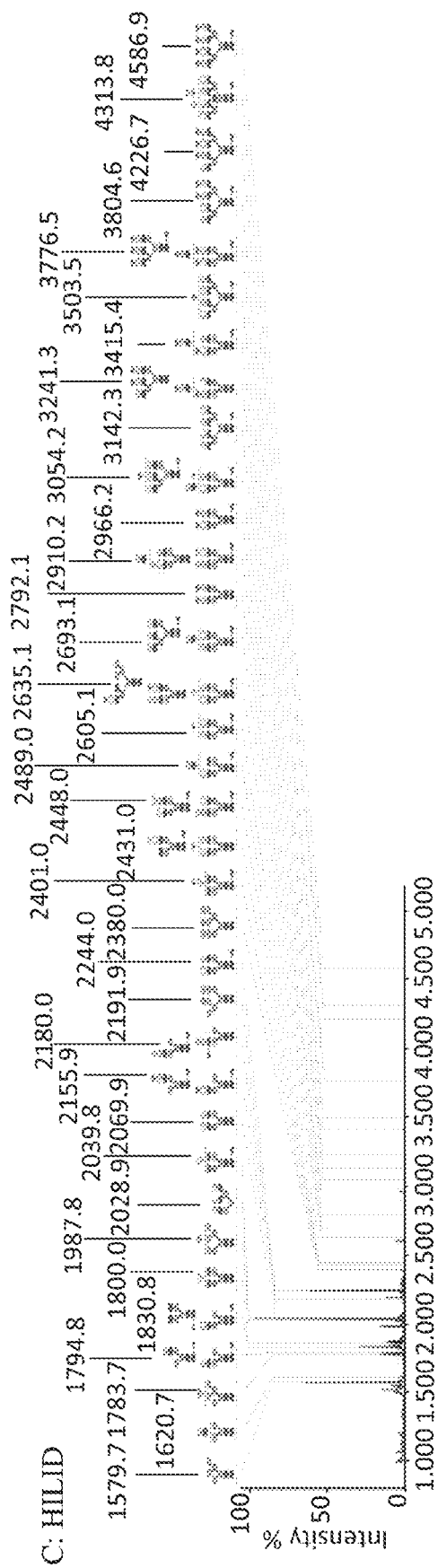

In order to further characterize the mAbs secreted by the transfected cells, the glycosylation of the mAbs was investigated. An appropriate glycosylation is important to avoid any negative inflammatory effects in clinical trials. FIG. 18 shows the results obtained from an MS analysis of the glycosylation state of the antibodies obtained in the experiment. For all species, N-linked glycoforms were identified using MALDI-TOF mass spectrometry analysis of protein A purified samples. (A), (B) LIHID and DILIH, respectively, glycan species observed were similar to that reported by the manufacturer of Herceptin antibody. (C) for HILID a lot more complex glycan species were detected which have previously not been observed. Accordingly, the monomeric mAbs secreted from DILIH or LIHID transfected cells have an appropriate glycosylation state resembling the state of clinically approved antibodies.

Figure 19:
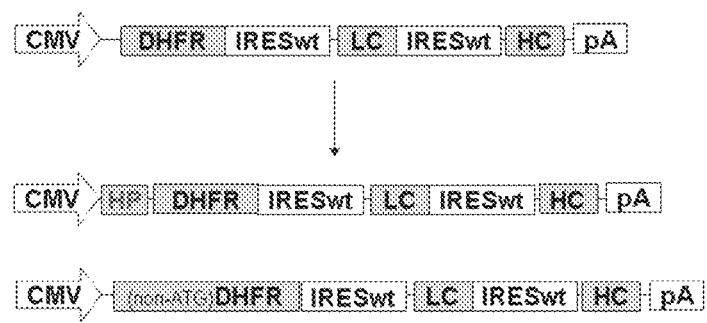
FIG. 19 shows a schematic drawing of further tricistronic constructs. These constructs are examples intended to illustrate the weakening of DHFR to enhancing the selection of high producers. For example, to enhance selection stringency for high producers, DHFR of the DILIH construct can be manipulated. One alternative may be to (1) insert DNA elements in front of DHFR, e.g., a hairpin structure. After transcription, the RNA will form a hairpin structure which will inhibit translation of DHFR; Another alternative is (2) to use a non-ATG start codon which reduces translation of DHFR.

FIG. 19 shows a schematic drawing of further tricistronic constructs. These constructs are examples to illustrate strategies to further weaken DHFR to enhance the selection of high producers. For example, in order to enhance selection stringency for high producers, DHFR of the DILIH construct can be manipulated. One alternative may be to (1) insert DNA elements in front of DHFR, e.g., a hairpin structure. After transcription, the RNA will form a hairpin structure which will inhibit translation of DHFR. Another alternative is (2) to use a non-ATG start codon which reduces the transcription of DHFR. Of course these strategies can be employed to alternative selection markers in the same or other vector systems.

All documents cited herein are hereby incorporated by reference in their entirety.

The embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the inventions claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The inventions have been described broadly and generically herein. Each of the narrower species and subgeneric groupings falling within the generic disclosure also form part of various embodiments of the invention. This includes the generic description with a proviso or negative limitation removing any subject matter from the genus, regardless of whether or not the excised material is specifically recited herein. In addition, where features or aspects are described in terms of Markush groups, those skilled in the art will recognize that other embodiments are also thereby described in terms of any individual member or subgroup of members of the Markush group. Further embodiments of the invention will become apparent from the following claims.

We claim:

1. An isolated nucleic acid molecule comprising:
   at least one nucleic acid sequence encoding for a peptide or protein of interest,
   at least one nucleic acid sequence encoding for a selectable marker, and
   at least one internal ribosome entry site (IRES) sequence, wherein
   the at least one IRES sequence is located between the at least one nucleic acid sequence encoding for the peptide or protein of interest and the at least one nucleic acid sequence encoding for the selectable marker, and
   the at least one nucleic acid sequence encoding for a selectable marker has a reduced translation efficiency and/or the encoded selectable marker is mutated such that it has a lowered activity compared to its wildtype variant,
   wherein the at least one IRES sequence comprises a nucleic acid sequence selected from the group of the nucleic acid sequences set forth in SEQ ID NO:02-57 and 83-112, wherein the at least one IRES sequence has a mutation that reduces ribosome binding affinity compared to the corresponding wildtype IRES sequence, and wherein the encoded selectable marker is attenuated.

2. The nucleic acid molecule according to claim 1, wherein the at least one IRES sequence is selected from the group of the nucleic acid sequences set forth in SEQ ID NO: 30-57 and 98-112.

3. The nucleic acid molecule according to claim 1, wherein the nucleic acid molecule comprises:
   two nucleic acid sequences encoding for a peptide or protein of interest and
   two IRES sequences,
   wherein the two nucleic acid sequences encoding for a peptide or protein of interest encode for two distinct peptides or proteins of interest.

4. The nucleic acid molecule according to claim 3, wherein the nucleic acid molecule has the following 5' to 3' organization: A-B-C-D-E, A-B-E-D-C, or E-B-A-D-C, wherein
   A is a first nucleic acid sequence encoding for the first peptide or protein of interest,
   B is a first IRES sequence, C is a second nucleic acid sequence encoding for the second peptide or protein of interest,
D is a second IRES sequence, and
E is a nucleic acid sequence encoding for a selectable marker, wherein the encoded selectable marker is attenuated.

5. The nucleic acid molecule according to claim 4, wherein the nucleic acid molecule has the organization A-B-C-D-E and D has a reduced ribosome binding affinity compared to the corresponding wildtype IRES sequence and wherein D is selected from the group of the sequences set forth in SEQ ID NO:30-57 and 98-112; or
the nucleic acid molecule has the organization A-B-E-D-C and B has a reduced ribosome binding affinity compared to the corresponding wildtype IRES sequence and wherein B is selected from the group of the sequences set forth in SEQ ID NO:30-57 and 98-112, or
the nucleic acid molecule has the organization E-B-A-D-C.

6. The nucleic acid molecule according to claim 1, wherein the at least one selectable marker is selected from the group consisting of a fluorescent protein, an enzyme, an antibiotic resistance gene, and an auxotrophic gene.

7. The nucleic acid molecule according to claim 6, wherein the selectable marker is selected from the group consisting of green fluorescent protein (GFP), a luciferase, a peroxidase, neomycin phosphotransferase, dihydrofolate reductase, thymidylate synthase, glutamine synthetase, puromycin-N-acetyl transferase, and the enzyme encoded by the Sh ble gene.

8. The nucleic acid molecule according to claim 1, wherein the nucleic acid sequence encoding the at least one selectable marker is selected from the group of the nucleic acid sequences set forth in SEQ ID NOs: 62 and 67-69 or wherein the nucleic acid sequence encoding the at least one selectable marker encodes a protein having a sequence selected from the group of the sequences as set forth in SEQ ID NOs: 63-66 and 70-77.

9. The nucleic acid molecule according to claim 1, wherein the nucleic acid molecule encoding for the selectable marker encodes for a selectable marker which is less active than its corresponding wildtype selectable marker, wherein the reduction in activity is by at least 10, 20, 30, 40, 50, 60, 70, 80, 90, 95, 97, 98, or 99% compared to the wildtype selectable marker.

10. The nucleic acid molecule according to claim 1, wherein the nucleic acid molecule further comprises a nucleic acid sequence directly 5' to the nucleic acid sequence encoding the selectable marker that when expressed in a cell forms a secondary structure within the mRNA and causes a reduced translation efficiency of the sequence encoding the selectable marker.

11. The nucleic acid molecule according to claim 10, wherein the sequence being directly 5' to the at least one nucleic acid sequence encoding the selectable marker forms a secondary structure within the mRNA and causes a reduced translation efficiency of the sequence encoding the selectable marker is selected from the group consisting of sequences forming a hairpin and a sequence forming a stem-loop.

12. The nucleic acid molecule according to claim 11, wherein the nucleic acid sequence 5' to the nucleic acid sequence encoding the selectable marker has a modified codon usage and/or comprises a non-ATG start codon.

13. The nucleic acid molecule according to claim 1, wherein the at least one selectable marker is a neomycin phosphotransferase having a reduced enzymatic activity which is lowered at least by 10, 20, 30, 40, 50, 60, 70, 80, 90, 95, 97, 98, or 99% compared to the wildtype enzyme.

14. The nucleic acid molecule according to claim 13, wherein the nucleic acid sequence encoding for the neomycin phosphotransferase is selected from the group of the sequences as set forth in SEQ ID NO: 67-69 or wherein the nucleic acid sequence encoding the neomycin phosphotransferase encodes a protein having a sequence selected from the group of the sequences as set forth in SEQ ID NOs: 64-66 and 70-77.

15. The nucleic acid molecule according to claim 1, wherein the at least one nucleic acid sequence encoding for the peptide or protein of interest is selected from the group of sequences consisting of sequences encoding for an antibody, an antibody fragment, an antibody light chain (LC), an antibody heavy chain (HC), an fab fragment, and a fusion protein comprising or consisting of an antibody light chain (LC), a protein2A, and an antibody heavy chain (LC).

16. The nucleic acid molecule according to claim 3, wherein the two peptides or proteins of interest encoded by the two nucleic acid sequences encoding for a peptide or protein of interest
a) interact with each other, and/or
b) form a complex.

17. The nucleic acid molecule according to claim 4, wherein the nucleic acid molecule has the following 5' to 3' organization:
a) A-B-C-D-E, wherein A is an antibody light chain, C is an antibody heavy chain, D has a reduced ribosome binding affinity compared to the corresponding wildtype IRES sequence and D is selected from the group of the sequences as set forth in SEQ ID NO:30-57 and 98-112, and E is a neomycin phosphotransferase having a sequence as set forth in SEQ ID NO:64-66, 70-77;
b) A-B-E-D-C, wherein A is an antibody light chain, B has a reduced ribosome binding affinity compared to the corresponding wildtype IRES sequence and B is selected from the group of the sequences set forth in SEQ ID NO:30-57 and 98-112, E is a neomycin phosphotransferase having a sequence as set forth in SEQ ID NO:64-66, 70-77, and C is an antibody heavy chain;
c) E-B-A-D-C, wherein E is a neomycin phosphotransferase having a sequence selected from the group of the sequences as set forth in SEQ ID NO:64-66, 70-77 or is a dihydrofolate reductase, A is an antibody light chain, and C is an antibody heavy chain;
d) A-B-C-D-E, wherein A is an antibody heavy chain, C is an antibody light chain, D has a reduced ribosome binding affinity compared to the corresponding wildtype IRES sequence and D is selected from the group of the sequences as set forth in SEQ ID NO:30-57 and 98-112, and E is a neomycin phosphotransferase having a sequence selected from the group of the sequences as set forth in SEQ ID NO:64-66, 70-77;
e) A-B-E-D-C, wherein A is an antibody heavy chain, B has a reduced ribosome binding affinity compared to the corresponding wildtype IRES sequence and B is selected from the group of the sequences set forth in SEQ ID NO:30-57 and 98-112, E is a neomycin phosphotransferase having a sequence selected from the group of the sequences as set forth in SEQ ID NO:64-66, 70-77, and C is an antibody light chain; or
f) E-B-A-D-C, wherein E is a neomycin phosphotransferase having a sequence selected from the group of the sequences as set forth in SEQ ID NO:64-66, 70-77 or is a dihydrofolate reductase, A is an antibody heavy chain, and C is an antibody light chain.

18. The nucleic acid molecule according to claim 1, further comprising a promoter and a polyadenylation signal sequence.

19. The nucleic acid molecule according to claim 1, wherein the nucleic acid molecule is comprised in a vector.

20. An isolated host cell comprising an isolated nucleic acid molecule comprising
at least one nucleic acid sequence encoding for a peptide or protein of interest,
at least one nucleic acid sequence encoding for a selectable marker, and at least one IRES sequence, wherein
the at least one IRES sequence is located between the at least one nucleic acid sequence encoding for the peptide or protein of interest and the at least one nucleic acid sequence encoding for the selectable marker, and
the at least one nucleic acid sequence encoding for a selectable marker has a reduced translation efficiency and/or the encoded selectable marker is mutated such that it has a lowered activity compared to its wildtype variant and the at least one IRES sequence has a mutation that reduces ribosome binding affinity compared to the corresponding wildtype IRES sequence, wherein the at least one IRES sequence comprises a nucleic acid sequence selected from the group of the nucleic acid sequences set forth in SEQ ID NO:02-57 and 83-112, and wherein the encoded selectable marker is attenuated.

21. A method for expression of at least one recombinant peptide or protein of interest, wherein the method comprises:
(a) cultivating a host cell according to claim 20 in a culture medium under conditions that allow expression of the at least one recombinant peptide or protein of interest; and optionally
(b) purifying the at least one recombinant peptide or protein of interest.

22. The method according to claim 21, wherein the cultivating of step (a) is performed under conditions to allow expression of at least two recombinant peptides or proteins of interest.

23. The method according to claim 22, wherein the at least two recombinant proteins are an antibody light chain (LC) and an antibody heavy chain (HC).

24. An isolated nucleic acid molecule comprising a nucleic acid IRES sequence selected from the group of the nucleic acid sequences as set forth in SEQ ID NOs: 03-29, 31-37, and 83-112 and that has a mutation that reduces ribosome binding affinity compared to a corresponding wildtype sequence.

25. An isolated nucleic acid molecule comprising:
A: at least one nucleic acid sequence encoding for a selectable marker,
B: a first IRES sequence,
C: a first nucleic acid sequence encoding for a first recombinant peptide or protein of interest,
D: a second IRES sequence, and
E: a second nucleic acid sequence encoding for a second recombinant peptide or protein of interest,
wherein the 5' to 3' organization of the nucleic acid molecule is A-B-C-D-E,
wherein at least one of the first and second IRES sequences has a sequence selected from the group of the nucleic acid sequences set forth in SEQ. ID. NO: 02-57 and 83-112,
wherein the at least one IRES sequence has a mutation that reduces ribosome binding affinity compared to the corresponding wildtype IRES sequence; and
wherein the encoded selectable marker is attenuated.

26. The nucleic acid molecule according to claim 25, wherein
a) the at least one selectable marker is selected from the group consisting of GFP, a luciferase, a peroxidase, neomycin phosphotransferase, dihydrofolate reductase, glutamine synthetase, puromycin —N-acetyl transferase, and the enzyme encoded by the Sh ble gene, and/or
b) the first recombinant protein is an antibody light chain (LC) and the second recombinant protein is an antibody heavy chain (HC), or
c) the first recombinant protein is an antibody heavy chain (HC) and the second recombinant protein is an antibody light chain (LC).

27. A method for expression of a first and second recombinant peptide or protein of interest, wherein the method comprises:
(a) cultivating a host cell comprising a nucleic acid molecule according to claim 25,
wherein the host cell is cultivated in a culture medium under conditions that allow expression of the first and second recombinant peptide or protein of interest, and
(b) supplementing the culture medium with an inhibitor which increases the selection pressure on the host cell, and optionally
(c) purifying the first and second recombinant peptide or protein of interest.

28. A method of differentially expressing at least one bicistronic nucleic acid construct in a host cell transformed with the nucleic acid construct, wherein the at least one bicistronic construct comprises
(1) at least one first nucleic acid sequence encoding for a first recombinant peptide or protein of interest,
(2) at least one second nucleic acid sequence encoding for a second recombinant peptide or protein of interest, and
(3) at least one IRES sequence,
wherein the at least one IRES sequence is located between the at least one first nucleic acid sequence encoding for the first recombinant peptide or protein of interest and the at least one second nucleic acid sequence encoding for the second recombinant peptide or protein of interest, and wherein the at least one IRES sequence comprises a nucleic acid sequence selected from the group of the nucleic acid sequences set forth in SEQ ID NO:3-29, 31-57, and 83-112;
wherein the first and the second recombinant peptide or protein of interest interact with each other and/or form a complex, the first recombinant peptide or protein optionally being an antibody light chain and the second recombinant protein optionally being an antibody heavy chain;
wherein the at least one IRES sequence has a mutation that reduces ribosome binding affinity compared to the corresponding wildtype IRES sequence; and
wherein the method comprises cultivating the host cell in a culture medium suitable for expressing the first and the second recombinant peptide or protein of interest.

29. An isolated nucleic acid molecule comprising:
at least one first nucleic acid sequence encoding for a first peptide or protein of interest,
at least one second nucleic acid sequence encoding for a second peptide or protein of interest, and
at least one IRES sequence, wherein
the at least one IRES sequence is located between the at least one first nucleic acid sequence encoding for the first peptide or protein of interest and the at least one second nucleic acid sequence encoding for the second peptide or protein of interest, and the at least one IRES sequence comprises a nucleic acid sequence selected from the group of nucleic acid sequences set forth in SEQ ID NO:2-57 and 83-112, which is mutated such that it has a reduced ribosome binding affinity compared to a corresponding wild type IRES sequence, and wherein the two nucleic acid sequences encoding for a peptide or protein of interest encode for two distinct peptides or proteins of interest.

30. An isolated nucleic acid molecule, wherein the nucleic acid molecule comprises:
  a nucleic acid sequences encoding for a selectable marker and
  two IRES sequences, wherein
  the nucleic acid molecule has optionally the following 5' to 3' organization: A-B-C-D-E, A-B-E-D-C, or E-B-A-D-C, wherein
  A is a first nucleic acid sequence encoding for the first peptide or protein of interest,
  B is a first IRES sequence,
  C is a second nucleic acid sequence encoding for the second peptide or protein of interest,
  D is a second IRES sequence, and
  E is a nucleic acid sequence encoding for a selectable marker, wherein the nucleic acid molecule encoding for the selectable marker optionally encodes for a selectable marker which is less active than its corresponding wild-type selectable marker, wherein the reduction in activity is by at least 10, 20, 30, 40, 50, 60, 70, 80, 90, 95, 97, 98, or 99% compared to the wildtype selectable marker,
  wherein the two IRES sequences comprise or consist of a nucleic acid sequence selected from the group of the nucleic acid sequences set forth in SEQ ID NO:2-57 and 83-112;
  wherein the at least one IRES sequence has a mutation that reduces ribosome binding affinity compared to the corresponding wildtype IRES sequence;
  wherein the nucleic acid molecule optionally further comprises a nucleic acid sequence directly 5' to the nucleic acid sequence encoding the selectable marker that (1) when expressed in a cell forms a secondary structure within the mRNA and causes a reduced translation efficiency of the sequence encoding the selectable marker,
  wherein said sequence being directly 5' to the at least one nucleic acid sequence encoding the selectable marker optionally is selected from the group consisting of sequences forming a hairpin and a sequence forming a stem-loop, or (2) has a modified codon usage and/or comprises a non-ATG start codon,
  wherein the at least one selectable marker is optionally a neomycin phosphotransferase or dihydrofolate reductase having a reduced enzymatic activity which is lowered at least by 10, 20, 30, 40, 50, 60, 70, 80, 90, 95, 97, 98, or 99% compared to the wildtype enzyme,
  wherein the nucleic acid sequence encoding for the neomycin phosphotransferase is optionally selected from the group of the sequences as set forth in SEQ ID NO:67-69 or wherein the nucleic acid sequence encoding for the neomycin phosphotransferase encodes for a protein having a sequence selected from the group of the sequences as set forth SEQ ID NOs:64-66, 70-77, and
  wherein the at least one nucleic acid sequence encoding for the peptide or protein of interest is selected from the group of sequences consisting of sequences encoding for an antibody, an antibody fragment, an antibody light chain (LC), an antibody heavy chain (HC), an fab fragment, fusions of any two or more thereof, and a fusion protein comprising or consisting of an antibody light chain (LC), a protein2A, and an antibody heavy chain (LC).

31. The nucleic acid molecule according to claim 29, wherein the nucleic acid molecule comprises four nucleic acid sequences encoding for four distinct peptides or proteins of interest and four IRES sequences, wherein at least two IRES sequences are selected from the group of the nucleic acid sequences set forth in SEQ ID NO:2-57 and 83-112,
  wherein the four nucleic acid sequences encoding four distinct peptides or proteins of interest encode for two distinct antibody light chains and two distinct antibody heavy chains.

32. An isolated nucleic acid molecule comprising:
  first and second nucleic acid sequences encoding for a peptide or protein of interest,
  at least one nucleic acid sequence encoding for a selectable marker, and first and second IRES sequences, wherein
  the first or second IRES sequence is located between the first or second nucleic acid sequence encoding for a peptide or protein of interest and the at least one nucleic acid sequence encoding for the selectable marker,
  the at least one nucleic acid sequence encoding for a selectable marker has a reduced translation efficiency and/or the encoded selectable marker is mutated such that it has a lowered activity compared to its wildtype variant and the first or second IRES sequence is located 5' to the at least one nucleic acid sequence encoding for the selectable marker and has a mutation that reduces ribosome binding affinity compared to the corresponding wildtype IRES sequence,
  the first IRES sequence comprises a nucleic acid sequence selected from the group of the nucleic acid sequences set forth in SEQ ID NO:02-57 and 83-112, and the second IRES sequence comprises the nucleic acid sequence as set forth in SEQ ID NO: 1,
  wherein the first IRES sequence has a mutation that reduces ribosome binding affinity compared to the corresponding wildtype IRES sequence; and
  the first and second nucleic acid sequences encoding for a peptide or protein of interest each encode for a distinct peptide or protein of interest.

33. An isolated nucleic acid molecule comprising:
  A: at least one nucleic acid sequence encoding for a selectable marker,
  B: a first IRES sequence,
  C: a first nucleic acid sequence encoding for a first recombinant peptide or protein of interest,
  D: a second IRES sequence, and
  E: a second nucleic acid sequence encoding for a second recombinant peptide or protein of interest,
  wherein the 5' to 3' organization of the nucleic acid molecule is A-B-C-D-E and wherein the first IRES sequence comprises the nucleic acid sequence as set forth in SEQ ID NO: 1; and wherein the second IRES sequence has a mutation that reduces ribosome binding affinity compared to the corresponding wildtype IRES sequence.

* * * * *